(12) United States Patent
Chan et al.

(10) Patent No.: US 11,339,396 B2
(45) Date of Patent: May 24, 2022

(54) ENGINEERED VIRAL VECTOR REDUCES INDUCTION OF INFLAMMATORY AND IMMUNE RESPONSES

(71) Applicant: President and Fellows of Harvard College, Cambridge, MA (US)

(72) Inventors: Ying Kai Chan, Cambridge, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 567 days.

(21) Appl. No.: 16/308,420

(22) PCT Filed: Jun. 8, 2017

(86) PCT No.: PCT/US2017/036525
§ 371 (c)(1),
(2) Date: Dec. 7, 2018

(87) PCT Pub. No.: WO2017/214378
PCT Pub. Date: Dec. 14, 2017

(65) Prior Publication Data
US 2019/0177731 A1 Jun. 13, 2019

Related U.S. Application Data

(60) Provisional application No. 62/347,302, filed on Jun. 8, 2016.

(51) Int. Cl.
*C12N 15/117* (2010.01)
*A61K 45/06* (2006.01)
*A61K 31/7088* (2006.01)
*A61K 35/76* (2015.01)
*C12N 15/86* (2006.01)
*A61P 29/00* (2006.01)
*C12N 7/00* (2006.01)
*A61K 48/00* (2006.01)

(52) U.S. Cl.
CPC ........ *C12N 15/117* (2013.01); *A61K 31/7088* (2013.01); *A61K 35/76* (2013.01); *A61K 45/06* (2013.01); *A61P 29/00* (2018.01); *C12N 7/00* (2013.01); *C12N 15/86* (2013.01); *A61K 48/00* (2013.01); *C12N 2310/17* (2013.01); *C12N 2330/51* (2013.01); *C12N 2750/00032* (2013.01); *C12N 2750/00041* (2013.01); *C12N 2750/14143* (2013.01); *C12N 2750/14151* (2013.01); *C12N 2750/14171* (2013.01); *Y02A 50/30* (2018.01)

(58) Field of Classification Search
CPC .................................................. C12N 15/117
See application file for complete search history.

(56) References Cited

U.S. PATENT DOCUMENTS

| 5,618,696 | A | 4/1997 | Norris et al. |
|---|---|---|---|
| 5,643,890 | A | 7/1997 | Iversen et al. |
| 6,194,206 | B1 | 2/2001 | West et al. |
| 6,225,292 | B1 | 5/2001 | Raz et al. |
| 7,271,156 | B2 | 9/2007 | Krieg et al. |
| 7,314,926 | B1 | 1/2008 | Miller et al. |
| 7,514,414 | B2 | 4/2009 | Klinman et al. |
| 7,514,415 | B2 | 4/2009 | Klinman et al. |
| 7,723,054 | B2 | 5/2010 | Latz et al. |
| 7,879,812 | B2 | 2/2011 | Ashman et al. |
| 8,030,289 | B2 | 10/2011 | Wang et al. |
| 8,053,422 | B2 | 11/2011 | Klinman et al. |
| 8,153,141 | B2 | 4/2012 | Lipford et al. |
| 8,377,898 | B2 | 2/2013 | Kandimalla et al. |
| 8,486,908 | B2 | 7/2013 | Kandimalla et al. |
| 8,771,669 | B1 | 7/2014 | Bermudes |
| 8,853,177 | B2 | 10/2014 | Zhu et al. |
| 8,895,521 | B2 | 11/2014 | Klinman et al. |
| 8,933,011 | B2 | 1/2015 | O'Neill et al. |
| 9,006,203 | B2 | 4/2015 | Klinman et al. |
| 9,096,858 | B2 | 8/2015 | Kandimalla et al. |
| 9,540,651 | B2 | 1/2017 | Kandimalla et al. |
| 10,124,062 | B2 | 11/2018 | O'Neil |
| 10,441,654 | B2 | 10/2019 | Korneluk et al. |
| 2003/0176376 | A1 | 9/2003 | Klem |
| 2004/0097455 | A1 | 5/2004 | Borunda et al. |

(Continued)

FOREIGN PATENT DOCUMENTS

| CN | 101712957 A | 5/2010 |
|---|---|---|
| CN | 102925485 A | 2/2013 |

(Continued)

OTHER PUBLICATIONS

Martino et al. (Blood, Jun. 16, 2011; 117(24): 6459-6468) (Year: 2011).*
Kreig et al. (Proc. Natl. Acad. Sci. USA; Oct. 1998 95:12631-12636) (Year: 1998).*
Stunz et al. (Eur. J. Immunol. 2002. 32: 1212-1222). (Year: 2002).*
Ashman et al., Sequence requirements for oligodeoxyribonucleotide inhibitory activity. Int Immunol. Apr. 2005;17(4):411-20.
Ashman et al., Optimal oligonucleotide sequences for TLR9 inhibitory activity in human cells: lack of correlation with TLR9 binding. Int Immunol. Mar. 2011;23(3):203-14. doi: 10.1093/intimm/dxq473.

(Continued)

*Primary Examiner* — Scott Long
(74) *Attorney, Agent, or Firm* — Wolf, Greenfield & Sacks, P.C.

(57) ABSTRACT

Modified viral genomes are able to reduce induction of inflammatory and immune anti-viral responses. This manifests itself in reduced NF-kB activity, increased viral transduction rates, and increased expression of transgenes. Viral genomes are modified by incorporating one or more oligonucleotide sequences which are able to bind to TLR9 but not induce activation of it. The oligonucleotide sequences may be synthetic, bacterial, human, or from any other source.

22 Claims, 18 Drawing Sheets

Specification includes a Sequence Listing.

(56) References Cited

U.S. PATENT DOCUMENTS

| | | |
|---|---|---|
| 2004/0132682 A1 | 7/2004 | Klinman et al. |
| 2004/0248834 A1 | 12/2004 | Klinman et al. |
| 2005/0239733 A1 | 10/2005 | Jurk et al. |
| 2006/0074039 A1 | 4/2006 | Klinman et al. |
| 2007/0020624 A1 | 1/2007 | Rubenfield et al. |
| 2009/0081157 A1 | 3/2009 | Kornbluth et al. |
| 2009/0082288 A1 | 3/2009 | Klinman et al. |
| 2009/0142310 A1 | 6/2009 | Klinman et al. |
| 2009/0208468 A1 | 8/2009 | Klinman et al. |
| 2010/0069467 A1 | 3/2010 | Boye et al. |
| 2010/0144839 A1 | 6/2010 | Klinman et al. |
| 2011/0033448 A1 | 2/2011 | Gilliet et al. |
| 2011/0070241 A1 | 3/2011 | Yang |
| 2011/0077289 A1 | 3/2011 | Klinman et al. |
| 2011/0182927 A1 | 7/2011 | Raz et al. |
| 2011/0201676 A1 | 8/2011 | Klinman et al. |
| 2011/0236392 A1 | 9/2011 | O'Neill et al. |
| 2011/0251264 A1 | 10/2011 | McArthur et al. |
| 2012/0009170 A1 | 1/2012 | Klinman et al. |
| 2012/0016013 A1 | 1/2012 | Klinman et al. |
| 2012/0076763 A1 | 3/2012 | Anderson et al. |
| 2012/0128699 A1 | 5/2012 | Kandimalla et al. |
| 2012/0258144 A1 | 10/2012 | Klinman et al. |
| 2013/0018089 A1 | 1/2013 | Klinman et al. |
| 2013/0101558 A1 | 4/2013 | Gao et al. |
| 2013/0281518 A1 | 10/2013 | Klinman et al. |
| 2014/0004100 A1 | 1/2014 | Kandimalla et al. |
| 2014/0134233 A1 | 5/2014 | Klinman et al. |
| 2014/0271550 A1 | 9/2014 | Rabinowitz et al. |
| 2015/0238550 A1 | 8/2015 | McCown et al. |
| 2015/0299710 A1 | 10/2015 | Esashi et al. |
| 2015/0320800 A1 | 11/2015 | Contag et al. |
| 2017/0035864 A1 | 2/2017 | Theriault |
| 2017/0190778 A1 | 7/2017 | Layne et al. |
| 2017/0233741 A1 | 8/2017 | Kandimalla et al. |
| 2018/0023085 A1 | 1/2018 | Kandimalla et al. |
| 2018/0275120 A1 | 9/2018 | Lee |
| 2018/0325890 A1 | 11/2018 | De Lonlay-Debeney et al. |
| 2019/0316151 A1 | 10/2019 | Chan et al. |
| 2020/0270637 A1 | 8/2020 | Chan et al. |

FOREIGN PATENT DOCUMENTS

| | | |
|---|---|---|
| EP | 3329004 B1 | 1/2020 |
| JP | 2002-505580 A | 2/2002 |
| JP | 2013-544816 A | 12/2013 |
| JP | 2015-532095 A | 11/2015 |
| JP | 2015-536659 A | 12/2015 |
| WO | WO 1998/055495 A2 | 12/1998 |
| WO | WO 2003/103586 A2 | 12/2003 |
| WO | WO 2004/048511 A2 | 6/2004 |
| WO | WO 2005/013891 A2 | 2/2005 |
| WO | WO 2005/035579 A1 | 4/2005 |
| WO | WO 2005/111211 A2 | 11/2005 |
| WO | WO 2005/116250 A2 | 12/2005 |
| WO | WO 2006/028742 A2 | 3/2006 |
| WO | WO 2006/035939 A1 | 4/2006 |
| WO | WO 2006/066003 A2 | 6/2006 |
| WO | WO 2007/047396 A2 | 4/2007 |
| WO | WO 2007/147011 A2 | 12/2007 |
| WO | WO 2008/104985 A2 | 9/2008 |
| WO | WO 2009/006141 A2 | 1/2009 |
| WO | WO 2009/023819 A2 | 2/2009 |
| WO | WO 2009/055076 A2 | 4/2009 |
| WO | WO 2009/089399 A2 | 7/2009 |
| WO | WO 2009/089401 A2 | 7/2009 |
| WO | WO 2009/143292 A2 | 11/2009 |
| WO | WO 2010/141483 A2 | 12/2010 |
| WO | WO 2011/005942 A2 | 1/2011 |
| WO | WO 2011/159328 A1 | 12/2011 |
| WO | WO 2011/159958 A2 | 12/2011 |
| WO | WO 012/022948 A1 | 2/2012 |
| WO | WO 2012/051491 A1 | 4/2012 |
| WO | WO 2012/068470 A2 | 5/2012 |
| WO | WO 2013/116590 A1 | 8/2013 |
| WO | WO 2014/001422 A2 | 1/2014 |
| WO | WO 2014/052789 A1 | 4/2014 |
| WO | WO 2014/082254 A1 | 6/2014 |
| WO | WO 2014/105870 A1 | 7/2014 |
| WO | WO 2014/110081 A1 | 7/2014 |
| WO | WO 2016/020377 A1 | 2/2016 |
| WO | WO 2016/070045 A1 | 5/2016 |
| WO | WO 2016/130832 A1 | 8/2016 |
| WO | WO 2016/149612 A2 | 9/2016 |
| WO | WO 2016/183370 A1 | 11/2016 |
| WO | WO 2017/111045 A1 | 6/2017 |
| WO | WO 2017/214378 A1 | 12/2017 |
| WO | WO 2018/095697 A1 | 5/2018 |
| WO | WO 2019/094548 A1 | 5/2019 |

OTHER PUBLICATIONS

Bessis et al., Immune responses to gene therapy vectors: influence on vector function and effector mechanisms. Gene Ther. Oct. 2004;11 Suppl 1:S10-7.

Beutler et al., TLRs and innate immunity. Blood. Feb. 2009;113(7):1399-1407. Online print version, https://www.ncbi.nlm.nih.gov/pmc/articles/PMC2644070/?report=printable. 21 pages.

Chan, Manipulating the Immune Response to Viral Pathogens and Gene Therapy Viral Vectors. Powerpoint Presentation slides. Loyola Seminar. 46 pages. Jun. 30, 2016.

Chan et al., Viral evasion of intracellular DNA and RNA sensing. Nat Rev Microbiol. Jun. 2016; 14:360-73. Epub May 13, 2016. Author Manuscript, 43 pages.

Chinnery et al., TLR9 ligand CpG-ODN applied to the injured mouse cornea elicits retinal inflammation. Am J Pathol. Jan. 2012;180(1):209-20. doi: 10.1016/j.ajpath.2011.09.041.

Chinnery et al., Retinal microglial activation following topical application of intracellular toll-like receptor ligands. Invest Ophthalmol Vis Sci. 2015;56(12):7377-86. doi: 10.1167/iovs.15-17587.

Doi et al., Microglia activated with the toll-like receptor 9 ligand CpG attenuate oligomeric amyloid {beta} neurotoxicity in in vitro and in vivo models of Alzheimer's disease. Am J Pathol. Nov. 2009;175(5):2121-32. doi: 10.2353/ajpath.2009.090418.

Faust et al., CpG-depleted adeno-associated virus vectors evade immune detection. J Clin Invest. Jul. 2013;123(7):2994-3001.

Gursel et al., Repetitive elements in mammalian telomeres suppress bacterial DNA-induced immune activation. J Immunol. 2003;171(3):1393-400.

Hartmann et al., Mechanism and function of a newly identified CpG DNA motif in human primary B cells. J Immunol. Jan. 15, 2000;164(2):944-53.

Hensley et al., Toll-like receptors impact on safety and efficacy of gene transfer vectors. Mol Ther. Aug. 2007;15(8): 1417-22. doi: 10.1038/sj.mt.6300217.

Kaminski et al., Synthetic oligodeoxynucleotides containing suppressive TTAGGG motifs inhibit AIM2 inflammasome activation. J Immunol. 2013;191(7):3876-83. doi: 10.4049/jimmunol.1300530. Author Manuscript, 19 pages.

Krieg et al., CpG motifs in bacterial DNA trigger direct B-cell activation. Nature. Apr. 6, 1995;374(6522):546-9.

Krieg, Therapeutic potential of Toll-like receptor 9 activation. Nat Rev. Jun. 2006;5(6):471-84.

Krieg et al., Sequence motifs in adenoviral DNA block immune activation by stimulatory CpG motifs. Proc Natl Acad Sci USA. Oct. 1998;95(21):12631-6.

Kumagai et al., TLR9 as a key receptor for the recognition of DNA. Adv Drug Deliv Rev. Apr. 2008;60(7):795-804. doi: 10.1016/j.addr.2007.12.004.

Latz et al., Ligand-induced conformational changes allosterically activate Toll-like receptor 9. Nat Immunol. Jul. 2007;8(7):772-9.

Lee et al., Nucleic acid-binding polymers as anti-inflammatory agents. Proc Natl Acad Sci U S A. Aug. 23, 2011;108(34):14055-60. doi: 10.1073/pnas. 1105777108. Epub Aug. 15, 2011.

Lenert et al., Targeting Toll-like receptor signaling in plasmacytoid dendritic cells and autoreactive B cells as a therapy for lupus. Arthritis Res Ther. 2006;8(1):203(1-11). doi: 10.1186/ar1888. Epub Jan. 10, 2006.

(56) References Cited

OTHER PUBLICATIONS

Lenert et al., DNAlike class R inhibitory oligonucleotides (INH-ODNs) preferentially block autoantigen-induced B-cell and dendritic cell activation in vitro and autoantibody production in lupus-prone MRL-Fas(lpr/lpr) mice in vivo. Arthritis Res Ther. 2009;11(3):R79. doi: 10.1186/ar2710. Available online http://arthritis-research.com/content/11/3/R79. 16 pages. Epub May 28, 2009.

Lenert et al., Structural characterization of the inhibitory DNA motif for the type A (D)-CpG-induced cytokine secretion and NK-cell lytic activity in mouse spleen cells. DNA Cell Biol. 2003;22(10):621-31. doi: 10.1089/104454903770238094.

Lenert et al., Classification, mechanisms of action, and therapeutic applications of inhibitory oligonucleotides for Toll-like receptors (TLR) 7 and 9. Mediators Inflamm. 2010;2010:986596. 10 pages, doi: 10.1155/2010/986596.

Li et al., A novel antagonist of TLR9 blocking all classes of immunostimulatory CpG-ODNs. Vaccine. 2011;29(11):2193-8. doi: 10.1016/j.vaccine.2010.10.042.

Martino et al., The genome of self-complementary adeno-associated viral vectors increases Toll-like receptor 9-dependent innate immune responses in the liver. Blood. Jun. 16, 2011;117(24):6459-68. Epub Apr. 7, 2011. https:///www.ncbi.nlm.nih.gov/pmc/articles/PMC3123017/?report=printable. 21 pages.

Ohto et al., Structural basis of CpG and inhibitory DNA recognition by Toll-like receptor 9. Nature. Apr. 2015;520(7549):702-5. doi: 10.1038/nature14138.

Olson et al., Microglia initiate central nervous system innate and adaptive immune responses through multiple TLRs. J Immunol. Sep. 15, 2004;173(6):3916-24.

Peter et al., Characterization of suppressive oligodeoxynucleotides that inhibit Toll-like receptor-9-mediated activation of innate immunity. Immunology. 2008;123(1):118-28. doi: 10.1111/j.1365-2567.2007.02718.x.

Rogers et al., Innate immune responses to AAV vectors. Frontiers in Microbiology. Sep. 19, 2011;2(194):1-10.

Shirota et al., Suppressive oligodeoxynucleotides protect mice from lethal endotoxic shock. J Immunol. 2005;174(8):4579-83.

Stunz et al., Inhibitory oligonucleotides specifically block effects of stimulatory CpG oligonucleotides in B cells. Eur J Immunol. 2002;32(5): 1212-22.

Takeda et al., TLR signaling pathways. Semin Immunol. Feb. 2004;16(1):3-9.

Trieu et al., DNA motifs suppressing TLR9 responses. Crit Rev Immunol. 2006;26(6):527-44.

Zhu et al., The TLR9-MyD88 pathway is critical for adaptive immune responses to adeno-associated virus gene therapy vectors in mice. J Clin Invest. Aug. 2009;119(8):2388-98. doi: 10.1172/JCI37607.

U.S. Appl. No. 16/762,356, filed May 7, 2020, Published, 2020-0270637.

U.S. Appl. No. 16/167,764, filed Oct. 23, 2018, Published, 2019-0316151.

PCT/US2018/059756, May 22, 2020, International Preliminary Report on Patentability.

PCT/US2020/032819, Aug. 27, 2020, Invitation to Pay Additional Fees.

PCT/US2020/032819, Oct. 23, 2020, International Search Report and Written Opinion.

EP 17811006.0, Dec. 5, 2019, Extended European Search Report.

International Preliminary Report on Patentability dated May 22, 2020, for Application No. PCT/US2018/059756.

International Search Report and Written Opinion for Application No. PCT/US2020/032819, dated Oct. 23, 2020.

Invitation to Pay Additional Fees for Application No. PCT/US2020/032819, dated Aug. 27, 2020.

[No Author Listed], ODN 2088 control. InvivoGen. Accessed on May 27, 2020. Accessible at www.invivogen.com/odn2088-control. 2 pages.

[No Author Listed], ODN 2088. InvivoGen. Accessed on May 27, 2020. Accessible at www.invivogen.com/odn2088. 2 pages.

[No Author Listed], ODN 4084-F. InvivoGen. Accessed on May 27, 2020. Accessible at www.invivogen.com/odn4084-f. 2 pages.

[No Author Listed], ODN INH-18. InvivoGen. Accessed on May 27, 2020. Accessible at www.invivogen.com/odn-inh18. 2 pages.

[No Author Listed], ODN TTAGGG (A151). InvivoGen. Accessed on May 27, 2020. Accessible at www.invivogen.com/odn2088. 2 pages.

[No Author Listed], ODN TTAGGG control. InvivoGen. Accessed on May 27, 2020. Accessible at www.invivogen.com/odn2088. 2 pages.

Arbuckle et al., The molecular biology of human herpesvirus-6 latency and telomere integration. Microbes Infect. Aug. 2011; 13(8-9):731-41.

Ballas et al., Induction of NK activity in murine and human cells by CpG motifs in oligodeoxynucleotides and bacterial DNA. J Immunol. Sep. 1, 1996;157(5):1840-5.

Chan et al., Engineering adeno-associated viral vectors to evade innate immune and inflammatory responses. Sci Transl Med. Feb. 10, 2021;13(580):eabd3438. doi: 10.1126/scitranslmed.abd3438.

Chen et al., Identification of methylated CpG motifs as inhibitors of the immune stimulatory CpG motifs. Gene Ther. Jul. 2001;8(13):1024-32. doi: 10.1038/sj.gt.3301482.

Duramad et al., Inhibitors of TLR-9 act on multiple cell subsets in mouse and man in vitro and prevent death in vivo from systemic inflammation. J Immunol. May 1, 2005;174(9):5193-200. doi: 10.4049/jimmunol.174.9.5193.

Ho et al., An immunomodulatory GpG oligonucleotide for the treatment of autoimmunity via the innate and adaptive immune systems. J Immunol. 2003;171(9):4920?4926. doi: 10.4049/jimmunol.171.9.4920.

Klinman et al., Contribution of CpG motifs to the immunogenicity of DNA vaccines. J Immunol. Apr. 15, 1997;158(8):3635-9.

Patole et al., G-rich DNA suppresses systemic lupus. J Am Soc Nephrol. Nov. 2005;16(11):3273-80. doi: 10.1681/ASN.2005060658. Epub Sep. 21, 2005.

Sato et al., Immunostimulatory DNA sequences necessary for effective intradermal gene immunization. Science. Jul. 19, 1996;273(5273):352-4. doi: 10.1126/science.273.5273.352.

Shirota et al., Suppressive oligodeoxynucleotides inhibit Th1 differentiation by blocking IFN-gamma- and IL-12-mediated signaling. J Immunol. Oct. 15, 2004;173(8):5002-7. doi: 10.4049/jimmunol.173.8.5002.

Yamamoto et al., DNA from bacteria, but not from vertebrates, induces interferons, activates natural killer cells and inhibits tumor growth. Microbiol Immunol. 1992;36(9):983-97. doi: 10.1111/j.1348-0421.1992.tb02102.x.

Cerullo et al., Toll-like receptor 9 triggers an innate immune response to helper-dependent adenoviral vectors. Mol Ther. Feb. 2007;15(2):378-85.

Huang et al., Targeting the TLR9-MyD88 pathway in the regulation of adaptive immune responses. Expert Opin Ther Targets. Aug. 2010;14(8):787-96. doi: 10.1517/14728222.2010.501333. Review.

Yew et al., Reducing the immunostimulatory activity of CpG-containing plasmid DNA vectors for non-viral gene therapy. Expert Opin Drug Deliv. Nov. 2004;1(1):115-25. Review. Erratum in: Expert Opin Drug Deliv. Jan. 2005;2(1):199.

Sanftner et al., Recombinant AAV-mediated delivery of a tet-inducible reporter gene to the rat retina. Mol Ther. May 2001;3(5 Pt 1):688-96.

* cited by examiner

B cells

|  | GFP+ |
|---|---|
| Mock | 0.14% |
| AAV-eGFP | 2.16% |
| AAV-eGFP-c41 | 4.11% |
| AAV-eGFP-telomere | 3.50% |

Fig. 8A
"c41": 5'-TGGCGCGCACCCACGGCCTG-3'
"telomere": 5'-TTTAGGGTTAGGGTTAGGGTTAGGG-3'
Fig. 8B
scAAV-eGFP:
scAAV-eGFP-3xc41:
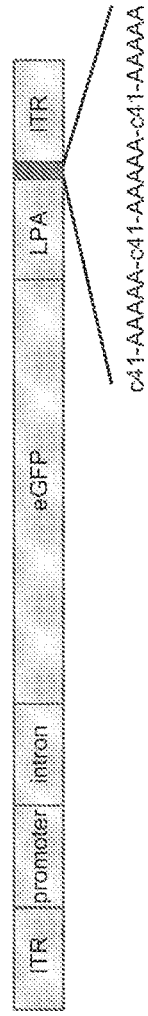
c41-AAAAA-c41-AAAAA-c41-AAAAA
scAAV-eGFP-3xtelomere:
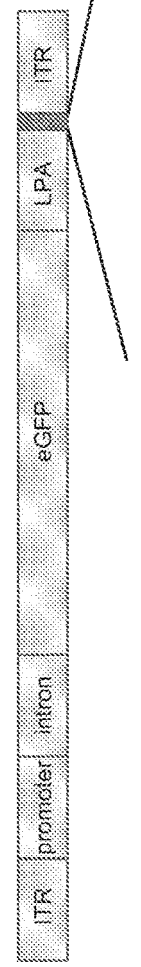
telomere-AAAAA-telomere-AAAAA-telomere-AAAAA
scAAV-3xtelomere-eGFP:
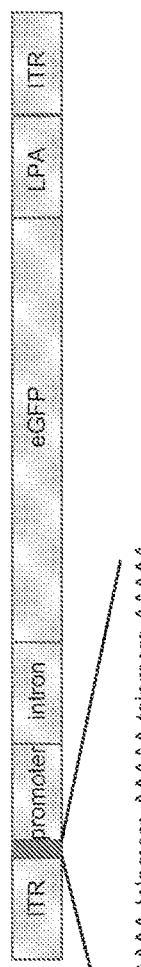
telomere-AAAAA-telomere-AAAAA-telomere-AAAAA

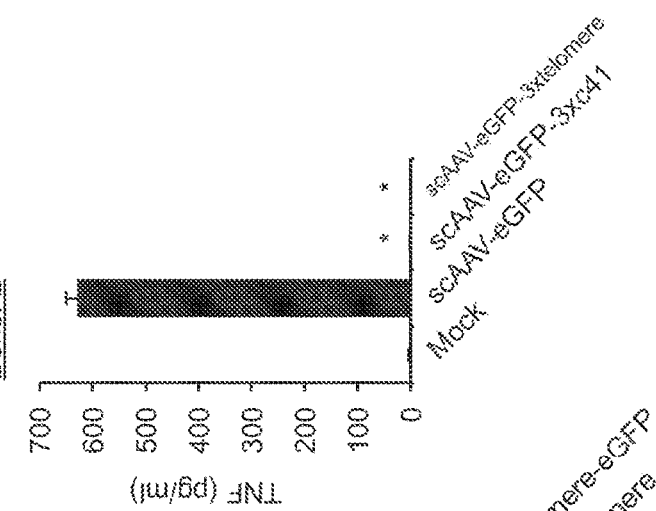
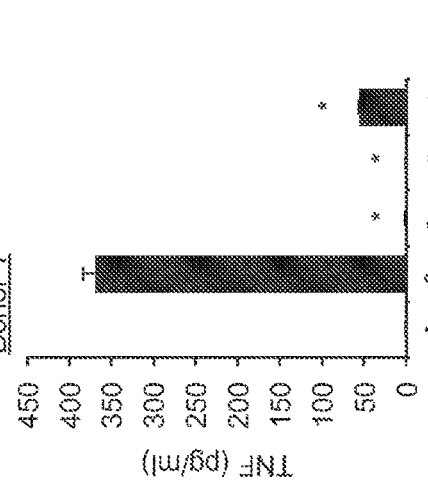
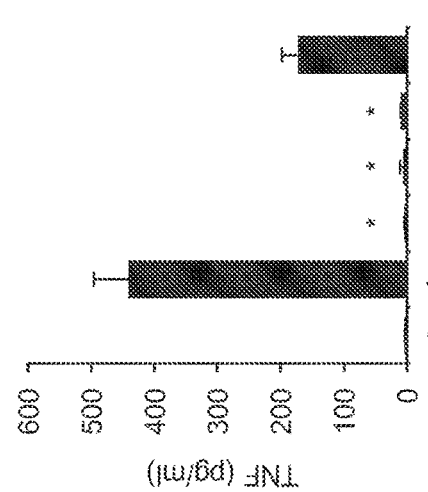

Fig. 10A "control": 5'-GCTAGATGTTAGCGT-3'
Fig. 10B scAAV-eGFP-3xcontrol:
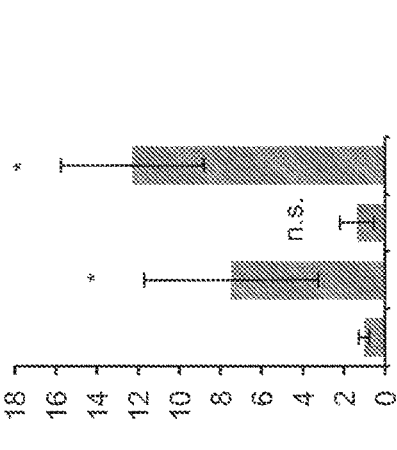
scAAV-eGFP-1xtelomere:
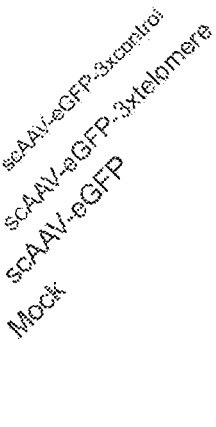
Fig. 10C Primary macrophages
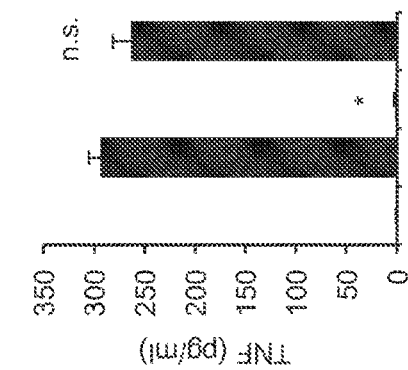
Fig. 10D Primary monocytes
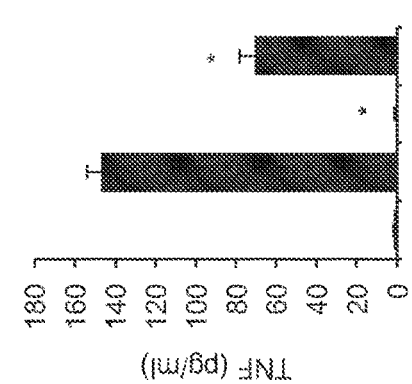
Fig. 10E

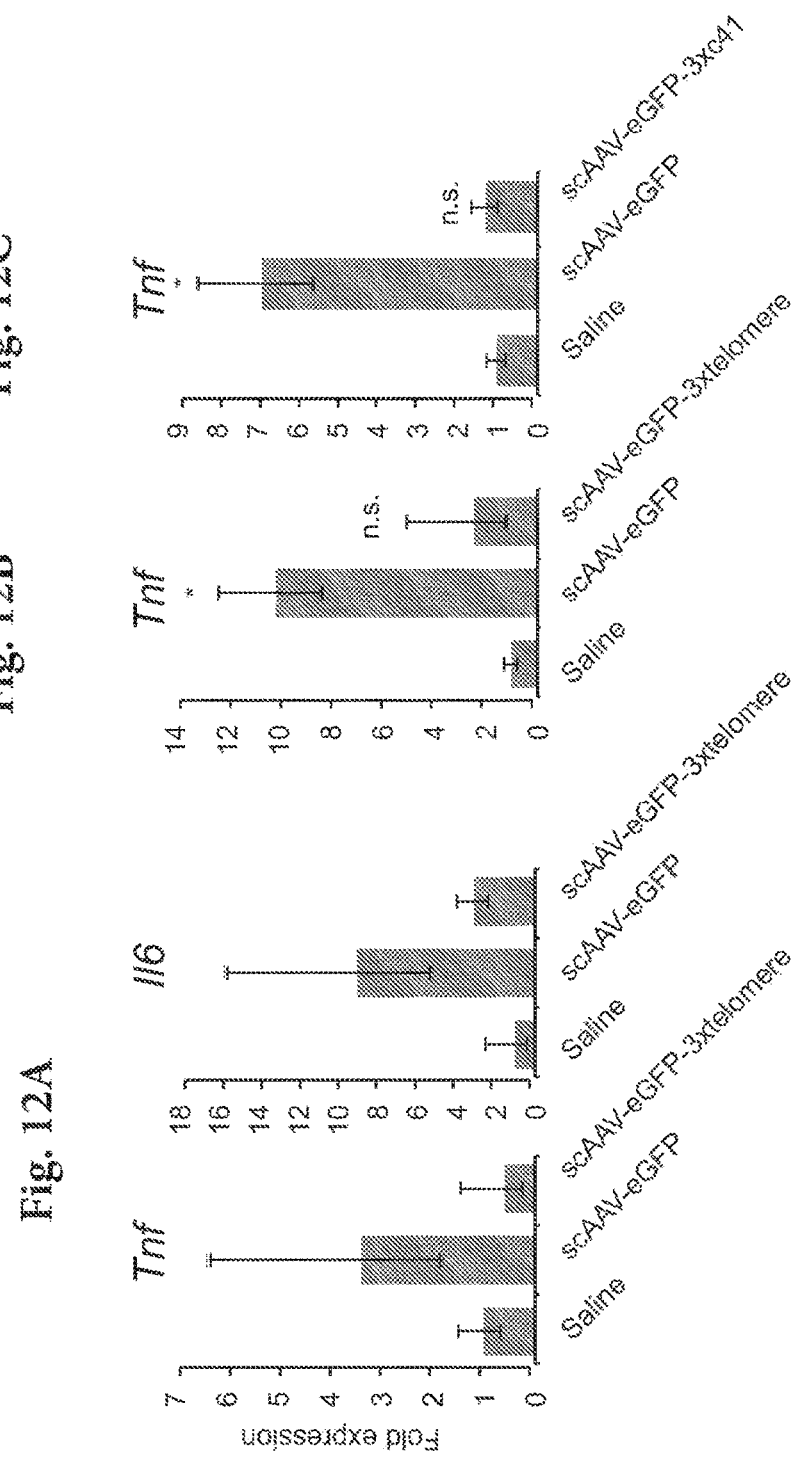

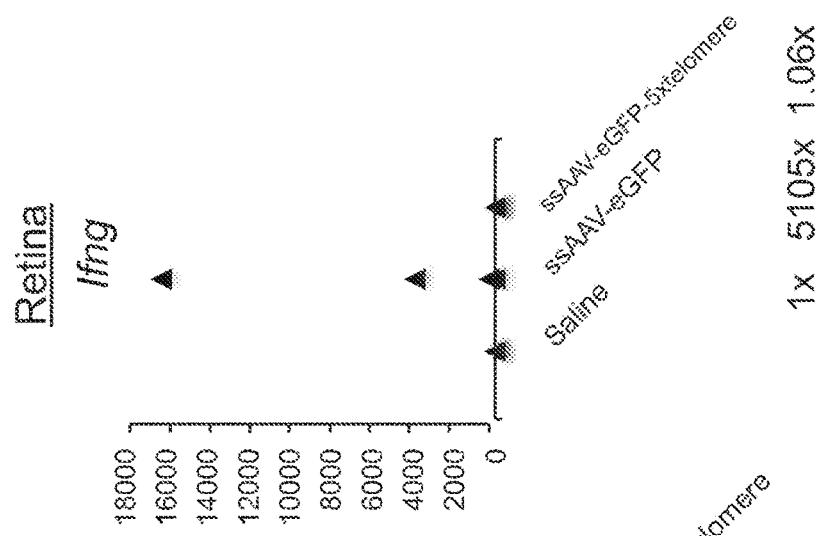
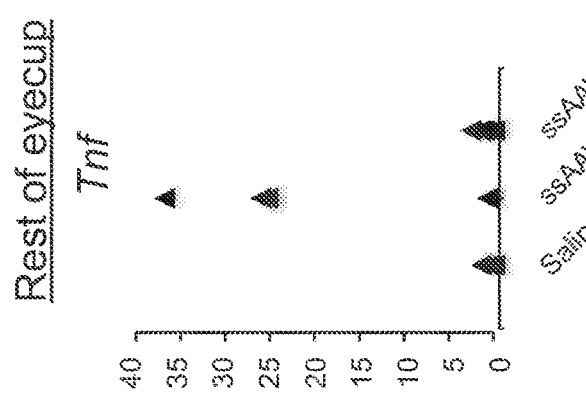
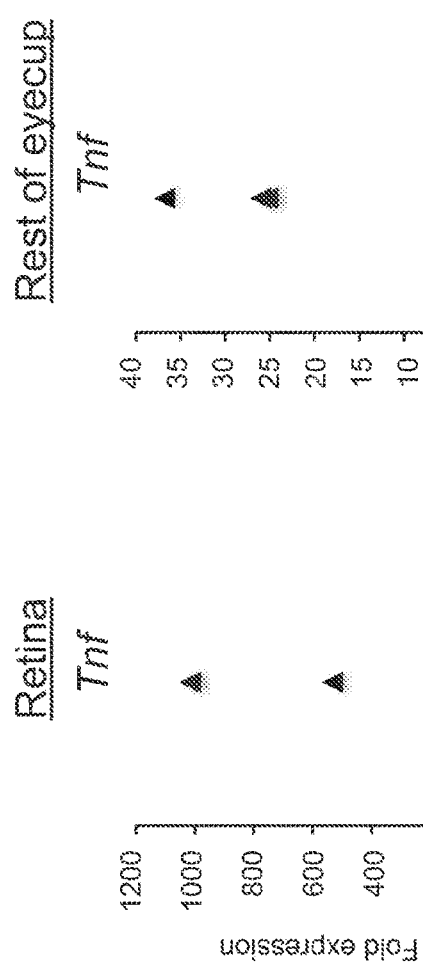

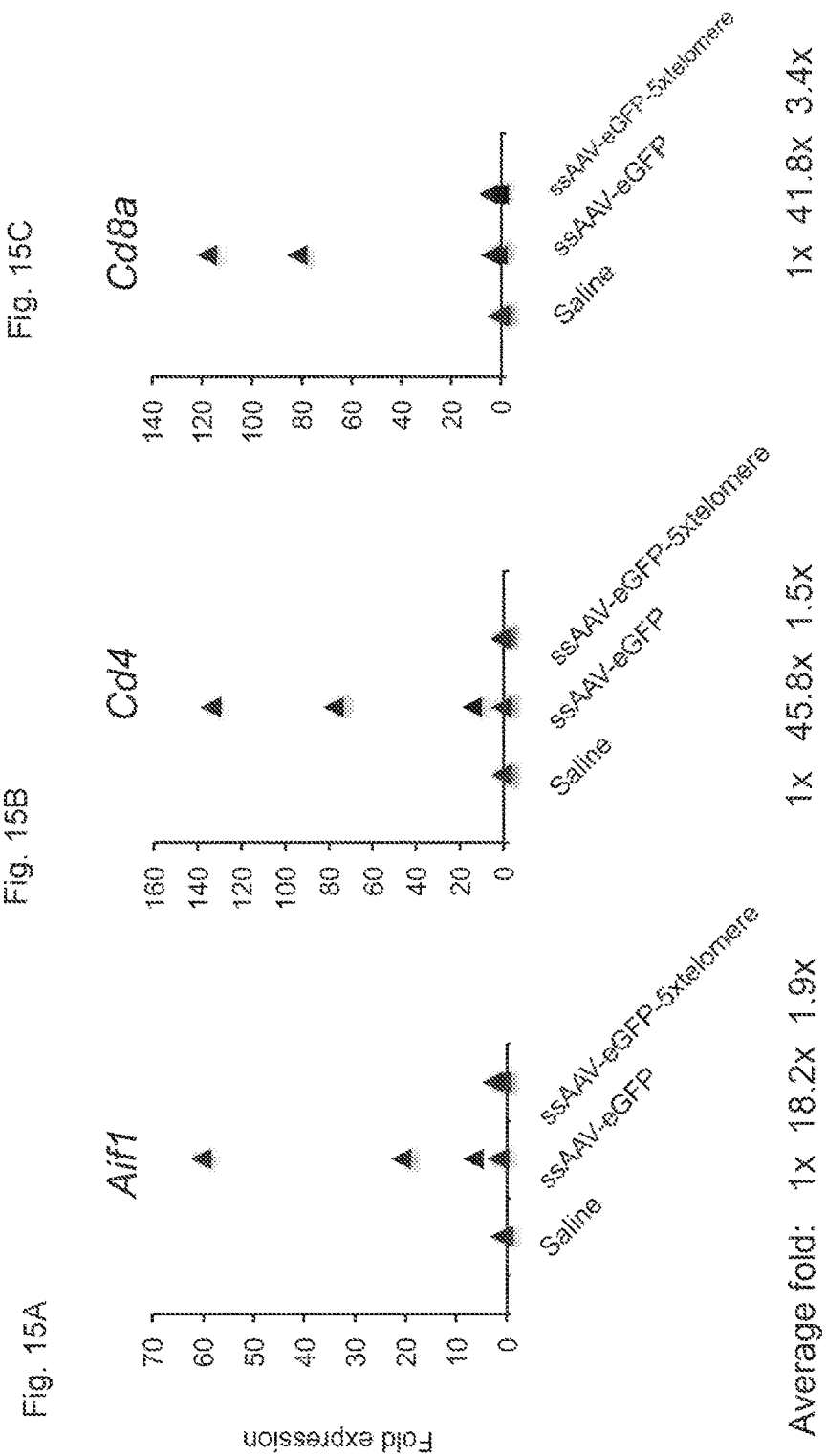

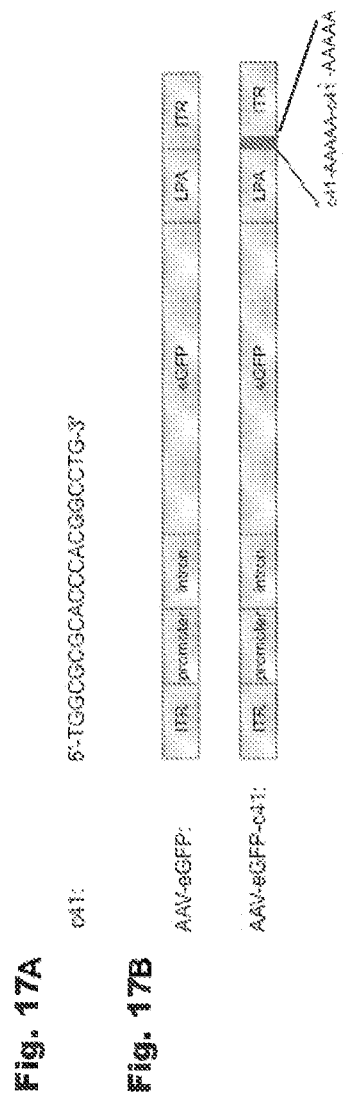

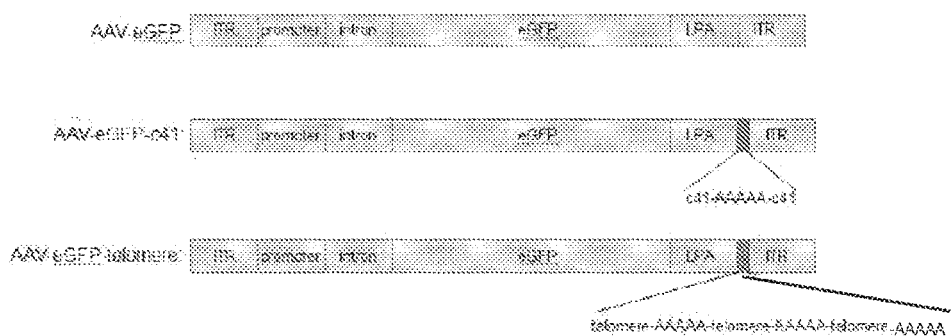

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
tggcgcgcac ccacggcctg                                                      20

<210> SEQ ID NO 2
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 2
tcctggcggg gaagt                                                           15

<210> SEQ ID NO 3
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 3
cctggatggg aa                                                              12

<210> SEQ ID NO 4
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 4
cctggatggg aattcccatc cagg                                                 24

<210> SEQ ID NO 5

```
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 5
cctggatggg aacttaccgc tgca                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 6
ttagggttag ggttagggtt aggg                                              24

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
ctcctattgg gggtttccta t                                                 21

<210> SEQ ID NO 8
<211> LENGTH: 5
<212> TYPE: DNA
<213> ORGANISM: Artificial Sequence
<220> FEATURE:
<223> OTHER INFORMATION: Synthetic Polynucleotide

<400> SEQUENCE: 8 aaaaa                                                                    5

<210> SEQ ID NO 9
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 9
tttagggtta gggttagggt taggg                                             25

<210> SEQ ID NO 10
<211> LENGTH: 4369
<212> TYPE: DNA
<213> ORGANISM: Artificial Sequence
<220> FEATURE:
<223> OTHER INFORMATION: Synthetic Polynucleotide

<400> SEQUENCE: 10
aaagcttccc gggggatct gggccactcc ctctctgcgc gctcgctcgc tcactgaggc         60
cgggcgacca aggtcgccc gacgcccggg ctttgcccgg gcggcctcag tgagcgagcg        120
agcgcgcaga gagggagtgg ccaactccat cactaggggt tcctggaggg gtggagtcgt      180
gacctaggca tatgccaagt acgccccta ttgacgtcaa tgacggtaaa tggcccgcct       240
ggcattatgc ccagtacatg acctatggg actttcctac ttggcagtac atctacgtat      300
tagtcatcgc tattaccatg gtgatgcggt tttggcagta catcaatggg cgtggatagc     360
```

```
ggtttgactc acggggattt ccaagtctcc accccattga cgtcaatggg agtttgtttt      420
ggcaccaaaa tcaacgggac tttccaaaat gtcgtaacaa ctccgcccca ttgacgcaaa      480
tgggcggtag gcgtgtacgg tgggaggtct atataagcag agctcgttta gtgaaccgtc      540
agatcgcctg gagacgccat ccggactcta aggtaaatat aaaatttta agtgtataat       600
gtgttaaact actgattcta attgtttctc tcttttagat tccaacctt ggaactgaat       660
tccgcgggcc cggatccac cggtcgccac catggtgagc aagggcgagg agctgttcac      720
cggggtggtg cccatcctgg tcgagctgga cggcgacgta aacggccaca gttcagcgt      780
gtccggcgag ggcgagggcg atgccaccta cggcaagctg accctgaagt tcatctgcac      840
caccggcaag ctgcccgtgc cctggcccac cctcgtgacc accctgacct acggcgtgca     900
gtgcttcagc cgctacccg accacatgaa gcagcacgac ttcttcaagt ccgccatgcc      960
cgaaggctac gtccaggagc gcaccatctt cttcaaggac gacggcaact acaagacccg     1020
cgccgaggtg aagttcgagg gcgacacccct ggtgaaccgc atcgagctga agggcatcga    1080
cttcaaggag gacggcaaca tcctggggca caagctggag tacaactaca cagccacaa     1140
cgtctatatc atggccgaca gcagaagaa cggcatcaag gtgaacttca agatccgcca     1200
caacatcgag gacggcagcg tgcagctcgc cgaccactac cagcagaaca cccccatcgg    1260
cgacggcccc gtgctgctgc ccgacaacca ctacctgagc acccagtccg ccctgagcaa    1320
agacccaac gagaagcgcg atcacatggt cctgctggag ttcgtgaccg ccgccggaat     1380
cactctcggc atggacgagc tgtacaagta aagcggccgc taggcctcac ctgcgatctc    1440
gatgctttat ttgtgaaatt tgtgatgcta ttgctttatt tgtaaccatt ataagctgca    1500
ataaacaagt taacaacaac aattgcattc attttatgtt tcaggttcag ggggaggtgt    1560
gggaggtttt ttaaactagt ccactccctc tctgcgcgct cgctcgctca ctgaggccgg    1620
gcgaccaaag gtcgcccgac gcccgggctt tgcccgggcg gcctcagtga gcgagcgagc    1680
gcgcagagag ggacagatcc gggcccgcat gcgtcgacaa ttcactggcc gtcgttttac    1740
aacgtcgtga ctgggaaaac cctggcgtta cccaacttaa tcgccttgca gcacatcccc    1800
ctttcgccag ctggcgtaat agcgaagagg cccgcaccga tcgcccttcc caacagttgc    1860
gcagcctgaa tggcgaatgg cgcctgatgc ggtattttct ccttacgcat ctgtgcggta    1920
tttcacaccg catatggtgc actctcagta caatctgctc tgatgccgca tagttaagcc    1980
agccccgaca cccgccaaca cccgctgacg cgccctgacg ggcttgtctg ctcccggcat    2040
ccgcttacag acaagctgtg accgtctccg ggagctgcat gtgtcagagg ttttcaccgt    2100
catcaccgaa acgcgcgaga cgaaagggcc tcgtgatacg cctatttta taggttaatg    2160
tcatgataat aatggtttct tagacgtcag gtggcacttt tcggggaaat gtgcgcggaa    2220
cccctatttg tttatttttc taaatacatt caaatatgta tccgctcatg agacaataac    2280
cctgataaat gcttcaataa tattgaaaaa ggaagagtat gagtattcaa catttccgtg    2340
tcgcccttat tcccttttt gcggcatttt gccttcctgt ttttgctcac ccagaaacgc    2400
tggtgaaagt aaaagatgct gaagatcagt tgggtgcacg agtgggttac atcgaactgg    2460
atctcaacag cggtaagatc cttgagagtt ttcgccccga agaacgtttt ccaatgatga    2520
gcacttttaa agttctgcta tgtggcgcgg tattatcccg tattgacgcc gggcaagagc    2580
aactcggtcg ccgcatacac tattctcaga atgacttggt tgagtactca ccagtcacag    2640
aaaagcatct tacggatggc atgacagtaa gagaattatg cagtgctgcc ataaccatga    2700
```

```
gtgataacac tgcggccaac ttacttctga caacgatcgg aggaccgaag gagctaaccg   2760
cttttttgca caacatgggg gatcatgtaa ctcgccttga tcgttgggaa ccggagctga   2820
atgaagccat accaaacgac gagcgtgaca ccacgatgcc tgtagcaatg gcaacaacgt   2880
tgcgcaaact attaactggc gaactactta ctctagcttc ccggcaacaa ttaatagact   2940
ggatggaggc ggataaagtt gcaggaccac ttctgcgctc ggcccttccg gctggctggt   3000
ttattgctga taaatctgga gccggtgagc gtgggtctcg cggtatcatt gcagcactgg   3060
ggccagatgg taagccctcc cgtatcgtag ttatctacac gacggggagt caggcaacta   3120
tggatgaacg aaatagacag atcgctgaga taggtgcctc actgattaag cattggtaac   3180
tgtcagacca gtttactca tatatacttt agattgattt aaaacttcat ttttaattta    3240
aaaggatcta ggtgaagatc ttttttgata atctcatgac caaatccct taacgtgagt    3300 tttcgttcca ctgagcgtca accccgtag aaaagatcaa aggatcttct tgagatcctt    3360
tttttctgcg cgtaatctgc tgcttgcaaa caaaaaaacc accgctacca gcggtggttt    3420
gtttgccgga tcaagagcta ccaactcttt ttccgaaggt aactggcttc agcagagcgc    3480
agataccaaa tactgttctt ctagtgtagc cgtagttagg ccaccacttc aagaactctg    3540
tagcaccgcc tacatacctc gctctgctaa tcctgttacc agtggctgct gccagtggcg    3600
ataagtcgtg tcttaccggg ttggactcaa gacgatagtt accggataag gcgcagcggt    3660
cgggctgaac ggggggttcg tgcacacagc ccagcttgga gcgaacgacc tacaccgaac    3720
tgagatacct acagcgtgag ctatgagaaa gcgccacgct tcccgaaggg agaaaggcgg    3780
acaggtatcc ggtaagcggc agggtcggaa caggagagcg cacgagggag cttccagggg    3840
gaaacgcctg gtatctttat agtcctgtcg ggtttcgcca cctctgactt gagcgtcgat    3900
ttttgtgatg ctcgtcaggg gggcggagcc tatggaaaaa cgccagcaac gcggcctttt    3960
tacggttcct ggccttttgc tggccttttg ctcacatgtt ctttcctgcg ttatcccctg    4020
attctgtgga taaccgtatt accgcctttg agtgagctga taccgctcgc cgcagccgaa    4080
cgaccgagcg cagcgagtca gtgagcgagg aagcggaaga gcgcccaata cgcaaaccgc    4140
ctctccccgc gcgttggccg attcattaat gcagctggca cgacaggttt cccgactgga    4200
aagcgggcag tgagcgcaac gcaattaatg tgagttagct cactcattag gcaccccagg    4260
ctttacactt tatgcttccg gctcgtatgt tgtgtggaat tgtgagcgga taacaatttc    4320
acacaggaaa cagctatgac catgattacg ccaagctctc gagatctag                4369

<210> SEQ ID NO 11
<211> LENGTH: 4450
<212> TYPE: DNA
<213> ORGANISM: Artificial Sequence
<220> FEATURE:
<223> OTHER INFORMATION: Synthetic Polynucleotide

<400> SEQUENCE: 11
aaagcttccc gggggatct gggccactcc ctctctgcgc gctcgctcgc tcactgaggc       60
cgggcgacca aggtcgccc gacgcccggg ctttgcccgg gcggcctcag tgagcgagcg     120
agcgcgcaga gagggagtgg ccaactccat cactaggggt tcctggaggg gtggagtcgt    180
gacctaggca tatgccaagt acgccccta ttgacgtcaa tgacggtaaa tggcccgcct    240
ggcattatgc ccagtacatg acctatggg actttcctac ttggcagtac atctacgtat    300
tagtcatcgc tattaccatg gtgatgcggt tttggcagta catcaatggg cgtggatagc    360
ggtttgactc acggggattt ccaagtctcc accccattga cgtcaatggg agtttgtttt    420
```

```
ggcaccaaaa tcaacgggac tttccaaaat gtcgtaacaa ctccgcccca ttgacgcaaa      480
tgggcggtag gcgtgtacgg tgggaggtct atataagcag agctcgttta gtgaaccgtc      540
agatcgcctg gagacgccat ccggactcta aggtaaatat aaaattttta agtgtataat      600
gtgttaaact actgattcta attgtttctc tcttttagat tccaacctttt ggaactgaat    660 tccgcgggcc cgggatccac cggtcgccac catggtgagc aagggcgagg agctgttcac      720
cggggtggtg cccatcctgg tcgagctgga cggcgacgta acggccaca agttcagcgt       780 gtccggcgag ggcgagggcg atgccaccta cggcaagctg accctgaagt tcatctgcac      840
caccggcaag ctgcccgtgc cctggcccac cctcgtgacc accctgacct acggcgtgca      900
gtgcttcagc cgctaccccg accacatgaa gcagcacgac ttcttcaagt ccgccatgcc      960
cgaaggctac gtccaggagc gcaccatctt cttcaaggac gacggcaact acaagacccg     1020
cgccgaggtg aagttcgagg gcgacaccct ggtgaaccgc atcgagctga agggcatcga     1080
cttcaaggag gacggcaaca tcctggggca caagctggag tacaactaca acagccacaa     1140
cgtctatatc atggccgaca agcagaagaa cggcatcaag gtgaacttca gatccgcca      1200 caacatcgag gacggcagcg tgcagctcgc cgaccactac cagcagaaca cccccatcgg     1260
cgacggcccc gtgctgctgc ccgacaacca ctacctgagc acccagtccg ccctgagcaa     1320
agaccccaac gagaagcgcg atcacatggt cctgctggag ttcgtgaccg ccgccgggat     1380
cactctcggc atggacgagc tgtacaagta aagcggccgc taggcctcac ctgcgatctc     1440
gatgctttat ttgtgaaatt tgtgatgcta ttgctttatt tgtaaccatt ataagctgca     1500
ataaacaagt taacaacaac aattgcattc attttatgtt tcaggttcag ggggaggtgt     1560
gggaggtttt ttaaatcgat tggcgcgcac ccacggcctg aaaaatggcg cgcacccacg     1620
gcctgaaaaa tggcgcgcac ccacggcctg aaaaaactag tccactccct ctctgcgcgc     1680
tcgctcgctc actgaggccg ggcgaccaaa ggtcgcccga cgcccgggct tgcccgggc     1740 ggcctcagtg agcgagcgag cgcgcagaga gggacagatc cgggcccgca tgcgtcgaca     1800
attcactggc cgtcgtttta caacgtcgtg actgggaaaa ccctggcgtt acccaactta     1860
atcgccttgc agcacatccc cctttcgcca gctggcgtaa tagcgaagag gcccgcaccg     1920
atcgcccttc ccaacagttg cgcagcctga tggcgaatg gcgcctgatg cggtattttc      1980
tccttacgca tctgtgcggt atttcacacc gcatatggtg cactctcagt acaatctgct     2040
ctgatgccgc atagttaagc cagccccgac acccgccaac acccgctgac gcgccctgac     2100
gggcttgtct gctcccggca tccgcttaca gacaagctgt gaccgtctcc gggagctgca     2160
tgtgtcagag gttttcaccg tcatcaccga aacgcgcgag acgaaagggc ctcgtgatac     2220 gcctatttt ataggttaat gtcatgataa taatggtttc ttagacgtca ggtggcactt      2280
ttcggggaaa tgtgcgcgga acccctattt gtttatttt ctaaatacat tcaaatatgt     2340
atccgctcat gagacaataa ccctgataaa tgcttcaata atattgaaaa aggaagagta     2400
tgagtattca acatttccgt gtcgccctta ttcccttttt tgcggcattt tgccttcctg     2460
tttttgctca cccagaaacg ctggtgaaag taaaagatgc tgaagatcag ttgggtgcac     2520
gagtgggtta catcgaactg gatctcaaca gcggtaagat ccttgagagt tttcgccccg     2580
aagaacgttt tccaatgatg agcacttta aagttctgct atgtggcgcg gtattatccc     2640
gtattgacgc cgggcaagag caactcggtc gccgcataca ctattctcag aatgacttgg     2700
ttgagtactc accagtcaca gaaaagcatc ttacggatgg catgacagta agagaattat     2760
```

| | |
|---|---:|
| gcagtgctgc cataaccatg agtgataaca ctgcggccaa cttacttctg acaacgatcg | 2820 |
| gaggaccgaa ggagctaacc gcttttttgc acaacatggg ggatcatgta actcgccttg | 2880 |
| atcgttggga accggagctg aatgaagcca taccaaacga cgagcgtgac accacgatgc | 2940 |
| ctgtagcaat ggcaacaacg ttgcgcaaac tattaactgg cgaactactt actctagctt | 3000 |
| cccggcaaca attaatagac tggatggagg cggataaagt tgcaggacca cttctgcgct | 3060 |
| cggcccttcc ggctggctgg tttattgctg ataaatctgg agccggtgag cgtgggtctc | 3120 |
| gcggtatcat tgcagcactg gggccagatg gtaagccctc ccgtatcgta gttatctaca | 3180 |
| cgacggggag tcaggcaact atggatgaac gaaatagaca gatcgctgag ataggtgcct | 3240 |
| cactgattaa gcattggtaa ctgtcagacc aagtttactc atatatactt tagattgatt | 3300 |
| taaaacttca ttttttaattt aaaaggatct aggtgaagat cctttttgat aatctcatga | 3360 |
| ccaaaatccc ttaacgtgag ttttcgttcc actgagcgtc agaccccgta gaaaagatca | 3420 |
| aaggatcttc ttgagatcct ttttttctgc gcgtaatctg ctgcttgcaa acaaaaaaac | 3480 |
| caccgctacc agcggtggtt tgtttgccgg atcaagagct accaactctt tttccgaagg | 3540 |
| taactggctt cagcagagcg cagataccaa atactgttct tctagtgtag ccgtagttag | 3600 |
| gccaccactt caagaactct gtagcaccgc ctacatacct cgctctgcta atcctgttac | 3660 |
| cagtggctgc tgccagtggc gataagtcgt gtcttaccgg gttggactca agacgatagt | 3720 |
| taccggataa ggcgcagcgg tcgggctgaa cggggggttc gtgcacacag cccagcttgg | 3780 |
| agcgaacgac ctacaccgaa ctgagatacc tacagcgtga gctatgagaa agcgccacgc | 3840 |
| ttcccgaagg gagaaaggcg gacaggtatc cggtaagcgg cagggtcgga acaggagagc | 3900 |
| gcacgaggga gcttccaggg ggaaacgcct ggtatcttta tagtcctgtc gggtttcgcc | 3960 |
| acctctgact tgagcgtcga tttttgtgat gctcgtcagg ggggcggagc ctatggaaaa | 4020 |
| acgccagcaa cgcggccttt ttacggttcc tggccttttg ctggcctttt gctcacatgt | 4080 |
| tctttcctgc gttatcccct gattctgtgg ataaccgtat taccgccttt gagtgagctg | 4140 |
| ataccgctcg ccgcagccga acgaccgagc gcagcgagtc agtgagcgag gaagcggaag | 4200 |
| agcgcccaat acgcaaaccg cctctccccg cgcgttggcc gattcattaa tgcagctggc | 4260 |
| acgacaggtt tcccgactgg aaagcgggca gtgagcgcaa cgcaattaat gtgagttagc | 4320 |
| tcactcatta ggcaccccag gctttacact ttatgcttcc ggctcgtatg ttgtgtggaa | 4380 |
| ttgtgagcgg ataacaattt cacacaggaa acagctatga ccatgattac gccaagctct | 4440 |
| cgagatctag | 4450 |

<210> SEQ ID NO 12
<211> LENGTH: 4465
<212> TYPE: DNA
<213> ORGANISM: Artificial Sequence
<220> FEATURE:
<223> OTHER INFORMATION: Synthetic Polynucleotide

<400> SEQUENCE: 12

| | |
|---|---:|
| aaagcttccc gggggggatct gggccactcc ctctctgcgc gctcgctcgc tcactgaggc | 60 |
| cgggcgacca aagtcgcccc gacgcccggg ctttgcccgg gcggcctcag tgagcgagcg | 120 |
| agcgcgcaga gagggagtgg ccaactccat cactaggggt tcctggaggg gtggagtcgt | 180 |
| gacctaggca tatgccaagt acgccccccta ttgacgtcaa tgacggtaaa tggcccgcct | 240 |
| ggcattatgc ccagtacatg acctatggga ctttcctac ttggcagtac atctacgtat | 300 |
| tagtcatcgc tattaccatg gtgatgcggt tttggcagta catcaatggg cgtggatagc | 360 |

```
ggtttgactc acggggattt ccaagtctcc accccattga cgtcaatggg agtttgtttt      420
ggcaccaaaa tcaacgggac tttccaaaat gtcgtaacaa ctccgcccca ttgacgcaaa      480
tgggcggtag gcgtgtacgg tgggaggtct atataagcag agctcgttta gtgaaccgtc      540
agatcgcctg gagacgccat ccggactcta aggtaaatat aaaattttta agtgtataat      600
gtgttaaact actgattcta attgtttctc tcttttagat tccaacctt ggaactgaat       660 tccgcgggcc cgggatccac cggtcgccac catggtgagc aagggcgagg agctgttcac      720
cggggtggtg cccatcctgg tcgagctgga cggcgacgta aacggccaca agttcagcgt      780
gtccggcgag ggcgagggcg atgccaccta cggcaagctg accctgaagt tcatctgcac      840
caccggcaag ctgcccgtgc cctggcccac cctcgtgacc accctgacct acggcgtgca      900
gtgcttcagc cgctacccog accacatgaa gcagcacgac ttcttcaagt ccgccatgcc      960
cgaaggctac gtccaggagc gcaccatctt cttcaaggac gacggcaact acaagacccg     1020
cgccgaggtg aagttcgagg gcgacaccct ggtgaaccgc atcgagctga agggcatcga     1080
cttcaaggag gacggcaaca tcctggggca caagctggag tacaactaca acagccacaa     1140
cgtctatatc atggccgaca gcagaagaa cggcatcaag gtgaacttca agatccgcca      1200
caacatcgag gacggcagcg tgcagctcgc cgaccactac cagcagaaca cccccatcgg     1260
cgacggcccc gtgctgctgc ccgacaacca ctacctgagc acccagtccg ccctgagcaa     1320 agacccccaac gagaagcgcg atcacatggt cctgctggag ttcgtgaccg ccgccgggat    1380
cactctcggc atggacgagc tgtacaagta aagcggccgc taggcctcac ctgcgatctc     1440
gatgctttat ttgtgaaatt tgtgatgcta ttgctttatt tgtaaccatt ataagctgca     1500
ataaacaagt taacaacaac aattgcattc attttatgtt tcaggttcag ggggaggtgt     1560
gggaggtttt ttaaatcgat tttagggtta gggttagggt tagggaaaaa tttagggtta     1620
gggttagggt tagggaaaaa tttagggtta gggttagggt tagggaaaaa actagtccac     1680
tccctctctg cgcgctcgct cgctcactga ggccgggcga ccaaaggtcg cccgacgccc     1740
gggctttgcc cgggcggcct cagtgagcga gcgagcgcgc agagagggac agatccgggc     1800
ccgcatgcgt cgacaattca ctggccgtcg ttttacaacg tcgtgactgg gaaaaccctg     1860
gcgttaccca acttaatcgc cttgcagcac atccccecttt cgccagctgg cgtaatagcg     1920
aagaggcccg caccgatcgc ccttcccaac agttgcgcag cctgaatggc gaatggcgcc     1980
tgatgcggta ttttctcctt acgcatctgt gcggtatttc acaccgcata tggtgcactc     2040
tcagtacaat ctgctctgat gccgcatagt taagccagcc ccgacacccg ccaacacccg     2100
ctgacgcgcc ctgacgggct tgtctgctcc cggcatccgc ttacagacaa gctgtgaccg     2160
tctccgggag ctgcatgtgt cagaggtttt caccgtcatc accgaaacgc gcgagacgaa     2220
agggcctcgt gatacgccta ttttatagg ttaatgtcat gataataatg gtttcttaga     2280
cgtcaggtgg cacttttcgg ggaaatgtgc gcggaacccc tatttgttta ttttcctaaa     2340
tacattcaaa tatgtatccg ctcatgagac aataaccctg ataaatgctt caataatatt     2400
gaaaaaggaa gagtatgagt attcaacatt tccgtgtcgc ccttattccc ttttttgcgg     2460
cattttgcct tcctgttttt gctcacccag aaacgctggt gaaagtaaaa gatgctgaag     2520
atcagttggg tgcacgagtg ggttacatcg aactggatct caacagcggt aagatccttg     2580
agagttttcg ccccgaagaa cgttttccaa tgatgagcac ttttaaagtt ctgctatgtg     2640
gcgcggtatt atcccgtatt gacgccgggc aagagcaact cggtcgccgc atacactatt     2700
```

```
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atgggggatc    2880
atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct gcgctcggcc cttccggctg gctggtttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
ccgtagaaaa gatcaaagga tcttcttgag atcctttttt tctgcgcgta atctgctgct    3480
tgcaaacaaa aaaaccaccg ctaccagcgg tggtttgttt gccggatcaa gagctaccaa    3540 ctcttttttcc gaaggtaact ggcttcagca gagcgcagat accaaatact gttcttctag    3600
tgtagccgta gttaggccac cacttcaaga actctgtagc accgcctaca tacctcgctc    3660
tgctaatcct gttaccagtg gctgctgcca gtggcgataa gtcgtgtctt accgggttgg    3720
actcaagacg atagttaccg gataaggcgc agcggtcggg ctgaacgggg gttcgtgca    3780 cacagcccag cttggagcga acgacctaca ccgaactgag atacctacag cgtgagctat    3840
gagaaagcgc cacgcttccc gaagggagaa aggcggacag gtatccggta agcggcaggg    3900
tcggaacagg agagcgcacg agggagcttc caggggggaaa cgcctggtat ctttatagtc    3960
ctgtcgggtt tcgccacctc tgacttgagc gtcgattttt gtgatgctcg tcagggggc    4020 ggagcctatg gaaaaacgcc agcaacgcgg cctttttacg gttcctggcc ttttgctggc    4080
cttttgctca catgttcttt cctgcgttat cccctgattc tgtggataac cgtattaccg    4140
cctttgagtg agctgatacc gctcgccgca gccgaacgac cgagcgcagc gagtcagtga    4200
gcgaggaagc ggaagagcgc ccaatacgca aaccgcctct ccccgcgcgt tggccgattc    4260
attaatgcag ctggcacgac aggtttcccg actggaaagc gggcagtgag cgcaacgcaa    4320
ttaatgtgag ttagctcact cattaggcac cccaggcttt acactttatg cttccggctc    4380
gtatgttgtg tggaattgtg agcggataac aatttcacac aggaaacagc tatgaccatg    4440
attacgccaa gctctcgaga tctag                                         4465
```

<210> SEQ ID NO 13
<211> LENGTH: 4465
<212> TYPE: DNA
<213> ORGANISM: Artificial Sequence
<220> FEATURE:
<223> OTHER INFORMATION: Synthetic Polynucleotide

<400> SEQUENCE: 13

```
aaagcttccc ggggggatct gggccactcc ctctctgcgc gctcgctcgc tcactgaggc     60
cgggcgacca aggtcgcccc gacgcccggg ctttgcccgg gcggcctcag tgagcgagcg    120
agcgcgcaga gagggagtgg ccaactccat cactagggt tcctggaggg gtggagtcgt    180
gacctaggtt tagggttagg gttagggtta gggaaaaatt tagggttagg gttagggtta    240
gggaaaaatt tagggttagg gttagggtta gggaaaaacc taggcatatg ccaagtacgc    300
```

```
cccctattga cgtcaatgac ggtaaatggc ccgcctggca ttatgcccag tacatgacct    360
tatgggactt tcctacttgg cagtacatct acgtattagt catcgctatt accatggtga    420
tgcggttttg gcagtacatc aatgggcgtg gatagcggtt tgactcacgg ggatttccaa    480
gtctccaccc cattgacgtc aatgggagtt tgttttggca ccaaaatcaa cgggactttc    540
caaaatgtcg taacaactcc gccccattga cgcaaatggg cggtaggcgt gtacggtggg    600
aggtctatat aagcagagct cgtttagtga accgtcagat cgcctggaga cgccatccgg    660
actctaaggt aaatataaaa ttttttaagtg tataatgtgt taaactactg attctaattg    720
tttctctctt ttagattcca acctttggaa ctgaattccg cggccccggg atccaccggt    780
cgccaccatg gtgagcaagg gcgaggagct gttcaccggg gtggtgccca tcctggtcga    840
gctggacggc gacgtaaacg gccacaagtt cagcgtgtcc ggcgagggcg agggcgatgc    900
cacctacggc aagctgaccc tgaagttcat ctgcaccacc ggcaagctgc ccgtgccctg    960
gcccaccctc gtgaccaccc tgacctacgg cgtgcagtgc ttcagccgct accccgacca   1020
catgaagcag cacgacttct tcaagtccgc catgcccgaa ggctacgtcc aggagcgcac   1080
catcttcttc aaggacgacg gcaactacaa gacccgcgcc gaggtgaagt tcgagggcga   1140
caccctggtg aaccgcatcg agctgaaggg catcgacttc aaggaggacg gcaacatcct   1200
ggggcacaag ctggagtaca actacaacag ccacaacgtc tatatcatgg ccgacaagca   1260
gaagaacggc atcaaggtga acttcaagat ccgccacaac atcgaggacg gcagcgtgca   1320
gctcgccgac cactaccagc agaacacccc catcggcgac ggccccgtgc tgctgcccga   1380
caaccactac ctgagcaccc agtccgccct gagcaaagac cccaacgaga gcgcgatca   1440 catggtcctg ctggagttcg tgaccgccgc cgggatcact ctcggcatgg acgagctgta   1500
caagtaaagc ggccgctagg cctcacctgc gatctcgatg ctttatttgt gaaatttgtg   1560
atgctattgc tttatttgta accattataa gctgcaataa acaagttaac aacaacaatt   1620
gcattcattt tatgtttcag gttcagggggg aggtgtggga ggttttttaa actagtccac   1680
tccctctctg cgcgctcgct cgctcactga ggccgggcga ccaaaggtcg cccgacgccc   1740
gggctttgcc cgggcggcct cagtgagcga gcgagcgcgc agagagggac agatccgggc   1800
ccgcatgcgt cgacaattca ctggccgtcg ttttacaacg tcgtgactgg gaaaaccctg   1860
gcgttaccca acttaatcgc cttgcagcac atccccctt cgccagctgg cgtaatagcg   1920
aagaggcccg caccgatcgc ccttcccaac agttgcgcag cctgaatggc gaatggcgcc   1980
tgatgcggta ttttctcctt acgcatctgt gcggtatttc acaccgcata tggtgcactc   2040
tcagtacaat ctgctctgat gccgcatagt taagccagcc ccgacacccg ccaacacccg   2100
ctgacgcgcc ctgacgggct tgtctgctcc cggcatccgc ttacagacaa gctgtgaccg   2160
tctccgggag ctgcatgtgt cagaggtttt caccgtcatc accgaaacgc gcgagacgaa   2220
agggcctcgt gatacgccta tttttatagg ttaatgtcat gataataatg gtttcttaga   2280
cgtcaggtgg cacttttcgg ggaaatgtgc gcggaacccc tatttgttta ttttctaaa   2340 tacattcaaa tatgtatccg ctcatgagac aataaccctg ataaatgctt caataatatt   2400
gaaaaaggaa gagtatgagt attcaacatt tccgtgtcgc ccttattccc ttttttgcgg   2460
cattttgcct tcctgttttt gctcacccag aaacgctggt gaaagtaaaa gatgctgaag   2520
atcagttggg tgcacgagtg ggttacatcg aactggatct caacagcggt aagatccttg   2580
agagttttcg ccccgaagaa cgttttccaa tgatgagcac ttttaaagtt ctgctatgtg   2640
```

```
gcgcggtatt atcccgtatt gacgccgggc aagagcaact cggtcgccgc atacactatt    2700
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atggggggatc    2880 atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct cgcgtcggcc cttccggctg gctggtttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
ccgtagaaaa gatcaaagga tcttcttgag atcctttttt tctgcgcgta atctgctgct    3480
tgcaaacaaa aaaaccaccg ctaccagcgg tggtttgttt gccggatcaa gagctaccaa    3540 ctcttttttcc gaaggtaact ggcttcagca gagcgcagat accaaatact gttcttctag    3600
tgtagccgta gttaggccac cacttcaaga actctgtagc accgcctaca tacctcgctc    3660
tgctaatcct gttaccagtg gctgctgcca gtggcgataa gtcgtgtctt accgggttgg    3720
actcaagacg atagttaccg gataaggcgc agcggtcggg ctgaacgggg gttcgtgca    3780 cacagcccag cttggagcga acgacctaca ccgaactgag atacctacag cgtgagctat    3840
gagaaagcgc cacgcttccc gaagggagaa aggcggacag gtatccggta agcggcaggg    3900
tcggaacagg agagcgcacg agggagcttc caggggaaa cgcctggtat ctttatagtc    3960
ctgtcgggtt tcgccacctc tgacttgagc gtcgatttt gtgatgctcg tcaggggggc    4020
ggagcctatg gaaaaacgcc agcaacgcgg ccttttacg gttcctggcc ttttgctggc    4080
cttttgctca catgttcttt cctgcgttat cccctgattc tgtggataac cgtattaccg    4140
cctttgagtg agctgatacc gctcgccgca gccgaacgac cgagcgcagc gagtcagtga    4200
gcgaggaagc ggaagagcgc ccaatacgca aaccgcctct ccccgcgcgt tggccgattc    4260
attaatgcag ctggcacgac aggtttcccg actggaaagc gggcagtgag cgcaacgcaa    4320
ttaatgtgag ttagctcact cattaggcac cccaggcttt acactttatg cttccggctc    4380
gtatgttgtg tggaattgtg agcggataac aatttcacac aggaaacagc tatgaccatg    4440
attacgccaa gctctcgaga tctag                                          4465
```

<210> SEQ ID NO 14
<211> LENGTH: 6940
<212> TYPE: DNA
<213> ORGANISM: Artificial Sequence
<220> FEATURE:
<223> OTHER INFORMATION: Synthetic Polynucleotide

<400> SEQUENCE: 14

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagcg gcctcggcct ctgcataaat aaaaaaaatt agtcagccat gagcttggcc     240
```

```
cattgcatac gttgtatcca tatcataata tgtacattta tattggctca tgtccaacat    300
taccgccatg ttgacattga ttattgacta gttattaata gtaatcaatt acggggtcat    360
tagttcatag cccatatatg gagttccgcg ttacataact tacggtaaat ggcccgcctg    420
gctgaccgcc caacgacccc cgcccattga cgtcaataat gacgtatgtt cccatagtaa    480
cgccaatagg gactttccat tgacgtcaat gggtggagta tttacggtaa actgcccact    540
tggcagtaca tcaagtgtat catatgccaa gtacgccccc tattgacgtc aatgacggta    600
aatggcccgc ctggcattat gcccagtaca tgaccttatg ggactttcct acttggcagt    660
acatctacgt attagtcatc gctattacca tggtgatgcg gttttggcag tacatcaatg    720
ggcgtggata gcggtttgac tcacggggat ttccaagtct ccaccccatt gacgtcaatg    780
ggagtttgtt ttggcaccaa aatcaacggg actttccaaa atgtcgtaac aactccgccc    840
cattgacgca aatgggcggt aggcgtgtac ggtgggaggt ctatataagc agagctcgtt    900
tagtgaaccg tcagatcgcc tggagacgcc atccacgctg ttttgacctc catagaagac    960
accgggaccg atccagcctc ccctcgaagc tgatcctgag aacttcaggg tgagtctatg   1020
ggacccttga tgttttcttt cccttcttt tctatggtta agttcatgtc ataggaaggg   1080
gagaagtaac agggtacaca tattgaccaa atcagggtaa ttttgcattt gtaattttaa   1140
aaaatgcttt cttcttttaa tatactttt tgtttatctt atttctaata ctttccctaa   1200
tctctttctt tcagggcaat aatgatacaa tgtatcatgc ctctttgcac cattctaaag   1260
aataacagtg ataatttctg ggttaaggca atagcaatat ttctgcatat aaatatttct   1320
gcatataaat tgtaactgat gtaagaggtt tcatattgct aatagcagct acaatccagc   1380
taccattctg ctttttatttt atggttggga taaggctgga ttattctgag tccaagctag   1440
gcccttttgc taatcatgtt catacctctt atcttcctcc cacagctcct gggcaacgtg   1500
ctggtctgtg tgctggccca tcactttggc aaagaattcc gcgggccgg gatccaccgg   1560 tcgccaccat ggtgagcaag ggcgaggagc tgttcaccgg ggtggtgccc atcctggtcg   1620
agctggacgg cgacgtaaac ggccacaagt tcagcgtgtc cggcgagggc gagggcgatg   1680
ccacctacgg caagctgacc ctgaagttca tctgcaccac cggcaagctg cccgtgccct   1740
ggcccaccct cgtgaccacc ctgacctacg gcgtgcagtg cttcagccgc taccccgacc   1800
acatgaagca gcacgacttc ttcaagtccg ccatgcccga aggctacgtc caggagcgca   1860
ccatcttctt caaggacgac ggcaactaca agacccgcgc cgaggtgaag ttcgagggcg   1920
acaccctggt gaaccgcatc gagctgaagg gcatcgactt caaggaggac ggcaacatcc   1980
tggggcacaa gctggagtac aactacaaca gccacaacgt ctatatcatg gccgacaagc   2040
agaagaacgg catcaaggtg aacttcaaga tccgccacaa catcgaggac ggcagcgtgc   2100
agctcgccga ccactaccag cagaacaccc ccatcggcga cggccccgtg ctgctgcccg   2160
acaaccacta cctgagcacc cagtccgccc tgagcaaaga ccccaacgag aagcgcgatc   2220
acatggtcct gctggagttc gtgaccgccg ccgggatcac tctcggcatg gacgagctgt   2280
acaagtaaag cggccgctct agaggatcca agcttatcga taccgtcgac ctcgagggcc   2340
cagatctaat tcaccccacc agtgcaggct gcctatcaga aagtggtggc tggtgtggct   2400
aatgccctgg cccacaagta tcactaagct cgctttcttg ctgtccaatt tctattaaag   2460
gttcctttgt tccctaagtc caactactaa actgggggat attatgaagg gccttgagca   2520
tctggattct gcctaataaa aaacatttat tttcattgca atgatgtatt taaattattt   2580
```

```
ctgaatattt tactaaaaag ggaatgtggg aggtcagtgc atttaaaaca taaagaaatg    2640
aagagctagt tcaaaccttg ggaaaataca ctatatctta aactccatga aagaaggtga    2700
ggctgcaaac agctaatgca cattggcaac agcccctgat gcctatgcct tattcatccc    2760
tcagaaaagg attcaagtag aggcttgatt tggaggttaa agttttgcta tgctgtattt    2820
tacattactt attgttttag ctgtcctcat gaatgtcttt tcactaccca tttgcttatc    2880
ctgcatctct cagccttgac tccactcagt tctcttgctt agagatacca cctttcccct    2940
gaagtgttcc ttccatgttt tacggcgaga tggtttctcc tcgcctggcc actcagcctt    3000
agttgtctct gttgtcttat agaggtctac ttgaagaagg aaaaacaggg ggcatggttt    3060
gactgtcctg tgagcccttc ttccctgcct cccccactca cagtgacccg gaatccctcg    3120
acatctagag catggctacg tagataagta gcatggcggg ttaatcatta actacaagga    3180 accccctagtg atggagttgg ccactccctc tctgcgcgct cgctcgctca ctgaggccgg    3240
gcgaccaaag gtcgcccgac gcccgggctt tgcccgggcg gcctcagtga gcgagcgagc    3300
gcgccagctg gcgtaatagc gaagaggccc gcaccgatcg cccttcccaa cagttgcgca    3360
gcctgaatgg cgaatggaat tccagacgat tgagcgtcaa aatgtaggta tttccatgag    3420 cgttttcct gttgcaatgg ctggcggtaa tattgttctg gatattacca gcaaggccga    3480
tagtttgagt tcttctactc aggcaagtga tgttattact aatcaaagaa gtattgcgac    3540
aacggttaat ttgcgtgatg gacagactct tttactcggt ggcctcactg attataaaaa    3600
cacttctcag gattctggcg taccgttcct gtctaaaatc cctttaatcg gcctcctgtt    3660
tagctcccgc tctgattcta acgaggaaag cacgttatac gtgctcgtca aagcaaccat    3720
agtacgcgcc ctgtagcggc gcattaagcg cggcgggtgt ggtggttacg cgcagcgtga    3780
ccgctacact tgccagcgcc ctagcgcccg ctcctttcgc tttcttccct tcctttctcg    3840
ccacgttcgc cggctttccc cgtcaagctc taaatcgggg gctcccttta gggttccgat    3900
ttagtgcttt acggcacctc gaccccaaaa aacttgatta gggtgatggt tcacgtagtg    3960
ggccatcgcc ctgatagacg gttttttcgcc ctttgacgtt ggagtccacg ttctttaata    4020
gtggactctt gttccaaact ggaacaacac tcaaccctat ctcggtctat tcttttgatt    4080
tataagggat tttgccgatt tcggcctatt ggttaaaaaa tgagctgatt taacaaaaat    4140
ttaacgcgaa ttttaacaaa atattaacgt ttacaattta aatatttgct tatacaatct    4200
tcctgttttt ggggcttttc tgattatcaa ccggggtaca tatgattgac atgctagttt    4260
tacgattacc gttcatcgat tctcttgttt gctccagact ctcaggcaat gacctgatag    4320
cctttgtaga gacctctcaa aaatagctac cctctccggc atgaatttat cagctagaac    4380
ggttgaatat catattgatg gtgatttgac tgtctccggc cttctcacc cgtttgaatc    4440 tttacctaca cattactcag gcattgcatt taaaatatat gagggttcta aaattttta    4500 tccttgcgtt gaaataaagg cttctcccgc aaaagtatta cagggtcata atgtttttgg    4560
tacaaccgat ttagctttat gctctgaggc tttattgctt aattttgcta attctttgcc    4620
ttgcctgtat gatttattgg atgttggaat tcctgatgcg gtattttctc cttacgcatc    4680
tgtgcggtat ttcacaccgc atatggtgca ctctcagtac aatctgctct gatgccgcat    4740
agttaagcca gccccgacac ccgccaacac ccgctgacgc gccctgacgg gcttgtctgc    4800
tcccggcatc cgcttacaga caagctgtga ccgtctccgg gagctgcatg tgtcagaggt    4860
tttcaccgtc atcaccgaaa cgcgcgagac gaaagggcct cgtgatacgc ctatttttat    4920
aggttaatgt catgataata atggtttctt agacgtcagg tggcacttt cggggaaatg    4980
```

```
tgcgcggaac ccctatttgt ttatttttct aaatacattc aaatatgtat ccgctcatga    5040
gacaataacc ctgataaatg cttcaataat attgaaaaag gaagagtatg agtattcaac    5100
atttccgtgt cgcccttatt ccctttttg cggcattttg ccttcctgtt tttgctcacc     5160
cagaaacgct ggtgaaagta aaagatgctg aagatcagtt gggtgcacga gtgggttaca    5220
tcgaactgga tctcaacagc ggtaagatcc ttgagagttt tcgccccgaa gaacgttttc    5280
caatgatgag cacttttaaa gttctgctat gtggcgcggt attatcccgt attgacgccg    5340
ggcaagagca actcggtcgc cgcatacact attctcagaa tgacttggtt gagtactcac    5400
cagtcacaga aaagcatctt acggatggca tgacagtaag agaattatgc agtgctgcca    5460
taaccatgag tgataacact gcggccaact tacttctgac aacgatcgga ggaccgaagg    5520
agctaaccgc ttttttgcac aacatggggg atcatgtaac tcgccttgat cgttgggaac    5580
cggagctgaa tgaagccata ccaaacgacg agcgtgacac cacgatgcct gtagcaatgg    5640
caacaacgtt gcgcaaacta ttaactggcg aactacttac tctagcttcc cggcaacaat    5700
taatagactg gatggaggcg gataaagttg caggaccact tctgcgctcg gcccttccgg    5760
ctggctggtt tattgctgat aaatctggag ccggtgagcg tgggtctcgc ggtatcattg    5820
cagcactggg gccagatggt aagccctccc gtatcgtagt tatctacacg acggggagtc    5880
aggcaactat ggatgaacga atagacaga tcgctgagat aggtgcctca ctgattaagc      5940
attggtaact gtcagaccaa gtttactcat atatacttta gattgattta aaacttcatt    6000
tttaatttaa aaggatctag gtgaagatcc tttttgataa tctcatgacc aaaatccctt    6060
aacgtgagtt ttcgttccac tgagcgtcag accccgtaga aaagatcaaa ggatcttctt    6120
gagatccttt ttttctgcgc gtaatctgct gcttgcaaac aaaaaaacca ccgctaccag    6180
cggtggtttg tttgccggat caagagctac caactctttt tccgaaggta actggcttca    6240
gcagagcgca gataccaaat actgtccttc tagtgtagcc gtagttaggc caccacttca    6300
agaactctgt agcaccgcct acatacctcg ctctgctaat cctgttacca gtggctgctg    6360
ccagtggcga taagtcgtgt cttaccgggt tggactcaag acgatagtta ccggataagg    6420
cgcagcggtc gggctgaacg gggggttcgt gcacacagcc cagcttggag cgaacgacct    6480
acaccgaact gagataccta cagcgtgagc tatgagaaag cgccacgctt cccgaaggga    6540
gaaaggcgga caggtatccg gtaagcggca gggtcggaac aggagagcgc acgagggagc    6600
ttccaggggg aaacgcctgg tatctttata gtcctgtcgg gtttcgccac ctctgacttg    6660
agcgtcgatt tttgtgatgc tcgtcagggg ggcggagcct atggaaaaac gccagcaacg    6720
cggccttttt acggttcctg gccttttgct ggccttttgc tcacatgttc tttcctgcgt    6780 tatccctga ttctgtggat aaccgtatta ccgcctttga gtgagctgat accgctcgcc      6840
gcagccgaac gaccgagcgc agcgagtcag tgagcgagga agcggaagag cgcccaatac    6900
gcaaaccgcc tctccccgcg cgttggccga ttcattaatg                           6940
```

<210> SEQ ID NO 15
<211> LENGTH: 7257
<212> TYPE: DNA
<213> ORGANISM: Artificial Sequence
<220> FEATURE:
<223> OTHER INFORMATION: Synthetic Polynucleotide

<400> SEQUENCE: 15

```
cagcagctgc gcgctcgctc gctcactgag gccgcccggg caaagcccgg gcgtcgggcg    60
```

```
acctttggtc gcccggcctc agtgagcgag cgagcgcgca gagagggagt ggccaactcc    120
atcactaggg gttccttgta gttaatgatt aacccgccat gctacttatc tacgtagcca    180
tgctctagcg gcctcggcct ctgcataaat aaaaaaaatt agtcagccat gagcttggcc    240
cattgcatac gttgtatcca tatcataata tgtacattta tattggctca tgtccaacat    300
taccgccatg ttgacattga ttattgacta gttattaata gtaatcaatt acgggtcat    360
tagttcatag cccatatatg gagttccgcg ttacataact tacggtaaat ggcccgcctg    420
gctgaccgcc caacgacccc cgcccattga cgtcaataat gacgtatgtt cccatagtaa    480
cgccaatagg gactttccat tgacgtcaat gggtggagta tttacggtaa actgcccact    540
tggcagtaca tcaagtgtat catatgccaa gtacgccccc tattgacgtc aatgacggta    600
aatgggccgc ctggcattat gcccagtaca tgaccttatg ggactttcct acttggcagt    660
acatctacgt attagtcatc gctattacca tggtgatgcg gttttggcag tacatcaatg    720
ggcgtggata gcggtttgac tcacggggat ttccaagtct ccaccccatt gacgtcaatg    780
ggagtttgtt ttggcaccaa aatcaacggg actttccaaa atgtcgtaac aactccgccc    840
cattgacgca aatgggcggt aggcgtgtac ggtgggaggt ctatataagc agagctcgtt    900
tagtgaaccg tcagatcgcc tggagacgcc atccacgctg ttttgacctc catagaagac    960
accgggaccg atccagcctc ccctcgaagc tgatcctgag aacttcaggg tgagtctatg   1020
ggacccttga tgttttcttt ccccttcttt tctatggtta agttcatgtc ataggaaggg   1080
gagaagtaac agggtacaca tattgaccaa atcagggtaa ttttgcattt gtaattttaa   1140
aaaatgcttt cttcttttaa tatacttttt tgtttatctt atttctaata ctttccctaa   1200
tctctttctt tcagggcaat aatgatacaa tgtatcatgc ctctttgcac cattctaaag   1260
aataacagta ataatttctg ggttaaggca atagcaatat ttctgcatat aaatatttct   1320
gcatataaat tgtaactgat gtaagaggtt tcatattgct aatagcagct acaatccagc   1380
taccattctg ctttttatttt atggttggga taaggctgga ttattctgag tccaagctag   1440
gcccttttgc taatcatgtt catacctctt atcttcctcc cacagctcct gggcaacgtg   1500
ctggtctgtg tgctggccca tcactttggc aaagaattcc gcgggccgg gatccaccgg   1560
tcgccaccat ggtgagcaag ggcgaggagc tgttcaccgg ggtggtgccc atcctggtcg   1620
agctggacgg cgacgtaaac ggccacaagt tcagcgtgtc cggcgagggc gagggcgatg   1680
ccacctacgg caagctgacc ctgaagttca tctgcaccac cggcaagctg cccgtgccct   1740
ggcccaccct cgtgaccacc ctgacctacg gcgtgcagtg cttcagccgc taccccgacc   1800
acatgaagca gcacgacttc ttcaagtccg ccatgcccga aggctacgtc caggagcgca   1860
ccatcttctt caaggacgac ggcaactaca agacccgcgc cgaggtgaag ttcgagggcg   1920
acaccctggt gaaccgcatc gagctgaagg gcatcgactt caaggaggac ggcaacatcc   1980
tggggcacaa gctggagtac aactacaaca gccacaacgt ctatatcatg gccgacaagc   2040
agaagaacgg catcaaggtg aacttcaaga tccgccacaa catcgaggac ggcagcgtgc   2100
agctcgccga ccactaccag cagaacaccc ccatcggcga cggccccgtg ctgctgcccg   2160
acaaccacta cctgagcacc cagtccgccc tgagcaaaga ccccaacgag aagcgcgatc   2220
acatggtcct gctggagttc gtgaccgccg ccgggatcac tctcggcatg gacgagctgt   2280
acaagtaaag cggccgctct agaggatcca agcttatcga taccgtcgac ctcgagggcc   2340
cagatctaat tcaccccacc agtgcaggct gcctatcaga aagtggtggc tggtgtggct   2400
aatgccctgg cccacaagta tcactaagct cgctttcttg ctgtccaatt tctattaaag   2460
```

```
gttcctttgt tccctaagtc caactactaa actggggggat attatgaagg gccttgagca    2520
tctggattct gcctaataaa aaacattat tttcattgca atgatgtatt taaattattt     2580
ctgaatattt tactaaaaag ggaatgtggg aggtcagtgc atttaaaaca taaagaaatg    2640
aagagctagt tcaaaccttg ggaaaataca ctatatctta aactccatga aagaaggtga    2700
ggctgcaaac agctaatgca cattggcaac agcccctgat gcctatgcct tattcatccc    2760
tcagaaaagg attcaagtag aggcttgatt tggaggttaa agttttgcta tgctgtatt     2820
tacattactt attgttttag ctgtcctcat gaatgtcttt tcactaccca tttgcttatc    2880
ctgcatctct cagccttgac tccactcagt tctcttgctt agagatacca cctttcccct    2940
gaagtgttcc ttccatgttt tacggcgaga tggtttctcc tcgcctggcc actcagcctt    3000
agttgtctct gttgtcttat agaggtctac ttgaagaagg aaaaacaggg ggcatggttt    3060
gactgtcctg tgagcccttc ttccctgcct cccccactca cagtgacccg gaatccctcg    3120
acaggtacct ttagggttag ggttagggtt agggaaaaat ttagggttag ggttaggggtt   3180
agggaaaaat ttagggttag ggttagggtt agggaaaaat ttagggttag ggttagggtt    3240
agggaaaaat ttagggttag ggttagggtt agggaaaaac cctaaccctta accctaaccc   3300
taaattttt ccctaaccct aaccctaacc ctaaattttt tccctaaccc taaccctaac     3360
cctaaatttt ttccctaacc ctaaccctaa ccctaaattt tttccctaac cctaacccta    3420
accctaaatt ttttgctagc tctagagcat ggctacgtag ataagtagca tggcgggtta    3480
atcattaact acaaggaacc cctagtgatg gagttggcca ctccctctct gcgcgctcgc    3540
tcgctcactg aggccggggcg accaaaggtc gcccgacgcc cgggctttgc ccgggcggcc   3600
tcagtgagcg agcgagcgcg ccagctggcg taatagcgaa gaggcccgca ccgatcgccc    3660
ttcccaacag ttgcgcagcc tgaatggcga atggaattcc agacgattga gcgtcaaaat    3720
gtaggtattt ccatgagcgt ttttcctgtt gcaatggctg gcggtaatat tgttctggat    3780
attaccagca aggccgatag tttgagttct tctactcagg caagtgatgt tattactaat    3840
caaagaagta ttgcgacaac ggttaatttg cgtgatggac agactctttt actcggtggc    3900
ctcactgatt ataaaaacac ttctcaggat tctggcgtac cgttcctgtc taaaatccct    3960
ttaatcggcc tcctgtttag ctcccgctct gattctaacg aggaaagcac gttatacgtg    4020
ctcgtcaaag caaccatagt acgcgccctg tagcggcgca ttaagcgcgg cgggtgtggt    4080
ggttacgcgc agcgtgaccg ctacacttgc cagcgcccta gcgcccgctc ctttcgcttt    4140
cttcccttcc tttctcgcca cgttcgccgg ctttccccgt caagctctaa atcgggggct    4200
ccctttaggg ttccgattta gtgctttacg gcacctcgac cccaaaaaac ttgattaggg    4260
tgatggttca cgtagtgggc catcgccctg atagacggtt tttcgccctt tgacgttgga    4320
gtccacgttc tttaatagtg gactcttgtt ccaaactgga acaacactca accctatctc    4380
ggtctattct tttgatttat aagggatttt gccgatttcg gcctattggt taaaaaatga    4440
gctgatttaa caaaaattta acgcgaattt taacaaaata ttaacgttta caatttaaat    4500
atttgcttat acaatcttcc tgttttttggg gcttttctga ttatcaaccg ggtacatat    4560
gattgacatg ctagttttac gattaccgtt catcgattct cttgtttgct ccagactctc    4620
aggcaatgac ctgatagcct ttgtagagac ctctcaaaaa tagctaccct ctccggcatg    4680
aatttatcag ctgaacggt tgaatatcat attgatggtg atttgactgt ctccggcctt     4740
tctcacccgt ttgaatcttt acctacacat tactcaggca ttgcatttaa aatatatgag    4800
```

```
ggttctaaaa attttttatcc ttgcgttgaa ataaaggctt ctcccgcaaa agtattacag    4860
ggtcataatg tttttggtac aaccgattta gctttatgct ctgaggcttt attgcttaat    4920
tttgctaatt ctttgccttg cctgtatgat ttattggatg ttggaattcc tgatgcggta    4980
ttttctcctt acgcatctgt gcggtatttc acaccgcata tggtgcactc tcagtacaat    5040
ctgctctgat gccgcatagt taagccagcc ccgacacccg ccaacacccg ctgacgcgcc    5100
ctgacgggct tgtctgctcc cggcatccgc ttacagacaa gctgtgaccg tctccgggag    5160
ctgcatgtgt cagaggtttt caccgtcatc accgaaacgc gcgagacgaa agggcctcgt    5220
gatacgccta ttttttatagg ttaatgtcat gataataatg gtttcttaga cgtcaggtgg    5280
cacttttcgg ggaaatgtgc gcggaacccc tatttgttta ttttttctaaa tacattcaaa    5340 tatgtatccg ctcatgagac aataaccctg ataaatgctt caataatatt gaaaaggaa    5400 gagtatgagt attcaacatt tccgtgtcgc ccttattccc ttttttgcgg cattttgcct    5460
tcctgttttt gctcacccag aaacgctggt gaaagtaaaa gatgctgaag atcagttggg    5520
tgcacgagtg ggttacatcg aactggatct caacagcggt aagatccttg agagttttcg    5580
ccccgaagaa cgttttccaa tgatgagcac ttttaaagtt ctgctatgtg gcgcggtatt    5640
atcccgtatt gacgccgggc aagagcaact cggtcgccgc atacactatt ctcagaatga    5700
cttggttgag tactcaccag tcacagaaaa gcatcttacg gatggcatga cagtaagaga    5760
attatgcagt gctgccataa ccatgagtga taacactgcg gccaacttac ttctgacaac    5820
gatcggagga ccgaaggagc taaccgcttt tttgcacaac atgggggatc atgtaactcg    5880
ccttgatcgt tgggaaccgg agctgaatga agccatacca aacgacgagc gtgacaccac    5940
gatgcctgta gcaatggcaa caacgttgcg caaactatta actggcgaac tacttactct    6000
agcttcccgg caacaattaa tagactggat ggaggcggat aaagttgcag gaccacttct    6060
gcgctcggcc cttccggctg gctggtttat tgctgataaa tctggagccg gtgagcgtgg    6120
gtctcgcggt atcattgcag cactggggcc agatggtaag ccctcccgta tcgtagttat    6180
ctacacgacg gggagtcagg caactatgga tgaacgaaat agacagatcg ctgagatagg    6240
tgcctcactg attaagcatt ggtaactgtc agaccaagtt tactcatata ctttagat    6300 tgatttaaaa cttcatttt aatttaaaag gatctaggtg aagatccttt ttgataatct    6360
catgaccaaa atcccttaac gtgagttttc gttccactga gcgtcagacc ccgtagaaaa    6420
gatcaaagga tcttcttgag atcctttttt tctgcgcgta atctgctgct tgcaaacaaa    6480
aaaaccaccg ctaccagcgg tggtttgttt gccggatcaa gagctaccaa ctcttttcc    6540 gaaggtaact ggcttcagca gagcgcagat accaaatact gtccttctag tgtagccgta    6600
gttaggccac cacttcaaga actctgtagc accgcctaca tacctcgctc tgctaatcct    6660
gttaccagtg gctgctgcca gtggcgataa gtcgtgtctt accgggttgg actcaagacg    6720
atagttaccg gataaggcgc agcggtcggg ctgaacgggg ggttcgtgca cacagcccag    6780
cttggagcga acgacctaca ccgaactgag atacctacag cgtgagctat gagaaagcgc    6840
cacgcttccc gaagggagaa aggcggacag gtatccggta agcggcaggg tcggaacagg    6900
agagcgcacg agggagcttc cagggggaaa cgcctggtat ctttatagtc ctgtcgggtt    6960
tcgccacctc tgacttgagc gtcgattttt gtgatgctcg tcaggggggc ggagcctatg    7020
gaaaaacgcc agcaacgcgg ccttttacg gttcctggcc ttttgctggc cttttgctca    7080
catgttcttt cctgcgttat cccctgattc tgtggataac cgtattaccg cctttgagtg    7140
agctgatacc gctcgccgca gccgaacgac cgagcgcagc gagtcagtga gcgaggaagc    7200
```
ggaagagcgc ccaatacgca aaccgcctct ccccgcgcgt tggccgattc attaatg        7257

<210> SEQ ID NO 16
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 16
tcctggaggg gaagt                                                         15

<210> SEQ ID NO 17
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 17
tcctggatgg gaagt                                                         15

<210> SEQ ID NO 18
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 18
ttcccatcca ggcctggatg ggaa                                               24

<210> SEQ ID NO 19
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 19
cttaccgctg cacctggatg ggaa                                               24

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
gggggggggg gggggggggg                                                    20

<210> SEQ ID NO 21
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 21
tgactgtgaa ggttagagat ga                                                 22

<210> SEQ ID NO 22
<211> LENGTH: 15
<212> TYPE: DNA

```
<213> ORGANISM: Artificial Sequence
<220> FEATURE:
<223> OTHER INFORMATION: Synthetic Polynucleotide

<400> SEQUENCE: 22
tcctggaggg gttgt                                                          15

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 23
tgctcctgga ggggttgt                                                       18

<210> SEQ ID NO 24
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 24
cctggcgggg                                                                10

<210> SEQ ID NO 25
<211> LENGTH: 4369
<212> TYPE: DNA
<213> ORGANISM: Artificial Sequence
<220> FEATURE:
<223> OTHER INFORMATION: Synthetic Polynucleotide

<400> SEQUENCE: 25
aaagcttccc gggggatct gggccactcc ctctctgcgc gctcgctcgc tcactgaggc          60
cgggcgacca aggtcgccc gacgcccggg ctttgcccgg gcggcctcag tgagcgagcg         120
agcgcgcaga gagggagtgg ccaactccat cactaggggt tcctggaggg gtggagtcgt        180
gacctaggca tatgccaagt acgcccccta ttgacgtcaa tgacggtaaa tggcccgcct        240
ggcattatgc ccagtacatg accttatggg actttcctac ttggcagtac atctacgtat        300
tagtcatcgc tattaccatg gtgatgcggt tttggcagta catcaatggg cgtggatagc        360
ggtttgactc acggggattt ccaagtctcc accccattga cgtcaatggg agtttgtttt        420
ggcaccaaaa tcaacgggac tttccaaaat gtcgtaacaa ctccgcccca ttgacgcaaa        480
tgggcggtag gcgtgtacgg tgggaggtct atataagcag agctcgttta gtgaaccgtc        540
agatcgcctg gagacgccat ccggactcta aggtaaatat aaaattttta agtgtataat        600
gtgttaaact actgattcta attgtttctc tcttttagat tccaaccttt ggaactgaat        660
tccgcgggcc cgggatccac cggtcgccac catggtgagc aagggcgagg agctgttcac        720
cggggtggtg cccatcctgg tcgagctgga cggcgacgta acggccaca agttcagcgt        780 gtccggcgag ggcgagggcg atgccaccta cggcaagctg accctgaagt tcatctgcac        840
caccggcaag ctgcccgtgc cctggcccac cctcgtgacc accctgacct acggcgtgca        900
gtgcttcagc cgctaccccg accacatgaa gcagcacgac ttcttcaagt ccgccatgcc        960
cgaaggctac gtccaggagc gcaccatctt cttcaaggac gacggcaact acaagacccg       1020
cgccgaggtg aagttcgagg gcgacaccct ggtgaaccgc atcgagctga agggcatcga       1080
cttcaaggag gacggcaaca tcctggggca caagctggag tacaactaca acagccacaa       1140
```

```
cgtctatatc atggccgaca agcagaagaa cggcatcaag gtgaacttca agatccgcca    1200
caacatcgag gacggcagcg tgcagctcgc cgaccactac cagcagaaca cccccatcgg    1260
cgacggcccc gtgctgctgc ccgacaacca ctacctgagc acccagtccg ccctgagcaa    1320
agaccccaac gagaagcgcg atcacatggt cctgctggag ttcgtgaccg ccgccgggat    1380
cactctcggc atggacgagc tgtacaagta aagcggccgc taggcctcac ctgcgatctc    1440
gatgctttat ttgtgaaatt tgtgatgcta ttgctttatt tgtaaccatt ataagctgca    1500
ataaacaagt taacaacaac aattgcattc attttatgtt tcaggttcag gggaggtgt    1560 gggaggtttt ttaaactagt ccactccctc tctgcgcgct cgctcgctca ctgaggccgg    1620
gcgaccaaag gtcgcccgac gcccgggctt tgcccgggcg gcctcagtga gcgagcgagc    1680
gcgcagagag ggacagatcc gggcccgcat gcgtcgacaa ttcactggcc gtcgttttac    1740
aacgtcgtga ctgggaaaac cctggcgtta cccaacttaa tcgccttgca gcacatcccc    1800
ctttcgccag ctggcgtaat agcgaagagg cccgcaccga tcgcccttcc caacagttgc    1860
gcagcctgaa tggcgaatgg cgcctgatgc ggtattttct ccttacgcat ctgtgcggta    1920
tttcacaccg catatggtgc actctcagta caatctgctc tgatgccgca tagttaagcc    1980
agccccgaca cccgccaaca cccgctgacg cgccctgacg ggcttgtctg ctcccggcat    2040
ccgcttacag acaagctgtg accgtctccg ggagctgcat gtgtcagagg ttttcaccgt    2100
catcaccgaa acgcgcgaga cgaaagggcc tcgtgatacg cctatttta taggttaatg    2160 tcatgataat aatggtttct tagacgtcag gtggcacttt tcggggaaat gtgcgcggaa    2220
cccctatttg tttatttttc taaatacatt caaatatgta tccgctcatg agacaataac    2280
cctgataaat gcttcaataa tattgaaaaa ggaagagtat gagtattcaa catttccgtg    2340
tcgcccttat tcccttttttt gcggcatttt gccttcctgt ttttgctcac ccagaaacgc    2400
tggtgaaagt aaaagatgct gaagatcagt tgggtgcacg agtgggttac atcgaactgg    2460
atctcaacag cggtaagatc cttgagagtt ttcgccccga agaacgtttt ccaatgatga    2520
gcacttttaa agttctgcta tgtggcgcgg tattatcccg tattgacgcc gggcaagagc    2580
aactcggtcg ccgcatacac tattctcaga atgacttggt tgagtactca ccagtcacag    2640
aaaagcatct tacggatggc atgacagtaa gagaattatg cagtgctgcc ataaccatga    2700
gtgataacac tgcggccaac ttacttctga caacgatcgg aggaccgaag gagctaaccg    2760
cttttttgca caacatgggg gatcatgtaa ctcgccttga tcgttgggaa ccggagctga    2820
atgaagccat accaaacgac gagcgtgaca ccacgatgcc tgtagcaatg gcaacaacgt    2880
tgcgcaaact attaactggc gaactactta ctctagcttc ccggcaacaa ttaatagact    2940
ggatggaggc ggataaagtt gcaggaccac ttctgcgctc ggcccttccg gctggctggt    3000
ttattgctga taaatctgga gccggtgagc gtgggtctcg cggtatcatt gcagcactgg    3060
ggccagatgg taagccctcc cgtatcgtag ttatctacac gacggggagt caggcaacta    3120
tggatgaacg aaatagacag atcgctgaga taggtgcctc actgattaag cattggtaac    3180
tgtcagacca agtttactca tatatacttt agattgattt aaaacttcat ttttaattta    3240
aaaggatcta ggtgaagatc ctttttgata atctcatgac caaaatccct aacgtgagt    3300 tttcgttcca ctgagcgtca gaccccgtag aaaagatcaa aggatcttct tgagatcctt    3360 ttttttctgcg cgtaatctgc tgcttgcaaa caaaaaaacc accgctacca gcggtggttt    3420
gtttgccgga tcaagagcta ccaactcttt ttccgaaggt aactggcttc agcagagcgc    3480
```

| | |
|---|---|
| agataccaaa tactgttctt ctagtgtagc cgtagttagg ccaccacttc aagaactctg | 3540 |
| tagcaccgcc tacatacctc gctctgctaa tcctgttacc agtggctgct gccagtggcg | 3600 |
| ataagtcgtg tcttaccggg ttggactcaa gacgatagtt accggataag cgcagcggt | 3660 |
| cgggctgaac gggggggttcg tgcacacagc ccagcttgga gcgaacgacc tacaccgaac | 3720 |
| tgagatacct acagcgtgag ctatgagaaa gcgccacgct tcccgaaggg agaaaggcgg | 3780 |
| acaggtatcc ggtaagcggc agggtcggaa caggagagcg cacgagggag cttccagggg | 3840 |
| gaaacgcctg gtatctttat agtcctgtcg ggtttcgcca cctctgactt gagcgtcgat | 3900 |
| ttttgtgatg ctcgtcaggg gggcggagcc tatggaaaaa cgccagcaac gcggcctttt | 3960 |
| tacggttcct ggccttttgc tggccttttg ctcacatgtt ctttcctgcg ttatcccctg | 4020 |
| attctgtgga taaccgtatt accgcctttg agtgagctga taccgctcgc cgcagccgaa | 4080 |
| cgaccgagcg cagcgagtca gtgagcgagg aagcggaaga gcgcccaata cgcaaaccgc | 4140 |
| ctctccccgc gcgttggccg attcattaat gcagctggca cgacaggttt cccgactgga | 4200 |
| aagcgggcag tgagcgcaac gcaattaatg tgagttagct cactcattag gcaccccagg | 4260 |
| ctttacactt tatgcttccg gctcgtatgt tgtgtggaat tgtgagcgga taacaatttc | 4320 |
| acacaggaaa cagctatgac catgattacg ccaagctctc gagatctag | 4369 |

<210> SEQ ID NO 26
<211> LENGTH: 4450
<212> TYPE: DNA
<213> ORGANISM: Artificial Sequence
<220> FEATURE:
<223> OTHER INFORMATION: Synthetic Polynucleotide

<400> SEQUENCE: 26

| | |
|---|---|
| aaagcttccc gggggatct gggccactcc ctctctgcgc gctcgctcgc tcactgaggc | 60 |
| cgggcgacca aaggtcgccc gacgcccggg ctttgcccgg gcggcctcag tgagcgagcg | 120 |
| agcgcgcaga gagggagtgg ccaactccat cactagggt tcctggaggg gtggagtcgt | 180 |
| gacctaggca tatgccaagt acgccccta ttgacgtcaa tgacggtaaa tggcccgcct | 240 |
| ggcattatgc ccagtacatg acctatggg actttcctac ttggcagtac atctacgtat | 300 |
| tagtcatcgc tattaccatg gtgatgcggt tttggcagta catcaatggg cgtggatagc | 360 |
| ggtttgactc acggggattt ccaagtctcc accccattga cgtcaatggg agtttgtttt | 420 |
| ggcaccaaaa tcaacgggac tttccaaaat gtcgtaacaa ctccgcccca ttgacgcaaa | 480 |
| tgggcggtag gcgtgtacgg tgggaggtct atataagcag agctcgttta gtgaaccgtc | 540 |
| agatcgcctg gagacgccat ccggactcta aggtaaatat aaaatttta agtgtataat | 600 |
| gtgttaaact actgattcta attgtttctc tcttttagat tccaacccttt ggaactgaat | 660 |
| tccgcgggcc cgggatccac cggtcgccac catggtgagc aagggcgagg agctgttcac | 720 |
| cggggtggtg cccatcctgg tcgagctgga cggcgacgta acggccaca gttcagcgt | 780 |
| gtccggcgag ggcgagggcg atgccaccta cggcaagctg accctgaagt tcatctgcac | 840 |
| caccggcaag ctgcccgtgc cctggcccac cctcgtgacc accctgacct acggcgtgca | 900 |
| gtgcttcagc cgctacccg accacatgaa gcagcacgac ttcttcaagt ccgccatgcc | 960 |
| cgaaggctac gtccaggagc gcaccatctt cttcaaggac gacggcaact acaagacccg | 1020 |
| cgccgaggtg aagttcgagg gcgacaccct ggtgaaccgc atcgagctga agggcatcga | 1080 |
| cttcaaggag gacggcaaca tcctggggca caagctggag tacaactaca acagccacaa | 1140 |
| cgtctatatc atggccgaca agcagaagaa cggcatcaag gtgaacttca agatccgcca | 1200 |

-continued

```
caacatcgag gacggcagcg tgcagctcgc cgaccactac cagcagaaca ccccatcgg      1260
cgacggcccc gtgctgctgc ccgacaacca ctacctgagc acccagtccg ccctgagcaa      1320
agacccaac  gagaagcgcg atcacatggt cctgctggag ttcgtgaccg ccgccgggat      1380
cactctcggc atggacgagc tgtacaagta aagcggccgc taggcctcac ctgcgatctc      1440
gatgctttat ttgtgaaatt tgtgatgcta ttgctttatt tgtaaccatt ataagctgca      1500
ataaacaagt taacaacaac aattgcattc attttatgtt tcaggttcag ggggaggtgt      1560
gggaggtttt ttaaatcgat tggcgcgcac ccacggcctg aaaatggcg cgcacccacg       1620
gcctgaaaaa tggcgcgcac ccacggcctg aaaaactag tccactccct ctctgcgcgc      1680
tcgctcgctc actgaggccg ggcgaccaaa ggtcgcccga cgcccgggct tgcccgggc      1740
ggcctcagtg agcgagcgag cgcgcagaga ggacagatc cgggcccgca tgcgtcgaca       1800
attcactggc cgtcgtttta caacgtcgtg actgggaaaa ccctggcgtt acccaactta      1860
atcgccttgc agcacatccc cctttcgcca gctggcgtaa tagcgaagag gcccgcaccg      1920
atcgccctttc ccaacagttg cgcagcctga atggcgaatg gcgcctgatg cggtattttc    1980
tccttacgca tctgtgcggt atttcacacc gcatatggtg cactctcagt acaatctgct     2040
ctgatgccgc atagttaagc cagccccgac acccgccaac acccgctgac gcgccctgac    2100
gggcttgtct gctcccggca tccgcttaca gacaagctgt gaccgtctcc gggagctgca    2160
tgtgtcagag gttttcaccg tcatcaccga aacgcgcgag acgaaagggc ctcgtgatac    2220
gcctatttt  ataggttaat gtcatgataa taatggtttc ttagacgtca ggtggcactt    2280
ttcggggaaa tgtgcgcgga acccctattt gtttattttt ctaaatacat tcaaatatgt    2340
atccgctcat gagacaataa ccctgataaa tgcttcaata atattgaaaa aggaagagta    2400
tgagtattca acatttccgt gtcgccctta ttccctttt  tgcggcattt tgccttcctg    2460
ttttgctca  cccagaaacg ctggtgaaag taaaagatgc tgaagatcag ttgggtgcac    2520
gagtgggtta catcgaactg gatctcaaca gcggtaagat ccttgagagt tttcgccccg    2580
aagaacgttt tccaatgatg agcactttta aagttctgct atgtggcgcg gtattatccc    2640
gtattgacgc cgggcaagag caactcggtc gccgcataca ctattctcag aatgacttgg    2700
ttgagtactc accagtcaca gaaaagcatc ttacggatgg catgacagta agagaattat    2760
gcagtgctgc cataaccatg agtgataaca ctgcggccaa cttacttctg acaacgatcg    2820
gaggaccgaa ggagctaacc gcttttttgc acaacatggg ggatcatgta actcgccttg    2880
atcgttggga accggagctg aatgaagcca taccaaacga cgagcgtgac accacgatgc    2940
ctgtagcaat ggcaacaacg ttgcgcaaac tattaactgg cgaactactt actctagctt    3000
cccggcaaca attaatagac tggatggagg cggataaagt tgcaggacca cttctgcgct    3060
cggcccttcc ggctggctgg tttattgctg ataaatctgg agccggtgag cgtgggtctc    3120
gcggtatcat tgcagcactg gggccagatg gtaagccctc ccgtatcgta gttatctaca    3180
cgacggggag tcaggcaact atggatgaac gaaatagaca gatcgctgag ataggtgcct    3240
cactgattaa gcattggtaa ctgtcagacc aagtttactc atatatactt tagattgatt    3300
taaaacttca ttttaatttt aaaaggatct aggtgaagat cctttttgat aatctcatga    3360
ccaaaatccc ttaacgtgag ttttcgttcc actgagcgtc agaccccgta gaaaagatca    3420
aaggatcttc ttgagatcct ttttttctgc gcgtaatctg ctgcttgcaa acaaaaaaac    3480
caccgctacc agcggtggtt tgtttgccgg atcaagagct accaactctt tttccgaagg    3540
```

| | |
|---|---|
| taactggctt cagcagagcg cagataccaa atactgttct tctagtgtag ccgtagttag | 3600 |
| gccaccactt caagaactct gtagcaccgc ctacatacct cgctctgcta atcctgttac | 3660 |
| cagtggctgc tgccagtggc gataagtcgt gtcttaccgg gttggactca agacgatagt | 3720 |
| taccggataa ggcgcagcgg tcgggctgaa cggggggttc gtgcacacag cccagcttgg | 3780 |
| agcgaacgac ctacaccgaa ctgagatacc tacagcgtga gctatgagaa agcgccacgc | 3840 |
| ttcccgaagg gagaaaggcg gacaggtatc cggtaagcgg cagggtcgga acaggagagc | 3900 |
| gcacgaggga gcttccaggg ggaaacgcct ggtatcttta tagtcctgtc gggtttcgcc | 3960 |
| acctctgact tgagcgtcga ttttgtgat gctcgtcagg ggggcggagc ctatggaaaa | 4020 |
| acgccagcaa cgcggccttt ttacggttcc tggccttttg ctggccttt gctcacatgt | 4080 |
| tctttcctgc gttatcccct gattctgtgg ataaccgtat taccgccttt gagtgagctg | 4140 |
| ataccgctcg ccgcagccga acgaccgagc gcagcgagtc agtgagcgag gaagcggaag | 4200 |
| agcgcccaat acgcaaaccg cctctccccg cgcgttggcc gattcattaa tgcagctggc | 4260 |
| acgacaggtt tcccgactgg aaagcgggca gtgagcgcaa cgcaattaat gtgagttagc | 4320 |
| tcactcatta ggcaccccag gctttacact ttatgcttcc ggctcgtatg ttgtgtggaa | 4380 |
| ttgtgagcgg ataacaattt cacacaggaa acagctatga ccatgattac gccaagctct | 4440 |
| cgagatctag | 4450 |

<210> SEQ ID NO 27
<211> LENGTH: 4425
<212> TYPE: DNA
<213> ORGANISM: Artificial Sequence
<220> FEATURE:
<223> OTHER INFORMATION: Synthetic Polynucleotide

<400> SEQUENCE: 27

| | |
|---|---|
| aaagcttccc gggggatct gggccactcc ctctctgcgc gctcgctcgc tcactgaggc | 60 |
| cgggcgacca aggtcgccc gacgcccggg cttgcccgg gcggcctcag tgagcgagcg | 120 |
| agcgcgcaga gagggagtgg ccaactccat cactaggggt tcctggaggg gtggagtcgt | 180 |
| gacctaggca tatgccaagt acgccccta ttgacgtcaa tgacggtaaa tggcccgcct | 240 |
| ggcattatgc ccagtacatg acctatggg actttcctac ttggcagtac atctacgtat | 300 |
| tagtcatcgc tattaccatg gtgatgcggt tttggcagta catcaatggg cgtggatagc | 360 |
| ggtttgactc acggggattt ccaagtctcc accccattga cgtcaatggg agtttgtttt | 420 |
| ggcaccaaaa tcaacgggac tttccaaaat gtcgtaacaa ctccgcccca ttgacgcaaa | 480 |
| tgggcggtag gcgtgtacgg tgggaggtct atataagcag agctcgttta gtgaaccgtc | 540 |
| agatcgcctg gagacgccat ccggactcta aggtaaatat aaaatttta agtgtataat | 600 |
| gtgttaaact actgattcta attgtttctc tcttttagat tccaacccttt ggaactgaat | 660 |
| tccgcgggcc cgggatccac cggtcgccac catggtgagc aagggcgagg agctgttcac | 720 |
| cggggtggtg cccatcctgg tcgagctgga cggcgacgta aacggccaca agttcagcgt | 780 |
| gtccggcgag ggcgagggcg atgccaccta cggcaagctg accctgaagt tcatctgcac | 840 |
| caccggcaag ctgcccgtgc cctggcccac cctcgtgacc accctgacct acggcgtgca | 900 |
| gtgcttcagc cgctaccccg accacatgaa gcagcacgac ttcttcaagt ccgccatgcc | 960 |
| cgaaggctac gtccaggagc gcaccatctt cttcaaggac gacggcaact acaagacccg | 1020 |
| cgccgaggtg aagttcgagg gcgacaccct ggtgaaccgc atcgagctga agggcatcga | 1080 |
| cttcaaggag gacggcaaca tcctggggca caagctggag tacaactaca acagccacaa | 1140 |

```
cgtctatatc atggccgaca agcagaagaa cggcatcaag gtgaacttca agatccgcca      1200
caacatcgag gacggcagcg tgcagctcgc cgaccactac cagcagaaca cccccatcgg      1260
cgacggcccc gtgctgctgc ccgacaacca ctacctgagc acccagtccg ccctgagcaa      1320
agaccccaac gagaagcgcg atcacatggt cctgctggag ttcgtgaccg ccgccgggat      1380
cactctcggc atggacgagc tgtacaagta aagcggccgc taggcctcac ctgcgatctc      1440
gatgctttat ttgtgaaatt tgtgatgcta ttgctttatt tgtaaccatt ataagctgca      1500
ataaacaagt taacaacaac aattgcattc attttatgtt tcaggttcag ggggaggtgt      1560
gggaggtttt ttaaatcgat tggcgcgcac ccacggcctg aaaaatggcg cgcacccacg      1620
gcctgaaaaa actagtccac tccctctctg cgcgctcgct cgctcactga ggccgggcga      1680
ccaaaggtcg cccgacgccc gggctttgcc cgggcggcct cagtgagcga gcgagcgcgc      1740
agagagggac agatccgggc cgcatgcgt cgacaattca ctggccgtcg ttttacaacg      1800
tcgtgactgg gaaaaccctg gcgttaccca acttaatcgc cttgcagcac atccccctttt      1860 cgccagctgg cgtaatagcg aagaggcccg caccgatcgc ccttcccaac agttgcgcag      1920
cctgaatggc gaatgcgcc tgatgcggta ttttctcctt acgcatctgt gcggtatttc      1980
acaccgcata tggtgcactc tcagtacaat ctgctctgat gccgcatagt taagccagcc      2040
ccgacacccg ccaacacccg ctgacgcgcc ctgacgggct tgtctgctcc cggcatccgc      2100
ttacagacaa gctgtgaccg tctccgggag ctgcatgtgt cagaggtttt caccgtcatc      2160
accgaaacgc gcgagacgaa agggcctcgt gatacgccta tttttatagg ttaatgtcat      2220
gataataatg gtttcttaga cgtcaggtgg cacttttcgg ggaaatgtgc gcggaacccc      2280
tatttgttta ttttttctaaa tacattcaaa tatgtatccg ctcatgagac aataaccctg      2340
ataaatgctt caataatatt gaaaaaggaa gagtatgagt attcaacatt tccgtgtcgc      2400
ccttattccc ttttttgcgg cattttgcct tcctgttttt gctcacccag aaacgctggt      2460
gaaagtaaaa gatgctgaag atcagttggg tgcacgagtg ggttacatcg aactggatct      2520
caacagcggt aagatccttg agagttttcg ccccgaagaa cgttttccaa tgatgagcac      2580
ttttaaagtt ctgctatgtg gcgcggtatt atcccgtatt gacgccgggc aagagcaact      2640
cggtcgccgc atacactatt ctcagaatga cttggttgag tactcaccag tcacagaaaa      2700
gcatcttacg gatggcatga cagtaagaga attatgcagt gctgccataa ccatgagtga      2760
taacactgcg gccaacttac ttctgacaac gatcggagga ccgaaggagc taaccgcttt      2820
tttgcacaac atgggggatc atgtaactcg ccttgatcgt tgggaaccgg agctgaatga      2880
agccatacca aacgacgagc gtgacaccac gatgcctgta gcaatggcaa caacgttgcg      2940
caaactatta actggcgaac tacttactct agcttcccgg caacaattaa tagactggat      3000
ggaggcggat aaagttgcag gaccacttct gcgctcggcc cttccggctg gctggtttat      3060
tgctgataaa tctggagccg gtgagcgtgg gtctcgcggt atcattgcag cactggggcc      3120
agatggtaag ccctcccgta tcgtagttat ctacacgacg gggagtcagg caactatgga      3180
tgaacgaaat agacagatcg ctgagatagg tgcctcactg attaagcatt ggtaactgtc      3240
agaccaagtt tactcatata tactttagat tgatttaaaa cttcattttt aatttaaaag      3300
gatctaggtg aagatccttt ttgataatct catgaccaaa atcccttaac gtgagttttc      3360
gttccactga gcgtcagacc ccgtagaaaa gatcaaagga tcttcttgag atccttttttt      3420 tctgcgcgta atctgctgct tgcaaacaaa aaaaccaccg ctaccagcgg tggtttgttt      3480
```

```
gccggatcaa gagctaccaa ctcttttttcc gaaggtaact ggcttcagca gagcgcagat   3540
accaaatact gttcttctag tgtagccgta gttaggccac cacttcaaga actctgtagc   3600
accgcctaca tacctcgctc tgctaatcct gttaccagtg gctgctgcca gtggcgataa   3660
gtcgtgtctt accgggttgg actcaagacg atagttaccg gataaggcgc agcggtcggg   3720
ctgaacgggg ggttcgtgca cacagcccag cttggagcga acgacctaca ccgaactgag   3780
atacctacag cgtgagctat gagaaagcgc cacgcttccc gaagggagaa aggcggacag   3840
gtatccggta agcggcaggg tcggaacagg agagcgcacg agggagcttc caggggggaaa   3900
cgcctggtat ctttatagtc ctgtcgggtt tcgccacctc tgacttgagc gtcgattttt   3960
gtgatgctcg tcagggggc ggagcctatg gaaaaacgcc agcaacgcgg cctttttacg   4020
gttcctggcc ttttgctggc cttttgctca catgttcttt cctgcgttat cccctgattc   4080
tgtggataac cgtattaccg cctttgagtg agctgatacc gctcgccgca gccgaacgac   4140
cgagcgcagc gagtcagtga gcgaggaagc ggaagagcgc ccaatacgca aaccgcctct   4200
ccccgcgcgt tggccgattc attaatgcag ctggcacgac aggtttcccg actggaaagc   4260
gggcagtgag cgcaacgcaa ttaatgtgag ttagctcact cattaggcac cccaggcttt   4320
acactttatg cttccggctc gtatgttgtg tggaattgtg agcggataac aatttcacac   4380
aggaaacagc tatgaccatg attacgccaa gctctcgaga tctag                   4425
```

<210> SEQ ID NO 28
<211> LENGTH: 4465
<212> TYPE: DNA
<213> ORGANISM: Artificial Sequence
<220> FEATURE:
<223> OTHER INFORMATION: Synthetic Polynucleotide

<400> SEQUENCE: 28

```
aaagcttccc gggggatct gggccactcc ctctctgcgc gctcgctcgc tcactgaggc    60
cgggcgacca aggtcgccc gacgcccggg cttttgcccgg gcggcctcag tgagcgagcg   120
agcgcgcaga gagggagtgg ccaactccat cactaggggt tcctggaggg gtggagtcgt   180
gacctaggca tatgccaagt acgccccta ttgacgtcaa tgacggtaaa tggcccgcct   240
ggcattatgc ccagtacatg accttatggg actttcctac ttggcagtac atctacgtat   300
tagtcatcgc tattaccatg gtgatgcggt tttggcagta catcaatggg cgtggatagc   360
ggtttgactc acggggattt ccaagtctcc accccattga cgtcaatggg agtttgtttt   420
ggcaccaaaa tcaacgggac tttccaaaat gtcgtaacaa ctccgcccca ttgacgcaaa   480
tgggcggtag gcgtgtacgg tgggaggtct atataagcag agctcgttta gtgaaccgtc   540
agatcgcctg gagacgccat ccggactcta aggtaaatat aaaattttta agtgtataat   600
gtgttaaact actgattcta attgtttctc tcttttagat tccaacccttt ggaactgaat   660
tccgcgggcc cgggatccac cggtcgccac catggtgagc aagggcgagg agctgttcac   720
cggggtggtg cccatcctgg tcgagctgga cggcgacgta aacggccaca agttcagcgt   780
gtccggcgag ggcgagggcg atgccaccta cggcaagctg accctgaagt tcatctgcac   840
caccggcaag ctgcccgtgc cctggcccac cctcgtgacc accctgacct acggcgtgca   900
gtgcttcagc cgctaccccg accacatgaa gcagcacgac ttcttcaagt ccgccatgcc   960
cgaaggctac gtccaggagc gcaccatctt cttcaaggac gacggcaact acaagacccg  1020
cgccgaggtg aagttcgagg gcgacaccct ggtgaaccgc atcgagctga agggcatcga  1080
cttcaaggag gacggcaaca tcctggggca caagctggag tacaactaca acagccacaa  1140
```

```
cgtctatatc atggccgaca agcagaagaa cggcatcaag gtgaacttca agatccgcca    1200
caacatcgag gacggcagcg tgcagctcgc cgaccactac cagcagaaca cccccatcgg    1260
cgacggcccc gtgctgctgc ccgacaacca ctacctgagc acccagtccg ccctgagcaa    1320
agaccccaac gagaagcgcg atcacatggt cctgctggag ttcgtgaccg ccgccgggat    1380
cactctcggc atggacgagc tgtacaagta aagcggccgc taggcctcac ctgcgatctc    1440
gatgctttat ttgtgaaatt tgtgatgcta ttgctttatt tgtaaccatt ataagctgca    1500
ataaacaagt taacaacaac aattgcattc attttatgtt tcaggttcag ggggaggtgt    1560
gggaggtttt ttaaatcgat tttagggtta gggttagggt tagggaaaaa tttagggtta    1620
gggttagggt tagggaaaaa tttagggtta gggttagggt tagggaaaaa actagtccac    1680
tccctctctg cgcgctcgct cgctcactga ggccgggcga ccaaaggtcg cccgacgccc    1740
gggctttgcc cggcggcct cagtgagcga gcgagcgcgc agagagggac agatccgggc    1800
ccgcatgcgt cgacaattca ctggccgtcg ttttacaacg tcgtgactgg gaaaaccctg    1860
gcgttaccca acttaatcgc cttgcagcac atccccettt cgccagctgg cgtaatagcg    1920
aagaggcccg caccgatcgc ccttcccaac agttgcgcag cctgaatggc gaatggcgcc    1980
tgatgcggta ttttctcctt acgcatctgt gcggtatttc acaccgcata tggtgcactc    2040
tcagtacaat ctgctctgat gccgcatagt taagccagcc ccgacacccg ccaacacccg    2100
ctgacgcgcc ctgacgggct tgtctgctcc cggcatccgc ttacagacaa gctgtgaccg    2160
tctccgggag ctgcatgtgt cagaggtttt caccgtcatc accgaaacgc gcgagacgaa    2220
agggcctcgt gatacgccta ttttatagg ttaatgtcat gataataatg gtttcttaga    2280
cgtcaggtgg cacttttcgg ggaaatgtgc gcggaacccc tatttgttta ttttctaaa    2340 tacattcaaa tatgtatccg ctcatgagac aataaccctg ataaatgctt caataatatt    2400
gaaaaaggaa gagtatgagt attcaacatt tccgtgtcgc ccttattccc ttttttgcgg    2460
cattttgcct tcctgttttt gctcacccag aaacgctggt gaaagtaaaa gatgctgaag    2520
atcagttggg tgcacgagtg ggttacatcg aactggatct caacagcggt aagatccttg    2580
agagttttcg ccccgaagaa cgttttccaa tgatgagcac ttttaaagtt ctgctatgtg    2640
gcgcggtatt atcccgtatt gacgccgggc aagagcaact cggtcgccgc atacactatt    2700
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atggggatc    2880 atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct gcgctcggcc cttccggctg gctggtttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
ccgtagaaaa gatcaaagga tcttcttgag atcctttttt tctgcgcgta atctgctgct    3480
```

| | |
|---|---:|
| tgcaaacaaa aaaaccaccg ctaccagcgg tggtttgttt gccggatcaa gagctaccaa | 3540 |
| ctcttttttcc gaaggtaact ggcttcagca gagcgcagat accaaatact gttcttctag | 3600 |
| tgtagccgta gttaggccac cacttcaaga actctgtagc accgcctaca tacctcgctc | 3660 |
| tgctaatcct gttaccagtg gctgctgcca gtggcgataa gtcgtgtctt accgggttgg | 3720 |
| actcaagacg atagttaccg gataaggcgc agcggtcggg ctgaacgggg ggttcgtgca | 3780 |
| cacagcccag cttggagcga acgacctaca ccgaactgag atacctacag cgtgagctat | 3840 |
| gagaaagcgc cacgcttccc gaagggagaa aggcggacag gtatccggta agcggcaggg | 3900 |
| tcggaacagg agagcgcacg agggagcttc caggggaaa cgcctggtat ctttatagtc | 3960 |
| ctgtcgggtt cgccacctc tgacttgagc gtcgattttt gtgatgctcg tcaggggggc | 4020 |
| ggagcctatg gaaaaacgcc agcaacgcgg ccttttacg gttcctggcc ttttgctggc | 4080 |
| cttttgctca catgttcttt cctgcgttat ccctgattc tgtggataac cgtattaccg | 4140 |
| cctttgagtg agctgatacc gctcgccgca gccgaacgac cgagcgcagc gagtcagtga | 4200 |
| gcgaggaagc ggaagagcgc ccaatacgca aaccgcctct ccccgcgcgt tggccgattc | 4260 |
| attaatgcag ctggcacgac aggtttcccg actggaaagc gggcagtgag cgcaacgcaa | 4320 |
| ttaatgtgag ttagctcact cattaggcac cccaggcttt acactttatg cttccggctc | 4380 |
| gtatgttgtg tggaattgtg agcggataac aatttcacac aggaaacagc tatgaccatg | 4440 |
| attacgccaa gctctcgaga tctag | 4465 |

<210> SEQ ID NO 29
<211> LENGTH: 4405
<212> TYPE: DNA
<213> ORGANISM: Artificial Sequence
<220> FEATURE:
<223> OTHER INFORMATION: Synthetic Polynucleotide

<400> SEQUENCE: 29

| | |
|---|---:|
| aaagcttccc gggggatct gggccactcc ctctctgcgc gctcgctcgc tcactgaggc | 60 |
| cgggcgacca aggtcgccc gacgcccggg ctttgcccgg gcggcctcag tgagcgagcg | 120 |
| agcgcgcaga gagggagtgg ccaactccat cactaggggt tcctggaggg gtggagtcgt | 180 |
| gacctaggca tatgccaagt acgccccta ttgacgtcaa tgacggtaaa tggcccgcct | 240 |
| ggcattatgc ccagtacatg acctttatggg actttcctac ttggcagtac atctacgtat | 300 |
| tagtcatcgc tattaccatg gtgatgcggt tttggcagta catcaatggg cgtggatagc | 360 |
| ggtttgactc acggggattt ccaagtctcc accccattga cgtcaatggg agtttgtttt | 420 |
| ggcaccaaaa tcaacgggac tttccaaaat gtcgtaacaa ctccgcccca ttgacgcaaa | 480 |
| tgggcggtag gcgtgtacgg tgggaggtct atataagcag agctcgttta gtgaaccgtc | 540 |
| agatcgcctg gagacgccat ccggactcta aggtaaatat aaaattttta gtgtataat | 600 |
| gtgttaaact actgattcta attgtttctc tcttttagat tccaacccttt ggaactgaat | 660 |
| tccgcgggcc cgggatccac cggtcgccac catggtgagc aagggcgagg agctgttcac | 720 |
| cggggtggtg cccatcctgg tcgagctgga cggcgacgta aacggccaca agttcagcgt | 780 |
| gtccggcgag ggcgagggcg atgccaccta cggcaagctg accctgaagt tcatctgcac | 840 |
| caccggcaag ctgcccgtgc cctggcccac cctcgtgacc accctgacct acggcgtgca | 900 |
| gtgcttcagc cgctacccc accacatgaa gcagcacgac ttcttcaagt ccgccatgcc | 960 |
| cgaaggctac gtccaggagc gcaccatctt cttcaaggac gacggcaact acaagacccg | 1020 |
| cgccgaggtg aagttcgagg gcgacaccct ggtgaaccgc atcgagctga agggcatcga | 1080 |

| | |
|---|---|
| cttcaaggag gacggcaaca tcctggggca caagctggag tacaactaca acagccacaa | 1140 |
| cgtctatatc atggccgaca agcagaagaa cggcatcaag gtgaacttca agatccgcca | 1200 |
| caacatcgag gacggcagcg tgcagctcgc cgaccactac cagcagaaca cccccatcgg | 1260 |
| cgacggcccc gtgctgctgc ccgacaacca ctacctgagc acccagtccg ccctgagcaa | 1320 |
| agacccaac gagaagcgcg atcacatggt cctgctggag ttcgtgaccg ccgccgggat | 1380 |
| cactctcggc atggacgagc tgtacaagta aagcggccgc taggcctcac ctgcgatctc | 1440 |
| gatgctttat tgtgaaaatt tgtgatgcta ttgctttatt tgtaaccatt ataagctgca | 1500 |
| ataaacaagt taacaacaac aattgcattc attttatgtt tcaggttcag ggggaggtgt | 1560 |
| gggaggtttt ttaaatcgat tttagggtta gggttagggt tagggaaaaa actagtccac | 1620 |
| tccctctctg cgcgctcgct cgctcactga ggccgggcga ccaaaggtcg cccgacgccc | 1680 |
| gggctttgcc cgggcggcct cagtgagcga gcgagcgcgc agagagggac agatccgggc | 1740 |
| ccgcatgcgt cgacaattca ctggccgtcg ttttacaacg tcgtgactgg gaaaaccctg | 1800 |
| gcgttaccca acttaatcgc cttgcagcac atcccccttt cgccagctgg cgtaatagcg | 1860 |
| aagaggcccg caccgatcgc ccttcccaac agttgcgcag cctgaatggc gaatggcgcc | 1920 |
| tgatgcggta ttttctcctt acgcatctgt gcggtatttc acaccgcata tggtgcactc | 1980 |
| tcagtacaat ctgctctgat gccgcatagt taagccagcc ccgacacccg ccaacacccg | 2040 |
| ctgacgcgcc ctgacgggct tgtctgctcc cggcatccgc ttacagacaa gctgtgaccg | 2100 |
| tctccgggag ctgcatgtgt cagaggtttt caccgtcatc accgaaacgc gcgagacgaa | 2160 |
| agggcctcgt gatacgccta ttttataagg ttaatgtcat gataataatg gtttcttaga | 2220 |
| cgtcaggtgg cacttttcgg ggaaatgtgc gcggaacccc tatttgttta ttttctaaa | 2280 |
| tacattcaaa tatgtatccg ctcatgagac aataaccctg ataaatgctt caataatatt | 2340 |
| gaaaaaggaa gagtatgagt attcaacatt tccgtgtcgc ccttattccc ttttttgcgg | 2400 |
| cattttgcct tcctgttttt gctcacccag aaacgctggt gaaagtaaaa gatgctgaag | 2460 |
| atcagttggg tgcacgagtg ggttacatcg aactggatct caacagcggt aagatccttg | 2520 |
| agagttttcg ccccgaagaa cgttttccaa tgatgagcac ttttaaagtt ctgctatgtg | 2580 |
| gcgcggtatt atcccgtatt gacgccgggc aagagcaact cggtcgccgc atacactatt | 2640 |
| ctcagaatga cttggttgag tactcaccag tcacagaaaa gcatcttacg gatggcatga | 2700 |
| cagtaagaga attatgcagt gctgccataa ccatgagtga taacactgcg gccaacttac | 2760 |
| ttctgacaac gatcggagga ccgaaggagc taaccgcttt tttgcacaac atggggatc | 2820 |
| atgtaactcg ccttgatcgt tgggaaccgg agctgaatga agccatacca aacgacgagc | 2880 |
| gtgacaccac gatgcctgta gcaatggcaa caacgttgcg caaactatta actggcgaac | 2940 |
| tacttactct agcttcccgg caacaattaa tagactggat ggaggcggat aaagttgcag | 3000 |
| gaccacttct gcgctcggcc cttccggctg gctggtttat tgctgataaa tctggagccg | 3060 |
| gtgagcgtgg gtctcgcggt atcattgcag cactggggcc agatggtaag ccctcccgta | 3120 |
| tcgtagttat ctacacgacg gggagtcagg caactatgga tgaacgaaat agacagatcg | 3180 |
| ctgagatagg tgcctcactg attaagcatt ggtaactgtc agaccaagtt tactcatata | 3240 |
| tactttagat tgatttaaaa cttcattttt aatttaaaag gatctaggtg aagatccttt | 3300 |
| ttgataatct catgaccaaa atcccttaac gtgagttttc gttccactga gcgtcagacc | 3360 |
| ccgtagaaaa gatcaaagga tcttcttgag atcctttttt tctgcgcgta atctgctgct | 3420 |

| | |
|---|---|
| tgcaaacaaa aaaaccaccg ctaccagcgg tggtttgttt gccggatcaa gagctaccaa | 3480 |
| ctcttttttcc gaaggtaact ggcttcagca gagcgcagat accaaatact gttcttctag | 3540 |
| tgtagccgta gttaggccac cacttcaaga actctgtagc accgcctaca tacctcgctc | 3600 |
| tgctaatcct gttaccagtg gctgctgcca gtggcgataa gtcgtgtctt accgggttgg | 3660 |
| actcaagacg atagttaccg gataaggcgc agcggtcggg ctgaacgggg ggttcgtgca | 3720 |
| cacagcccag cttggagcga acgacctaca ccgaactgag ataccacag cgtgagctat | 3780 |
| gagaaagcgc cacgcttccc gaagggagaa aggcggacag gtatccggta gcggcaggg | 3840 |
| tcggaacagg agagcgcacg agggagcttc caggggaaa cgcctggtat ctttatagtc | 3900 |
| ctgtcgggtt tcgccacctc tgacttgagc gtcgatttt gtgatgctcg tcagggggc | 3960 |
| ggagcctatg gaaaaacgcc agcaacgcgg cctttttacg gttcctggcc ttttgctggc | 4020 |
| cttttgctca catgttcttt cctgcgttat cccctgattc tgtggataac cgtattaccg | 4080 |
| cctttgagtg agctgatacc gctcgccgca gccgaacgac cgagcgcagc gagtcagtga | 4140 |
| gcgaggaagc ggaagagcgc ccaatacgca aaccgcctct ccccgcgcgt tggccgattc | 4200 |
| attaatgcag ctggcacgac aggtttcccg actggaaagc gggcagtgag cgcaacgcaa | 4260 |
| ttaatgtgag ttagctcact cattaggcac cccaggcttt acactttatg cttccggctc | 4320 |
| gtatgttgtg tggaattgtg agcggataac aatttcacac aggaaacagc tatgaccatg | 4380 |
| attacgccaa gctctcgaga tctag | 4405 |

<210> SEQ ID NO 30
<211> LENGTH: 4465
<212> TYPE: DNA
<213> ORGANISM: Artificial Sequence
<220> FEATURE:
<223> OTHER INFORMATION: Synthetic Polynucleotide

<400> SEQUENCE: 30

| | |
|---|---|
| aaagcttccc gggggatct gggccactcc ctctctgcgc gctcgctcgc tcactgaggc | 60 |
| cgggcgacca aggtcgccc gacgcccggg ctttgcccgg gcggcctcag tgagcgagcg | 120 |
| agcgcgcaga gagggagtgg ccaactccat cactaggggt tcctggaggg gtggagtcgt | 180 |
| gacctaggtt tagggttagg gttagggtta gggaaaaatt tagggttagg gttagggtta | 240 |
| gggaaaaatt tagggttagg gttagggtta gggaaaaacc taggcatatg ccaagtacgc | 300 |
| cccctattga cgtcaatgac ggtaaatggc ccgcctggca ttatgcccag tacatgacct | 360 |
| tatgggactt tcctacttgg cagtacatct acgtattagt catcgctatt accatggtga | 420 |
| tgcggttttg gcagtacatc aatgggcgtg gatagcggtt tgactcacgg ggatttccaa | 480 |
| gtctccaccc cattgacgtc aatgggagtt tgttttggca ccaaaatcaa cgggactttc | 540 |
| caaaatgtcg taacaactcc gccccattga cgcaaatggg cggtaggcgt gtacggtggg | 600 |
| aggtctatat aagcagagct cgtttagtga accgtcagat cgcctggaga cgccatccgg | 660 |
| actctaaggt aaatataaaa ttttaagtg tataatgtgt taaactactg attctaattg | 720 |
| tttctctctt ttagattcca acctttggaa ctgaattccg cgggcccggg atccaccggt | 780 |
| cgccaccatg gtgagcaagg gcgaggagct gttcaccggg gtggtgccca tcctggtcga | 840 |
| gctggacggc gacgtaaacg gccacaagtt cagcgtgtcc ggcgagggcg agggcgatgc | 900 |
| cacctacggc aagctgaccc tgaagttcat ctgcaccacc ggcaagctgc ccgtgccctg | 960 |
| gcccaccctc gtgaccaccc tgacctacgg cgtgcagtgc ttcagccgct accccgacca | 1020 |
| catgaagcag cacgacttct tcaagtccgc catgcccgaa ggctacgtcc aggagcgcac | 1080 |

```
catcttcttc aaggacgacg gcaactacaa gacccgcgcc gaggtgaagt tcgagggcga    1140
caccctggtg aaccgcatcg agctgaaggg catcgacttc aaggaggacg gcaacatcct    1200
ggggcacaag ctggagtaca actacaacag ccacaacgtc tatatcatgg ccgacaagca    1260
gaagaacggc atcaaggtga acttcaagat ccgccacaac atcgaggacg gcagcgtgca    1320
gctcgccgac cactaccagc agaacacccc catcggcgac ggccccgtgc tgctgcccga    1380
caaccactac ctgagcaccc agtccgccct gagcaaagac cccaacgaga gcgcgatca    1440 catggtcctg ctggagttcg tgaccgccgc cgggatcact ctcggcatgg acgagctgta    1500
caagtaaagc ggccgctagg cctcacctgc gatctcgatg ctttatttgt gaaatttgtg    1560
atgctattgc tttatttgta accattataa gctgcaataa acaagttaac aacaacaatt    1620
gcattcattt tatgtttcag gttcaggggg aggtgtggga ggtttttaa actagtccac    1680 tccctctctg cgcgctcgct cgctcactga ggccgggcga ccaaaggtcg cccgacgccc    1740
gggctttgcc cggcggcct cagtgagcga gcgagcgcgc agagagggac agatccgggc    1800
ccgcatgcgt cgacaattca ctggccgtcg ttttacaacg tcgtgactgg gaaaaccctg    1860
gcgttaccca acttaatcgc cttgcagcac atccccctt cgccagctgg cgtaatagcg    1920
aagaggcccg caccgatcgc ccttcccaac agttgcgcag cctgaatggc gaatggcgcc    1980
tgatgcggta ttttctcctt acgcatctgt gcggtatttc acaccgcata tggtgcactc    2040
tcagtacaat ctgctctgat gccgcatagt taagccagcc ccgacacccg ccaacacccg    2100
ctgacgcgcc ctgacgggct tgtctgctcc cggcatccgc ttacagacaa gctgtgaccg    2160
tctccgggag ctgcatgtgt cagaggtttt caccgtcatc accgaaacgc gcgagacgaa    2220
agggcctcgt gatacgccta ttttatagg ttaatgtcat gataaatg gtttcttaga    2280 cgtcaggtgg cacttttcgg ggaaatgtgc gcggaacccc tatttgttta ttttctaaa    2340 tacattcaaa tatgtatccg ctcatgagac aataaccctg ataatgctt caataatatt    2400 gaaaaaggaa gagtatgagt attcaacatt tccgtgtcgc ccttattccc tttttgcgg    2460 cattttgcct tcctgttttt gctcacccag aaacgctggt gaaagtaaaa gatgctgaag    2520
atcagttggg tgcacgagtg ggttacatcg aactggatct caacagcggt aagatccttg    2580
agagttttcg ccccgaagaa cgttttccaa tgatgagcac ttttaaagtt ctgctatgtg    2640
gcgcggtatt atcccgtatt gacgccggc aagagcaact cggtcgccgc atacactatt    2700
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atggggatc    2880 atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct gcgctcggcc cttccggctg gctggttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
```

| | |
|---|---|
| ccgtagaaaa gatcaaagga tcttcttgag atccttttt tctgcgcgta atctgctgct | 3480 |
| tgcaaacaaa aaaaccaccg ctaccagcgg tggtttgttt gccggatcaa gagctaccaa | 3540 |
| ctcttttcc gaaggtaact ggcttcagca gagcgcagat accaaatact gttcttctag | 3600 |
| tgtagccgta gttaggccac cacttcaaga actctgtagc accgcctaca tacctcgctc | 3660 |
| tgctaatcct gttaccagtg gctgctgcca gtggcgataa gtcgtgtctt accgggttgg | 3720 |
| actcaagacg atagttaccg gataaggcgc agcggtcggg ctgaacgggg gttcgtgca | 3780 |
| cacagcccag cttggagcga acgacctaca ccgaactgag atacctacag cgtgagctat | 3840 |
| gagaaagcgc cacgcttccc gaagggagaa aggcggacag gtatccggta agcggcaggg | 3900 |
| tcggaacagg agagcgcacg agggagcttc caggggaaa cgcctggtat ctttatagtc | 3960 |
| ctgtcgggtt tcgccacctc tgacttgagc gtcgattttt gtgatgctcg tcagggggc | 4020 |
| ggagcctatg gaaaaacgcc agcaacgcgg cctttttacg gttcctggcc ttttgctggc | 4080 |
| ctttgctca catgttcttt cctgcgttat ccctgattc tgtggataac cgtattaccg | 4140 |
| cctttgagtg agctgatacc gctcgccgca gccgaacgac cgagcgcagc gagtcagtga | 4200 |
| gcgaggaagc ggaagagcgc ccaatacgca aaccgcctct ccccgcgcgt tggccgattc | 4260 |
| attaatgcag ctggcacgac aggtttcccg actggaaagc gggcagtgag cgcaacgcaa | 4320 |
| ttaatgtgag ttagctcact cattaggcac cccaggcttt acactttatg cttccggctc | 4380 |
| gtatgttgtg tggaattgtg agcggataac aatttcacac aggaaacagc tatgaccatg | 4440 |
| attacgccaa gctctcgaga tctag | 4465 |

<210> SEQ ID NO 31
<211> LENGTH: 4435
<212> TYPE: DNA
<213> ORGANISM: Artificial Sequence
<220> FEATURE:
<223> OTHER INFORMATION: Synthetic Polynucleotide

<400> SEQUENCE: 31

| | |
|---|---|
| aaagcttccc gggggatct gggccactcc ctctctgcgc gctcgctcgc tcactgaggc | 60 |
| cgggcgacca aggtcgccc gacgcccggg ctttgcccgg gcggcctcag tgagcgagcg | 120 |
| agcgcgcaga gagggagtgg ccaactccat cactaggggt tcctggaggg gtggagtcgt | 180 |
| gacctaggca tatgccaagt acgccccta ttgacgtcaa tgacggtaaa tggcccgcct | 240 |
| ggcattatgc ccagtacatg accttatggg actttcctac ttggcagtac atctacgtat | 300 |
| tagtcatcgc tattaccatg gtgatgcggt tttggcagta catcaatggg cgtggatagc | 360 |
| ggtttgactc acggggattt ccaagtctcc accccattga cgtcaatggg agtttgtttt | 420 |
| ggcaccaaaa tcaacgggac tttccaaaat gtcgtaacaa ctccgcccca ttgacgcaaa | 480 |
| tgggcggtag gcgtgtacgg tgggaggtct atataagcag agctcgttta gtgaaccgtc | 540 |
| agatcgcctg gagacgccat ccggactcta aggtaaatat aaaattttta agtgtataat | 600 |
| gtgttaaact actgattcta attgtttctc tcttttagat tccaaccttt ggaactgaat | 660 |
| tccgcgggcc cgggatccac cggtcgccac catggtgagc aagggcgagg agctgttcac | 720 |
| cggggtggtg cccatcctgg tcgagctgga cggcgacgta aacggccaca gttcagcgt | 780 |
| gtccggcgag ggcgagggcg atgccaccta cggcaagctg accctgaagt tcatctgcac | 840 |
| caccggcaag ctgcccgtgc cctggcccac cctcgtgacc accctgacct acggcgtgca | 900 |
| gtgcttcagc cgctacccg accacatgaa gcagcacgac ttcttcaagt ccgccatgcc | 960 |
| cgaaggctac gtccaggagc gcaccatctt cttcaaggac gacggcaact acaagacccg | 1020 |

```
cgccgaggtg aagttcgagg gcgacaccct ggtgaaccgc atcgagctga agggcatcga      1080
cttcaaggag gacggcaaca tcctggggca caagctggag tacaactaca cagccacaa      1140 cgtctatatc atggccgaca gcagaagaa cggcatcaag gtgaacttca agatccgcca      1200
caacatcgag gacggcagcg tgcagctcgc cgaccactac cagcagaaca cccccatcgg      1260
cgacggcccc gtgctgctgc ccgacaacca ctacctgagc acccagtccg ccctgagcaa      1320
agaccccaac gagaagcgcg atcacatggt cctgctggag ttcgtgaccg ccgccgggat      1380
cactctcggc atggacgagc tgtacaagta aagcggccgc taggcctcac ctgcgatctc      1440
gatgctttat ttgtgaaatt tgtgatgcta ttgctttatt tgtaaccatt ataagctgca      1500
ataaacaagt taacaacaac aattgcattc attttatgtt tcaggttcag ggggaggtgt      1560
gggaggtttt taaatcgat gctagatgtt agcgtaaaaa gctagatgtt agcgtaaaaa      1620
gctagatgtt agcgtaaaaa actagtccac tccctctctg cgcgctcgct cgctcactga      1680
ggccgggcga ccaaaggtcg cccgacgccc gggctttgcc cgggcggcct cagtgagcga      1740
gcgagcgcgc agagagggac agatccgggc ccgcatgcgt cgacaattca ctggccgtcg      1800
ttttacaacg tcgtgactgg gaaaaccctg gcgttaccca acttaatcgc cttgcagcac      1860
atcccccttt cgccagctgg cgtaatagcg aagaggcccg caccgatcgc ccttcccaac      1920
agttgcgcag cctgaatggc gaatggcgcc tgatgcggta ttttctcctt acgcatctgt      1980
gcggtatttc acaccgcata tggtgcactc tcagtacaat ctgctctgat gccgcatagt      2040
taagccagcc ccgacacccg ccaacacccg ctgacgcgcc ctgacgggct tgtctgctcc      2100
cggcatccgc ttacagacaa gctgtgaccg tctccgggag ctgcatgtgt cagaggtttt      2160
caccgtcatc accgaaacgc gcgagacgaa agggcctcgt gatacgccta ttttttatagg      2220 ttaatgtcat gataataatg gtttcttaga cgtcaggtgg cacttttcgg ggaaatgtgc      2280
gcggaacccc tatttgttta ttttttctaaa tacattcaaa tatgtatccg ctcatgagac      2340
aataaccctg ataaatgctt caataatatt gaaaaaggaa gagtatgagt attcaacatt      2400
tccgtgtcgc ccttattccc ttttttgcgg cattttgcct tcctgttttt gctcacccag      2460
aaacgctggt gaaagtaaaa gatgctgaag atcagttggg tgcacgagtg ggttacatcg      2520
aactggatct caacagcggt aagatccttg agagttttcg ccccgaagaa cgttttccaa      2580
tgatgagcac ttttaaagtt ctgctatgtg gcgcggtatt atcccgtatt gacgccgggc      2640
aagagcaact cggtcgccgc atacactatt ctcagaatga cttggttgag tactcaccag      2700
tcacagaaaa gcatcttacg gatggcatga cagtaagaga attatgcagt gctgccataa      2760
ccatgagtga taacactgcg gccaacttac ttctgacaac gatcggagga ccgaaggagc      2820
taaccgcttt tttgcacaac atgggggatc atgtaactcg ccttgatcgt tgggaaccgg      2880
agctgaatga agccatacca aacgacgagc gtgacaccac gatgcctgta gcaatggcaa      2940
caacgttgcg caaactatta actggcgaac tacttactct agcttcccgg caacaattaa      3000
tagactggat ggaggcggat aaagttgcag gaccacttct gcgctcggcc cttccggctg      3060
gctggtttat tgctgataaa tctggagccg gtgagcgtgg gtctcgcggt atcattgcag      3120
cactggggcc agatggtaag ccctcccgta tcgtagttat ctacacgacg gggagtcagg      3180
caactatgga tgaacgaaat agacagatcg ctgagatagg tgcctcactg attaagcatt      3240
ggtaactgtc agaccaagtt tactcatata ctttagat tgatttaaaa cttcattttt      3300
aatttaaaag gatctaggtg aagatccttt ttgataatct catgaccaaa atcccttaac      3360
```

```
gtgagttttc gttccactga gcgtcagacc ccgtagaaaa gatcaaagga tcttcttgag    3420 atccttttt tctgcgcgta atctgctgct tgcaaacaaa aaaaccaccg ctaccagcgg    3480
tggtttgttt gccggatcaa gagctaccaa ctcttttcc gaaggtaact ggcttcagca    3540
gagcgcagat accaaatact gttcttctag tgtagccgta gttaggccac cacttcaaga    3600
actctgtagc accgcctaca tacctcgctc tgctaatcct gttaccagtg gctgctgcca    3660
gtggcgataa gtcgtgtctt accgggttgg actcaagacg atagttaccg gataaggcgc    3720
agcggtcggg ctgaacgggg ggttcgtgca cacagcccag cttggagcga acgacctaca    3780
ccgaactgag atacctacag cgtgagctat gagaaagcgc cacgcttccc gaagggagaa    3840
aggcggacag gtatccggta agcggcaggg tcggaacagg agagcgcacg agggagcttc    3900 caggggggaaa cgcctggtat ctttatagtc ctgtcgggtt tcgccacctc tgacttgagc    3960 gtcgatttt gtgatgctcg tcagggggc ggagcctatg gaaaaacgcc agcaacgcgg    4020
cctttttacg gttcctggcc ttttgctggc cttttgctca catgttcttt cctgcgttat    4080
cccctgattc tgtggataac cgtattaccg cctttgagtg agctgatacc gctcgccgca    4140
gccgaacgac cgagcgcagc gagtcagtga gcgaggaagc ggaagagcgc ccaatacgca    4200
aaccgcctct ccccgcgcgt tggccgattc attaatgcag ctggcacgac aggttttccg    4260
actggaaagc gggcagtgag cgcaacgcaa ttaatgtgag ttagctcact cattaggcac    4320
cccaggcttt acactttatg cttccggctc gtatgttgtg tggaattgtg agcggataac    4380
aatttcacac aggaaacagc tatgaccatg attacgccaa gctctcgaga tctag    4435
```

<210> SEQ ID NO 32
<211> LENGTH: 6940
<212> TYPE: DNA
<213> ORGANISM: Artificial Sequence
<220> FEATURE:
<223> OTHER INFORMATION: Synthetic Polynucleotide

<400> SEQUENCE: 32

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagcg gcctcggcct ctgcataaat aaaaaaaatt agtcagccat gagcttggcc     240
cattgcatac gttgtatcca tatcataata tgtacattta tattggctca tgtccaacat     300
taccgccatg ttgacattga ttattgacta gttattaata gtaatcaatt acggggtcat     360
tagttcatag cccatatatg gagttccgcg ttacataact tacggtaaat ggcccgcctg     420
gctgaccgcc caacgacccc cgcccattga cgtcaataat gacgtatgtt cccatagtaa     480
cgccaatagg gactttccat tgacgtcaat gggtggagta tttacggtaa actgcccact     540
tggcagtaca tcaagtgtat catatgccaa gtacgccccc tattgacgtc aatgacggta     600
aatggcccgc ctggcattat gcccagtaca tgaccttatg ggactttcct acttggcagt     660
acatctacgt attagtcatc gctattacca tggtgatgcg gttttggcag tacatcaatg     720
ggcgtggata gcggtttgac tcacggggat ttccaagtct ccaccccatt gacgtcaatg     780
ggagtttgtt ttggcaccaa aatcaacggg actttccaaa atgtcgtaac aactccgccc     840
cattgacgca aatgggcggt aggcgtgtac ggtgggaggt ctatataagc agagctcgtt     900
tagtgaaccg tcagatcgcc tggagacgcc atccacgctg ttttgacctc catagaagac     960
accgggaccg atccagcctc ccctcgaagc tgatcctgag aacttcaggg tgagtctatg    1020
```

```
ggacccttga tgttttcttt cccctcttt tctatggtta agttcatgtc ataggaaggg      1080
gagaagtaac agggtacaca tattgaccaa atcaggataa ttttgcattt gtaattttaa      1140
aaaatgcttt cttcttttaa tatactttt tgtttatctt atttctaata ctttccctaa      1200
tctctttctt tcagggcaat aatgatacaa tgtatcatgc ctctttgcac cattctaaag      1260
aataacagtg ataattctg ggttaaggca atagcaatat ttctgcatat aaatatttct       1320
gcatataaat tgtaactgat gtaagaggtt tcatattgct aatagcagct acaatccagc      1380
taccattctg cttttatttt atggttggga taaggctgga ttattctgag tccaagctag      1440 gccctttgc taatcatgtt catacctctt atcttcctcc cacagctcct gggcaacgtg       1500
ctggtctgtg tgctggccca tcactttggc aaagaattcc gcgggcccgg atccaccgg       1560 tcgccaccat ggtgagcaag ggcgaggagc tgttcaccgg ggtggtgccc atcctggtcg      1620
agctggacgg cgacgtaaac ggccacaagt tcagcgtgtc cggcgagggc gagggcgatg      1680
ccacctacgg caagctgacc ctgaagttca tctgcaccac cggcaagctg cccgtgccct      1740
ggcccaccct cgtgaccacc ctgacctacg gcgtgcagtg cttcagccgc taccccgacc      1800
acatgaagca gcacgacttc ttcaagtccg ccatgcccga aggctacgtc caggagcgca      1860
ccatcttctt caaggacgac ggcaactaca agacccgcgc cgaggtgaag ttcgagggcg      1920
acaccctggt gaaccgcatc gagctgaagg gcatcgactt caaggaggac ggcaacatcc      1980
tggggcacaa gctggagtac aactacaaca gccacaacgt ctatatcatg gccgacaagc      2040
agaagaacgg catcaaggtg aacttcaaga tccgccacaa catcgaggac ggcagcgtgc      2100
agctcgccga ccactaccag cagaacaccc ccatcggcga cggccccgtg ctgctgcccg      2160
acaaccacta cctgagcacc cagtccgccc tgagcaaaga ccccaacgag aagcgcgatc      2220
acatggtcct gctggagttc gtgaccgccg ccgggatcac tctcggcatg gacgagctgt      2280
acaagtaaag cggccgctct agaggatcca agcttatcga taccgtcgac ctcgagggcc      2340
cagatctaat tcaccccacc agtgcaggct gcctatcaga aagtggtggc tggtgtggct      2400
aatgccctgg cccacaagta tcactaagct cgctttcttg ctgtccaatt tctattaaag      2460
gttcctttgt tccctaagtc caactactaa actgggggat attatgaagg gccttgagca      2520
tctggattct gcctaataaa aaacatttat tttcattgca atgatgtatt taaattattt      2580
ctgaatattt tactaaaaag ggaatgtggg aggtcagtgc atttaaaaca taagaaatg      2640 aagagctagt tcaaaccttg ggaaaataca ctatatctta aactccatga agaaggtga      2700 ggctgcaaac agctaatgca cattggcaac agccctgat gcctatgcct tattcatcc      2760 tcagaaaagg attcaagtag aggcttgatt tggaggttaa agttttgcta tgctgtattt      2820
tacattactt attgttttag ctgtcctcat gaatgtcttt tcactaccca tttgcttatc      2880
ctgcatctct cagccttgac tccactcagt tctcttgctt agagatacca cctttcccct      2940
gaagtgttcc ttccatgttt tacgcgaga tggtttctcc tcgcctggcc actcagcctt      3000
agttgtctct gttgtcttat agaggtctac ttgaagaagg aaaaacaggg ggcatggttt      3060
gactgtcctg tgagcccttc ttccctgcct ccccactca cagtgacccg gaatccctcg      3120
acatctagag catggctacg tagataagta gcatggcggg ttaatcatta actacaagga      3180
acccctagtg atggagttgg ccactccctc tctgcgcgct cgctcgctca ctgaggccgg      3240
gcgaccaaag gtcgcccgac gcccgggctt tgccgggcg gcctcagtga gcgagcgagc      3300 gcgcagctg gcgtaatagc gaagaggccc gcaccgatcg cccttcccaa cagttgcgca      3360
```

```
gcctgaatgg cgaatggaat tccagacgat tgagcgtcaa aatgtaggta tttccatgag    3420 cgttttttcct gttgcaatgg ctggcggtaa tattgttctg gatattacca gcaaggccga   3480
tagtttgagt tcttctactc aggcaagtga tgttattact aatcaaagaa gtattgcgac    3540
aacggttaat ttgcgtgatg gacagactct tttactcggt ggcctcactg attataaaaa   3600
cacttctcag gattctggcg taccgttcct gtctaaaatc cctttaatcg gcctcctgtt   3660
tagctcccgc tctgattcta acgaggaaag cacgttatac gtgctcgtca aagcaaccat   3720
agtacgcgcc ctgtagcggc gcattaagcg cggcgggtgt ggtggttacg cgcagcgtga   3780
ccgctacact tgccagcgcc ctagcgcccg ctcctttcgc tttcttccct tcctttctcg   3840
ccacgttcgc cggctttccc cgtcaagctc taaatcgggg gctcccttta gggttccgat   3900
ttagtgcttt acggcacctc gaccccaaaa aacttgatta gggtgatggt tcacgtagtg   3960
ggccatcgcc ctgatagacg ttttttcgcc ctttgacgtt ggagtccacg ttctttaata   4020
gtggactctt gttccaaact ggaacaacac tcaaccctat ctcggtctat tcttttgatt   4080
tataagggat tttgccgatt tcggcctatt ggttaaaaaa tgagctgatt taacaaaaat   4140
ttaacgcgaa ttttaacaaa atattaacgt ttacaattta atatttgct tatacaatct    4200 tcctgttttt ggggcttttc tgattatcaa ccggggtaca tatgattgac atgctagttt   4260
tacgattacc gttcatcgat tctcttgttt gctccagact ctcaggcaat gacctgatag   4320
cctttgtaga gacctctcaa aaatagctac cctctccggc atgaatttat cagctagaac   4380
ggttgaatat catattgatg gtgatttgac tgtctccggc cttctcaccc gtttgaatc    4440 tttacctaca cattactcag gcattgcatt taaaatatat gagggttcta aaaatttttta  4500 tccttgcgtt gaaataaagg cttctcccgc aaaagtatta cagggtcata atgttttttgg  4560 tacaaccgat ttagctttat gctctgaggc tttattgctt aattttgcta attctttgcc   4620
ttgcctgtat gatttattgg atgttggaat tcctgatgcg gtattttctc cttacgcatc   4680
tgtgcggtat ttcacaccgc atatggtgca ctctcagtac aatctgctct gatgccgcat   4740
agttaagcca gccccgacac ccgccaacac ccgctgacgc gccctgacgg gcttgtctgc   4800
tcccggcatc cgcttacaga caagctgtga ccgtctccgg gagctgcatg tgtcagaggt   4860
tttcaccgtc atcaccgaaa cgcgcgagac gaaagggcct cgtgatacgc ctatttttat   4920
aggttaatgt catgataata atggtttctt agacgtcagg tggcactttt cggggaaatg   4980
tgcgcggaac ccctatttgt ttatttttct aaatacattc aaatatgtat ccgctcatga   5040
gacaataacc ctgataaatg cttcaataat attgaaaaag gaagagtatg agtattcaac   5100
atttccgtgt cgcccttatt cccttttttg cggcattttg ccttcctgtt tttgctcacc   5160
cagaaacgct ggtgaaagta aaagatgctg aagatcagtt gggtgcacga gtgggttaca   5220
tcgaactgga tctcaacagc ggtaagatcc ttgagagttt tcgccccgaa gaacgttttc   5280
caatgatgag cacttttaaa gttctgctat gtggcgcggt attatcccgt attgacgccg   5340
ggcaagagca actcggtcgc cgcatacact attctcagaa tgacttggtt gagtactcac   5400
cagtcacaga aaagcatctt acggatggca tgacagtaag agaattatgc agtgctgcca   5460
taaccatgag tgataacact gcggccaact tacttctgac aacgatcgga ggaccgaagg   5520
agctaaccgc ttttttgcac aacatggggg atcatgtaac tcgccttgat cgttgggaac   5580
cggagctgaa tgaagccata ccaaacgacg agcgtgacac cacgatgcct gtagcaatgg   5640
caacaacgtt gcgcaaacta ttaactggcg aactacttac tctagcttcc cggcaacaat   5700
taatagactg gatggaggcg gataaagttg caggaccact tctgcgctcg gcccttccgg   5760
```

```
ctggctggtt tattgctgat aaatctggag ccggtgagcg tgggtctcgc ggtatcattg    5820
cagcactggg gccagatggt aagccctccc gtatcgtagt tatctacacg acggggagtc    5880
aggcaactat ggatgaacga aatagacaga tcgctgagat aggtgcctca ctgattaagc    5940
attggtaact gtcagaccaa gtttactcat atatacttta gattgattta aaacttcatt    6000
tttaatttaa aaggatctag gtgaagatcc ttttgataa tctcatgacc aaaatccctt    6060
aacgtgagtt ttcgttccac tgagcgtcag acccgtaga aaagatcaaa ggatcttctt    6120
gagatccttt ttttctgcgc gtaatctgct gcttgcaaac aaaaaaacca ccgctaccag    6180
cggtggtttg tttgccggat caagagctac caactctttt tccgaaggta actggcttca    6240
gcagagcgca gataccaaat actgtccttc tagtgtagcc gtagttaggc caccacttca    6300
agaactctgt agcaccgcct acatacctcg ctctgctaat cctgttacca gtggctgctg    6360
ccagtggcga taagtcgtgt cttaccgggt tggactcaag acgatagtta ccggataagg    6420
cgcagcggtc gggctgaacg gggggttcgt gcacacagcc cagcttggag cgaacgacct    6480
acaccgaact gagataccta cagcgtgagc tatgagaaag cgccacgctt cccgaaggga    6540
gaaaggcgga caggtatccg gtaagcggca gggtcggaac aggagagcgc acgagggagc    6600 ttccagggg aaacgcctgg tatctttata gtcctgtcgg gtttcgccac ctctgacttg    6660
agcgtcgatt tttgtgatgc tcgtcagggg gcggagcct atggaaaaac gccagcaacg    6720 cggcctttt acggttcctg ccttttgct ggccttttgc tcacatgttc tttcctgcgt    6780 tatccctga ttctgtggat aaccgtatta ccgcctttga gtgagctgat accgctcgcc    6840
gcagccgaac gaccgagcgc agcgagtcag tgagcgagga agcggaagag cgcccaatac    6900
gcaaaccgcc tctccccgcg cgttggccga ttcattaatg    6940
```

<210> SEQ ID NO 33
<211> LENGTH: 7257
<212> TYPE: DNA
<213> ORGANISM: Artificial Sequence
<220> FEATURE:
<223> OTHER INFORMATION: Synthetic Polynucleotide

<400> SEQUENCE: 33

```
cagcagctgc gcgctcgctc gctcactgag gccgcccggg caaagcccgg gcgtcgggcg     60
acctttggtc gcccggcctc agtgagcgag cgagcgcgca gagagggagt ggccaactcc    120
atcactaggg gttccttgta gttaatgatt aacccgccat gctacttatc tacgtagcca    180
tgctctagcg gcctcggcct ctgcataaat aaaaaaaatt agtcagccat gagcttggcc    240
cattgcatac gttgtatcca tatcataata tgtacattta tattggctca tgtccaacat    300
taccgccatg ttgacattga ttattgacta gttattaata gtaatcaatt acgggtcat    360 tagttcatag cccatatatg gagttccgcg ttacataact tacggtaaat ggcccgcctg    420
gctgaccgcc caacgacccc cgcccattga cgtcaataat gacgtatgtt cccatagtaa    480
cgccaatagg gactttccat tgacgtcaat gggtggagta tttacggtaa actgcccact    540
tggcagtaca tcaagtgtat catatgccaa gtacgccccc tattgacgtc aatgacggta    600
aatggcccgc ctggcattat gcccagtaca tgaccttatg gactttcct acttggcagt    660 acatctacgt attagtcatc gctattacca tggtgatgcg gttttggcag tacatcaatg    720
ggcgtggata gcggtttgac tcacggggat ttccaagtct ccaccccatt gacgtcaatg    780
ggagtttgtt ttggcaccaa aatcaacggg actttccaaa atgtcgtaac aactccgccc    840
```

```
cattgacgca aatgggcggt aggcgtgtac ggtgggaggt ctatataagc agagctcgtt    900
tagtgaaccg tcagatcgcc tggagacgcc atccacgctg ttttgacctc catagaagac    960
accgggaccg atccagcctc ccctcgaagc tgatcctgag aacttcaggg tgagtctatg   1020
ggacccttga tgttttcttt ccccttcttt tctatggtta agttcatgtc ataggaaggg   1080
gagaagtaac agggtacaca tattgaccaa atcagggtaa ttttgcattt gtaattttaa   1140
aaaatgcttt cttcttttaa tatacttttt tgtttatctt atttctaata ctttccctaa   1200
tctctttctt tcagggcaat aatgatacaa tgtatcatgc ctctttgcac cattctaaag   1260
aataacagtg ataatttctg ggttaaggca atagcaatat ttctgcatat aaatatttct   1320
gcatataaat tgtaactgat gtaagaggtt tcatattgct aatagcagct acaatccagc   1380
taccattctg cttttatttt atggttggga taaggctgga ttattctgag tccaagctag   1440
gcccttttgc taatcatgtt catacctctt atcttcctcc cacagctcct gggcaacgtg   1500
ctggtctgtg tgctggccca tcactttggc aaagaattcc gcgggccgg gatccaccgg   1560 tcgccaccat ggtgagcaag ggcgaggagc tgttcaccgg ggtggtgccc atcctggtcg   1620
agctggacgg cgacgtaaac ggccacaagt tcagcgtgtc cggcgagggc gagggcgatg   1680
ccacctacgg caagctgacc ctgaagttca tctgcaccac cggcaagctg cccgtgccct   1740
ggcccaccct cgtgaccacc ctgacctacg gcgtgcagtg cttcagccgc taccccgacc   1800
acatgaagca gcacgacttc ttcaagtccg ccatgcccga aggctacgtc caggagcgca   1860
ccatcttctt caaggacgac ggcaactaca agacccgcgc cgaggtgaag ttcgagggcg   1920
acaccctggt gaaccgcatc gagctgaagg gcatcgactt caaggaggac ggcaacatcc   1980
tggggcacaa gctggagtac aactacaaca gccacaacgt ctatatcatg gccgacaagc   2040
agaagaacgg catcaaggtg aacttcaaga tccgccacaa catcgaggac ggcagcgtgc   2100
agctcgccga ccactaccag cagaacaccc ccatcggcga cggccccgtg ctgctgcccg   2160
acaaccacta cctgagcacc cagtccgccc tgagcaaaga ccccaacgag aagcgcgatc   2220
acatggtcct gctggagttc gtgaccgccg ccgggatcac tctcggcatg gacgagctgt   2280
acaagtaaag cggccgctct agaggatcca agcttatcga taccgtcgac ctcgagggcc   2340
cagatctaat tcaccccacc agtgcaggct gcctatcaga aagtggtggc tggtgtggct   2400
aatgccctgg cccacaagta tcactaagct cgctttcttg ctgtccaatt tctattaaag   2460
gttcctttgt tccctaagtc caactactaa actgggggat attatgaagg gccttgagca   2520
tctggattct gcctaataaa aaacatttat tttcattgca atgatgtatt taaattattt   2580
ctgaatattt tactaaaaag ggaatgtggg aggtcagtgc atttaaaaca taagaaaatg   2640
aagagctagt tcaaaccttg ggaaaataca ctatatctta aactccatga agaaggtga    2700 ggctgcaaac agctaatgca cattggcaac agcccctgat gcctatgcct tattcatccc   2760
tcagaaaagg attcaagtag aggcttgatt tggaggttaa agttttgcta tgctgtattt   2820
tacattactt attgttttag ctgtcctcat gaatgtcttt tcactaccca tttgcttatc   2880
ctgcatctct cagccttgac tccactcagt tctcttgctt agagatacca cctttcccct   2940
gaagtgttcc ttccatgttt tacgcgaga tggtttctcc tcgcctggcc actcagcctt   3000
agttgtctct gttgtcttat agaggtctac ttgaagaagg aaaaacaggg gcatggtttt   3060
gactgtcctg tgagcccttc ttccctgcct cccccactca cagtgacccg gaatccctcg   3120
acaggtacct ttagggttag ggttagggtt agggaaaaat ttagggttag ggttagggtt   3180
agggaaaaat ttagggttag ggttagggtt agggaaaaat ttagggttag ggttagggtt   3240
```

```
agggaaaaat ttagggttag ggttagggtt agggaaaaac cctaacccta accctaaccc   3300
taaatttttt ccctaacccT aaccctaacc ctaaatttTt tccctaaccc taaccctaac   3360
cctaaatttt ttccctaacc ctaacccTaa ccctaaattt tttccctaac cctaaccCTa   3420
accctaaatt ttttgctagc tctagagcat ggctacgtag ataagtagca tggcgggtta   3480
atcattaact acaaggaacc cctagtgatg gagttggcca ctccctctct gcgcgctcgc   3540
tcgctcactg aggccgggcg accaaaggtc gcccgacgcc cgggctttgc ccgggcggcc   3600
tcagtgagcg agcgagcgcg ccagctggcg taatagcgaa gaggcccgca ccgatcgccc   3660
ttcccaacag ttgcgcagcc tgaatggcga atggaattcc agacgattga gcgtcaaaat   3720
gtaggtattt ccatgagcgt ttttcctgtt gcaatggctg gcggtaatat tgttctggat   3780
attaccagca aggccgatag tttgagttct tctactcagg caagtgatgt tattactaat   3840
caaagaagta ttgcgacaac ggttaatttg cgtgatggac agactctttt actcggtggc   3900
ctcactgatt ataaaaacac ttctcaggat tctggcgtac cgttcctgtc taaaatccct   3960
ttaatcggcc tcctgtttag ctcccgctct gattctaacg aggaaagcac gttatacgtg   4020
ctcgtcaaag caaccatagt acgcgccctg tagcggcgca ttaagcgcgg cgggtgtggt   4080
ggttacgcgc agcgtgaccg ctacacttgc cagcgcccta gcgcccgctc ctttcgcttt   4140
cttcccttcc tttctcgcca cgttcgccgg ctttccccgt caagctctaa atcgggggct   4200
ccctttaggg ttccgattta gtgctttacg gcacctcgac cccaaaaaac ttgattaggg   4260
tgatggttca cgtagtgggc catcgccctg atagacggtt tttcgccctt tgacgttgga   4320
gtccacgttc tttaatagtg gactcttgtt ccaaactgga acaacactca accctatctc   4380
ggtctattct tttgatttat aagggatttt gccgatttcg gcctattggt taaaaaatga   4440
gctgatttaa caaaaattta cgcgaatttt aacaaaata ttaacgttta caatttaaat   4500
atttgcttat acaatcttcc tgttttTggg cttttctga ttatcaaccg ggtacatat   4560
gattgacatg ctagttttac gattaccgtt catcgattct cttgtttgct ccagactctc   4620
aggcaatgac ctgatagcct ttgtagagac ctctcaaaaa tagctaccct ctccggcatg   4680
aatttatcag ctagaacggt tgaatatcat attgatggtg atttgactgt ctccggcctt   4740
tctcacccgt ttgaatcttt acctacacat tactcaggca ttgcatttaa aatatatgag   4800
ggttctaaaa atttttatcc ttgcgttgaa ataaggcTt ctcccgcaaa agtattacag   4860
ggtcataatg ttttTggtac aaccgattTa gctttatgct ctgaggcttt attgcttaat   4920
tttgctaatt ctttgccTtg cctgtatgat ttattggatg ttggaattcc tgatgcggta   4980
ttttctcctt acgcatctgt gcggtatttc acaccgcata tggtgcactc tcagtacaat   5040
ctgctctgat gccgcatagt taagccagcc ccgacacccg ccaacacccg ctgacgcgcc   5100
ctgacgggct tgtctgctcc cggcatccgc ttacagacaa gctgtgaccg tctccgggag   5160
ctgcatgtgt cagaggtttt caccgtcatc accgaaacgc gcgagacgaa agggcctcgt   5220
gatacgccta ttttTatagg ttaatgtcat gataataatg gtttcttaga cgtcaggtgg   5280
cacttttcgg ggaaatgtgc gcggaacccc tatttgttta ttttTctaaa tacattcaaa   5340
tatgtatccg ctcatgagac aataaccctg ataaatgctt caataatatt gaaaaggaa   5400
gagtatgagt attcaacatt tccgtgtcgc ccttattccc ttttttgcgg cattttgcct   5460
tcctgttttt gctcacccag aaacgctggt gaaagtaaaa gatgctgaag atcagttggg   5520
tgcacgagtg ggttacatcg aactggatct caacagcggt aagatccttg agagttttcg   5580
```

```
ccccgaagaa cgttttccaa tgatgagcac ttttaaagtt ctgctatgtg gcgcggtatt    5640
atcccgtatt gacgccgggc aagagcaact cggtcgccgc atacactatt ctcagaatga    5700
cttggttgag tactcaccag tcacagaaaa gcatcttacg gatggcatga cagtaagaga    5760
attatgcagt gctgccataa ccatgagtga taacactgcg gccaacttac ttctgacaac    5820
gatcggagga ccgaaggagc taaccgcttt tttgcacaac atgggggatc atgtaactcg    5880
ccttgatcgt tgggaaccgg agctgaatga agccatacca aacgacgagc gtgacaccac    5940
gatgcctgta gcaatggcaa caacgttgcg caaactatta actggcgaac tacttactct    6000
agcttcccgg caacaattaa tagactggat ggaggcggat aaagttgcag gaccacttct    6060
gcgctcggcc cttccggctg gctggtttat tgctgataaa tctggagccg gtgagcgtgg    6120
gtctcgcggt atcattgcag cactggggcc agatggtaag ccctcccgta tcgtagttat    6180
ctacacgacg gggagtcagg caactatgga tgaacgaaat agacagatcg ctgagatagg    6240
tgcctcactg attaagcatt ggtaactgtc agaccaagtt tactcatata ctttagat    6300 tgatttaaaa cttcattttt aatttaaaag gatctaggtg aagatccttt ttgataatct    6360
catgaccaaa atcccttaac gtgagttttc gttccactga gcgtcagacc ccgtagaaaa    6420
gatcaaagga tcttcttgag atcctttttt tctgcgcgta atctgctgct tgcaaacaaa    6480
aaaaccaccg ctaccagcgg tggtttgttt gccggatcaa gagctaccaa ctctttttcc    6540
gaaggtaact ggcttcagca gagcgcagat accaaatact gtccttctag tgtagccgta    6600
gttaggccac cacttcaaga actctgtagc accgcctaca tacctcgctc tgctaatcct    6660
gttaccagtg gctgctgcca gtggcgataa gtcgtgtctt accgggttgg actcaagacg    6720
atagttaccg gataaggcgc agcggtcggg ctgaacgggg ggttcgtgca cacagcccag    6780
cttggagcga acgacctaca ccgaactgag atacctacag cgtgagctat gagaaagcgc    6840
cacgcttccc gaagggagaa aggcggacag gtatccggta agcggcaggg tcggaacagg    6900
agagcgcacg agggagcttc cagggggaaa cgcctggtat ctttatagtc ctgtcgggtt    6960
tcgccacctc tgacttgagc gtcgattttt gtgatgctcg tcaggggggc ggagcctatg    7020
gaaaaacgcc agcaacgcgg cctttttacg gttcctggcc ttttgctggc cttttgctca    7080
catgttcttt cctgcgttat cccctgattc tgtggataac cgtattaccg cctttgagtg    7140
agctgatacc gctcgccgca gccgaacgac cgagcgcagc gagtcagtga gcgaggaagc    7200
ggaagagcgc ccaatacgca aaccgcctct ccccgcgcgt tggccgattc attaatg      7257
```

<210> SEQ ID NO 34
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 34

```
gctagatgtt agcgt                                                       15
```

ENGINEERED VIRAL VECTOR REDUCES INDUCTION OF INFLAMMATORY AND IMMUNE RESPONSES

RELATED APPLICATION DATA

This application claims priority to U.S. Provisional Application No. 62/347,302 filed on Jun. 8, 2016, which is hereby incorporated herein by reference in its entirety for all purposes.

This invention was made with government support under HG008525 awarded by National Institutes of Health. The government has certain rights in the invention.

TECHNICAL FIELD OF THE INVENTION

This invention is related to the area of viral based therapies. In particular, it relates to recombinant viruses.

BACKGROUND OF THE INVENTION

Gene therapy has immense potential to prevent, treat, and cure multiple human diseases [1]. In 2012, Glybera™ (alipogene tiparvovec) became the first viral gene therapy to be approved for use in the western world [2]. Glybera™ utilizes adeno-associated virus (AAV) as a viral vector to deliver the human lipoprotein lipase (LPL) gene to muscle cells in patients with LPL deficiency [3]. Many AAV clinical trials are currently underway or being planned in the U.S. and the EU [4-6].

AAV is a small, non-enveloped virus that packages a single-stranded linear DNA genome that is approximately 5 kb long, and has been adapted for use as a gene transfer vehicle [4]. The coding regions of AAV are flanked by inverted terminal repeats (ITRs), which act as the origins for DNA replication and serve as the primary packaging signal [7, 8]. Both positive and negative strands are packaged into virions equally well and capable of infection [9-11]. In addition, a small deletion in one of the two ITRs allows packaging of self-complementary vectors, in which the genome self-anneals after viral uncoating. This results in more efficient transduction of cells but reduces the coding capacity by half [12, 13]. While AAV is not associated with any human disease, >70% of humans are seropositive for one or most serotypes [14, 15]. Typical routes of administration for AAV vectors include intravenous, intramuscular, subretinal and intracranal injections. AAV gene therapy is most often used to deliver a wild-type gene to treat monogenic diseases, and AAV vectors have been used to transduce cells in the liver, skeletal and cardiac muscle, retina and central nervous system [16-26]. In addition, there is now growing interest in using AAV to deliver CRISPR-Cas9 gene editing or to deliver broadly neutralizing antibodies against infectious diseases such as human immunodeficiency virus (HIV) and influenza A virus [27-32].

Despite several advances in gene therapy, a key concern is the inflammatory response elicited by the viral vector [33, 34]. This is best illustrated by a highly publicized case in 1999 when Jesse Gelsinger died four days after gene therapy with adenovirus in a clinical trial due to excessive inflammation [35]. While AAV has been shown to elicit much weaker inflammation in comparison to adenoviruses [36, 37], Glybera™ therapy still includes twelve weeks of immunosuppression, beginning three days before Glybera™ administration [38]. These immunosuppressive and anti-inflammatory drugs (cyclosporine A, mycophenolate mofetil, and methylprednisolone) compromise the patient's immune system during treatment, and all patients still developed neutralizing antibodies against AAV capsid, precluding future re-administration. Furthermore, many AAV gene therapy clinical trials do not utilize immunosuppression prophylactically and only administer corticosteroids upon signs of inflammation or tissue damage, which has been associated with variable therapeutic efficacy [22, 23]. Interestingly, in agreement with their ability to trigger inflammatory and immune responses, AAV vectors have also been developed as vaccine vehicles against infectious diseases and cancer [39-41].

Inflammation has been implicated as a critical determinant of successful AAV-mediated transgene expression. A study found that following AAV administration in mice, artificially inducing systemic inflammation such as the upregulation of tumor necrosis factor (TNF), led to a decline in transgene expression in the liver [42]. This indicates that immunological tolerance to AAV-encoded transgene can be broken given sufficient inflammatory responses. Another study characterized inflammation in the murine liver following AAV infection and found transient increases in liver enzymes in the serum, and also liver pathology consistent with portal and lobular inflammation [43]. Strikingly, the authors observed that the use of AAVrh.32.33 viruses, which induced higher liver enzymes than other tested AAV serotypes, also led to a decline in transgene expression to below detection levels, again suggesting that inflammatory and immune responses are associated with poor transgene expression.

In hemophilia B clinical trials, it has been observed that a subset of patients exhibited elevated liver enzymes, and this transient transaminitis was accompanied by declining levels of transgene-encoded factor IX [22, 23]. A tapering course of corticosteroid therapy was used on a patient with transaminitis, which subsequently normalized aminotransferase levels in the serum and rescued further decline of factor IX expression. Overall, these observations are compatible with immune-mediated destruction of AAV-transduced hepatocytes and demonstrate that inflammatory and immune responses triggered by AAV administration are a safety concern and can hamper therapeutic efficacy in humans. Thus, it would be advantageous to develop viral vectors that intrinsically evade eliciting inflammation. Furthermore, instead of systemic immunosuppression with drugs, it would be beneficial to avoid triggering specific immune responses.

It has been previously shown that the DNA genome of AAV is sensed by Toll-like receptor 9 (TLR9) during AAV's entry into the cell through the endocytic pathway [36, 44]. TLR9 is a pattern recognition receptor (PRR) found on endosomal membranes of immune cells such as B cells, monocytes, macrophages and plasmacytoid dendritic cells, and binds to unmethylated CpG motifs found in the AAV genome [45, 46]. This leads to TLR9 dimerization, which triggers a cascade of signal transduction that activates NF-kB (also known as p52-RelA complex) and induces type I interferons (IFNs). NF-kB in turn drives the transcriptional upregulation of multiple proinflammatory cytokines such as TNF leading to inflammation and immune cell recruitment, while secreted IFNs induce the expression of numerous interferon-stimulated genes (ISGs) and establish an antiviral state. Importantly, genetic ablation of TLR9 in mice abolishes induction of inflammatory cytokines upon AAV treatment in the liver, and also reduces formation of antibodies and T cells against AAV [36]. Thus, TLR9 plays a critical role in stimulating an early inflammatory and innate immune response during AAV infection, which also contributes to priming adaptive immunity. Finally, two other pattern recognition receptors, TLR2 and TLR4, have been implicated in triggering responses to AAV structural proteins [47, 48].

In the TLR9 field, a commonly used tool to block TLR9 activation in cell culture is short, single-stranded DNA oligonucleotides that bind TLR9 but do not activate it [49, 50]. Several such sequences are known—some synthetic and others derived from organisms—and they often bear no sequence homology [51-59]. Structural studies have revealed how an inhibitory oligonucleotide binds TLR9 tightly but does not trigger TLR9 dimerization, which is required for TLR9 activation and downstream signaling [60]. In addition to binding TLR9 directly to antagonize its activation, other mechanisms to block TLR9 activation or TLR9-mediated inflammation have been postulated or shown for other TLR9-inhibitory oligonucleotides [reviewed in 49]. These include competing for receptor-mediated endocytosis or phagocytosis, inhibition of TLR9 trafficking or TLR9 processing into a functionally active product, inhibition of endosomal acidification or activity of key proteases in endosomes, or blocking signaling proteins downstream of TLR9. When these inhibitory oligonucleotides are supplied in trans with TLR9 ligands (such as a DNA virus, or a CpG-containing oligonucleotide) in cell culture media, they are endocytosed and can bind to TLR9, preventing its activation by stimulatory ligands. Supplementation of inhibitory oligonucleotides in trans is widely adopted in immunology experiments, but it is unknown in the field if incorporation of these sequences into a viral genome allows it to evade eliciting inflammatory and immune responses.

While AAV has been shown to elicit much weaker inflammatory responses in comparison to adenoviruses, Glybera™ alipogene tiparvovec treatment still includes twelve weeks of immunosuppression, beginning three days before Glybera™ alipogene tiparvovec administration. These immunosuppressive drugs strongly hamper T cell activation and therefore compromise the patient's immune system during treatment. It would be advantageous to engineer viral vectors that evade and elicit diminished or no inflammatory response upon administration. Furthermore, it would be beneficial if the immune suppression was not systemic, and if it was transient. Preventing inflammatory and immune responses could also improve transgene expression and may allow the re-administration of the viral vector for future purposes.

There is a continuing need in the art to improve the efficacy of viral vectors for therapy and for in vivo production of biological products.

SUMMARY OF THE INVENTION

According to one aspect of the invention a nucleic acid molecule is provided. It comprises a viral genome covalently linked to an inhibitory nucleic acid sequence which binds to TLR9 but does not trigger TLR9 activation.

According to another aspect a recombinant virus is provided for delivery of a desired function to a mammalian cell. The recombinant virus comprises a viral genome covalently linked to an inhibitory nucleic acid sequence which binds to TLR9 but does not trigger TLR9 activation.

Another embodiment is an aspect of treating a mammal. The method comprises administering a recombinant virus to a mammal in need thereof. The recombinant virus comprises a viral genome covalently linked to an inhibitory nucleic acid sequence which binds to TLR9 but does not trigger TLR9 activation.

Still another aspect is a method of making a viral genome of a recombinant virus. An inhibitory nucleic acid sequence is inserted into a viral genome. The inhibitory nucleic acid sequence binds to TLR9 but does not trigger TLR9 activation.

According to one aspect a nucleic acid molecule is provided. It comprises an inverted terminal repeat (ITR) and a nucleic acid sequence which inhibits TLR9-mediated inflammation.

Another aspect of the invention is a nucleic acid molecule. The molecule comprises a viral genome covalently linked to an inhibitory nucleic acid sequence which inhibits TLR9-mediated inflammation.

Yet another aspect of the invention is a recombinant virus for delivery of a desired function to a mammalian cell. The recombinant virus comprises a viral genome comprising an inhibitory nucleic acid sequence which inhibits TLR9-mediated inflammation.

Still another aspect of the invention is a method of making a viral genome of a recombinant virus. A nucleic acid sequence is inserted into a viral genome. The nucleic acid sequence inhibits TLR9-mediated inflammation.

According to another aspect of the invention a nucleic acid vector is provided. The vector comprises at least one nucleic acid sequence. The nucleic acid sequence is capable of inhibiting TLR9-mediated inflammation.

Another aspect of the invention is a method of reducing immunogenicity of a modified virus having a genome. The method comprises inserting a nucleic acid sequence into the genome. The nucleic acid sequence inhibits TLR9-mediated inflammation. The modified virus causes a reduced inflammatory response in a host as compared to a virus that does not contain the inhibitory sequence.

Still another aspect of the invention is a method of increasing expression in a host cell of a virally introduced transgene. The method comprises introducing into a host a modified virus having a genome. The genome comprises a nucleic acid sequence. The nucleic acid sequence inhibits TLR9-mediated inflammation. The modified virus results in higher transgene expression in a host cell as compared to a virus that does not contain the inhibitory sequence.

Yet another aspect of the invention is a composition comprising a viral capsid encapsidating a nucleic acid sequence that inhibits TLR9-mediated inflammation.

These and other aspects and embodiments which will be apparent to those of skill in the art upon reading the specification provide the art with tools for better treating mammals with viral vectors and virions and for better using viral vectors and virions for producing products of transgenes in host cells, host tissues, and host animals.

Any and all of the above described aspects may be combined with any of the following features.

The viral genome may be adeno-associated virus (AAV) genome.

The viral genome may be selected from the group consisting of adenovirus, herpes simplex virus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, and human parvovirus B19.

The viral genome may be single stranded.

The viral genome may be packaged in a virion.

The viral genome may comprise a gene which may be expressible in a human cell.

The viral genome may be a cytotoxic virus for lysing target tumor cells.

The inhibitory nucleic acid sequence may comprise c41 oligonucleotide sequence TGGCGCGCACCCACGGCCTG (SEQ ID NO: 1).

The inhibitory nucleic acid sequence may comprise a plurality of copies of c41 sequence (SEQ ID NO: 1).

The inhibitory nucleic acid sequence may comprise two copies of c41 sequence (SEQ ID NO: 1) separated by a linker sequence.

The linker sequence is AAAAA (SEQ ID NO: 8).

The inhibitory nucleic acid sequence may be selected from the group consisting of:

```
                                       (SEQ ID NO: 2)
ODN 2088: TCC TGG CGG GGA AGT;

(SEQ ID NO: 3)
ODN 4084-F: CCTGGATGGGAA;

(SEQ ID NO: 4)
ODN INH-1: CCTGGATGGGAATTCCCATCCAGG;

(SEQ ID NO: 5)
ODN INH-18: CCT GGA TGG GAA CTT ACC GCT GCA;

(SEQ ID NO: 6)
ODN TTAGGG: TT AGG GTT AGG GTT AGG GTT AGG G;
and (SEQ ID NO: 7)
G-ODN: CTC CTA TTG GGG GTT TCC TAT.
```

The inhibitory nucleic acid sequence may be a bacterial sequence.

The viral genome, recombinant virus, vector, or nucleic acid sequence may comprise a non-human gene.

The inhibitory nucleic acid sequence may be inserted downstream of or in a 3' untranslated region of the viral genome.

The viral genome may be covalently linked to the inhibitory nucleic acid sequence by a phosphodiester bond.

The viral genome, recombinant virus, vector, or nucleic acid sequence may comprise a detectable marker.

The detectable marker may be inducible.

The inhibitory nucleic acid sequence may comprise a human telomere sequence shown in SEQ ID NO: 9.

The viral genome may be self-complementary.

The viral genome may be covalently linked to a plurality of inhibitory nucleic acid sequences.

The plurality of inhibitory nucleic acid sequences may comprise an inhibitory sequence and its reverse complement.

The inhibitory nucleic acid sequence may comprise three copies of c41 sequence (SEQ ID NO: 1), each copy separated by a linker sequence.

The inhibitory nucleic acid sequence may be selected from the group consisting of:

```
                                      (SEQ ID NO: 16)
ODN 2114: TCCTGGAGGGGAAGT;

(SEQ ID NO: 17)
ODN 4024: TCCTGGATGGGAAGT;

(SEQ ID NO: 18)
ODN INH-4: TTCCCATCCAGGCCTGGATGGGAA;

(SEQ ID NO: 19)
ODN INH-13: CTTACCGCTGCACCTGGATGGGAA;

(SEQ ID NO: 20)
ODN Poly-G: GGGGGGGGGGGGGGGGGGGG;

(SEQ ID NO: 21)
ODN GpG: TGACTGTGAAGGTTAGAGATGA;

(SEQ ID NO: 22)
ODN IRS-869: TCCTGGAGGGGTTGT;

(SEQ ID NO: 23)
ODN IRS-954: TGCTCCTGGAGGGGTTGT;
and (SEQ ID NO: 24)
ODN 21158: CCTGGCGGGG.
```

The inhibitory nucleic acid sequence may be ODN TTAGGG (SEQ ID NO: 6).

The inhibitory sequence may be covalently linked to a linker.

The inhibitory sequence may be upstream of the linker.

The inhibitory nucleic acid sequence may comprise a plurality of copies of ODN TTAGGG (SEQ ID NO: 6).

The plurality of copies of ODN TTAGGG (SEQ ID NO: 6) may each be separated by a linker.

The inhibitory nucleic acid sequence may comprise at least 2, at least 3, at least 4, or at least 5 copies of ODN TTAGGG (SEQ ID NO: 6), each copy separated by a linker.

The inhibitory nucleic acid sequence may be a human sequence.

The viral genome, recombinant virus, vector, or nucleic acid sequence may comprise a non-human nucleic acid sequence.

The viral genome, recombinant virus, vector, or nucleic acid sequence may comprise a human gene.

The viral genome, recombinant virus, vector, or nucleic acid sequence may comprise a human nucleic acid sequence.

The inhibitory nucleic acid sequence may be inserted in the 5' untranslated region of the viral genome.

The inhibitory nucleic acid sequence may be inserted upstream of a promoter of the viral genome.

The viral genome, recombinant virus, vector, or nucleic acid sequence may comprise an inducible promoter.

The inhibitory nucleic acid sequence may comprise two repeated monomers of SEQ ID NO: 1.

The inhibitory nucleic acid sequence may comprise three repeated monomers of SEQ ID NO: 1.

The inhibitory nucleic acid sequence may comprise SEQ ID NO: 6 or SEQ ID NO: 9.

The inhibitory nucleic acid sequence may comprise three repeated monomers of SEQ ID NO: 6 or SEQ ID NO: 9.

The inhibitory nucleic acid sequence may comprise five repeated monomers of SEQ ID NO: 6 or SEQ ID NO: 9.

The step of administering may be repeated.

The viral genome may be packaged in virions.

The step of inserting may utilize a DNA ligase.

The viral genome may be single stranded when in virions.

The viral genome of the recombinant virus may comprise a gene for delivery to and expression in a human cell.

The viral genome, recombinant virus, vector, or nucleic acid sequence may comprise a linker separating each of the nucleic acid sequences.

The viral genome, recombinant virus, vector, or nucleic acid sequence may comprise at least 2, at least 3, at least 4, or at least 5 copies of the nucleic acid sequence.

The inhibitory nucleic acid may be covalently linked to a gene.

The inhibitory nucleic acid sequence may be 95% identical to c41 oligonucleotide sequence TGGCGCGCACC-CACGGCCTG (SEQ ID NO: 1).

The inhibitory nucleic acid sequence may be 95% identical to SEQ ID NO: 9.

The inhibitory nucleic acid sequence may be 95% identical to a sequence selected from the group consisting of:

```
                                      (SEQ ID NO: 2)
ODN 2088: TCC TGG CGG GGA AGT;

(SEQ ID NO: 3)
ODN 4084-F: CCTGGATGGGAA;

(SEQ ID NO: 4)
ODN INH-1: CCTGGATGGGAATTCCCATCCAGG;

(SEQ ID NO: 5)
ODN INH-18: CCT GGA TGG GAA CTT ACC GCT GCA;

(SEQ ID NO: 6)
ODN TTAGGG: TT AGG GTT AGG GTT AGG GTT AGG G;
and (SEQ ID NO: 7)
G-ODN: CTC CTA TTG GGG GTT TCC TAT.
```

The inhibitory nucleic acid sequence may be 95% identical to a sequence selected from the group consisting of:

```
                                     (SEQ ID NO: 16)
ODN 2114: TCCTGGAGGGGAAGT;

(SEQ ID NO: 17)
ODN 4024: TCCTGGATGGGAAGT;

(SEQ ID NO: 18)
ODN INH-4: TTCCCATCCAGGCCTGGATGGGAA;

(SEQ ID NO: 19)
ODN INH-13: CTTACCGCTGCACCTGGATGGGAA;

(SEQ ID NO: 20)
ODN Poly-G: GGGGGGGGGGGGGGGGGGGG;

(SEQ ID NO: 21)
ODN GpG: TGACTGTGAAGGTTAGAGATGA;

(SEQ ID NO: 22)
ODN IRS-869: TCCTGGAGGGGTTGT;

(SEQ ID NO: 23)
ODN IRS-954: TGCTCCTGGAGGGGTTGT;
and (SEQ ID NO: 24)
ODN 21158: CCTGGCGGG.
```

The inhibitory nucleic acid sequence may comprise a plurality of copies of SEQ ID NO: 6 and/or SEQ ID NO: 9

The inhibitory nucleic acid sequence may comprise two copies of SEQ ID NO: 6 and/or SEQ ID NO: 9 separated by a linker sequence.

BRIEF DESCRIPTION OF THE DRAWINGS

FIG. 3A shows nucleotide sequence of c41 (SEQ ID NO: 1), a single-stranded oligonucleotide. FIG. 3B shows organization of AAV-eGFP and AAV-eGFP-c41 genomes. ITR, inverted terminal repeat; LPA, late polyadenylation signal. Transgene of interest depicted in this case is eGFP. The insertion is of c41 sequence. Spacer depicted in FIG. 3B is shown in SEQ ID NO: 8.

FIG. 6A shows nucleotide sequence of "telomere" (SEQ ID NO: 9), a single-stranded oligonucleotide containing the $(TTAGGG)_4$ (SEQ ID NO: 6) motif from mammalian telomeres. FIG. 6B shows organization of AAV-eGFP-telomere genome. The insertion is of "telomere" sequence. Spacers shown in FIG. 6B are SEQ ID NO: 8.

FIG. 7A shows the percentage of transduced cells (GFP+) 2 days after infection of a B cell line with similar amounts of indicated AAV viruses, analyzed by flow cytometry. FIG. 7B shows TNF production in the supernatant of primary human CD14+ monocytes 18 hours after infection, as assayed by ELISA.

FIG. 8A-8B. Engineering a self-complementary AAV vector. (FIG. 8A) DNA sequences of "c41" and "telomere". (FIG. 8B) Genome organization of an AAV vector (scAAV-eGFP) and modified vectors. LpA: polyA signal.

FIG. 9A-9C. Inflammatory response to various AAV vectors in human immune cells in vitro. (FIG. 9A) Primary human macrophages were infected with AAV2 viruses (MOI: $10^5$ vg/cell) and supernatants were collected 18 h later and analyzed by ELISA for TNF levels. Five uM ODN 2006, a CpG-containing oligonucleotide, served as a positive control. (FIG. 9B, FIG. 9C) Primary human CD14+ monocytes from two different donors were infected similar to (A) and analyzed for TNF levels. Data shown are mean±s.d. of n=3 technical replicates. *$P<0.05$ (unpaired t-test) compared to scAAV-eGFP.

FIG. 10A-10E. Further characterization of AAV vectors. (FIG. 10A) DNA sequence of "control". (FIG. 10B) Genome organization of modified vectors. (FIG. 10C) Primary human macrophages were infected with AAV2 viruses similar to (FIG. 9A) and analyzed by ELISA for TNF levels. (FIG. 10D) Primary human monocytes were infected similar to (FIG. 9B, FIG. 9C) and analyzed by ELISA for TNF levels. Data shown (FIG. 10C, FIG. 10D) are mean±s.d. of n=3 technical replicates. *$P<0.05$ (unpaired t-test) compared to scAAV-eGFP. (FIG. 10E) Adult C57BL/6 mice were infected with indicated AAV2 viruses similar to (FIG. 12A, FIG. 12B and FIG. 12C) and a piece of the liver was analyzed for indicated gene expression by qRT-PCR. Data shown are mean±s.d. of n=5 mice per condition except n=3 mice for scAAV-eGFP-3xcontrol. *$P<0.05$ (unpaired t-test) compared to saline condition. N.s.: not significant ($P>0.05$).

(FIG. 11A) Primary human macrophages using a different lot of both AAV2 viruses were infected similar to (FIG. 9A) and analyzed for TNF levels. (FIG. 11B) HeLa cells were infected with AAV2 viruses at indicated MOIs and cells were harvested 48 h later and analyzed by flow cytometry for GFP expression. The percentage of GFP positive cells are shown Data shown are mean±s.d. of n=3 technical replicates. *$P<0.05$ (unpaired t-test) compared to scAAV-eGFP.

FIG. 12A-12C. Inflammatory response to intravenous administration of various AAV vectors in adult mice in vivo. (FIG. 12A, FIG. 12B and FIG. 12C) Adult C57BL/6 mice were infected with indicated AAV2 viruses ($10^{11}$ vg per mouse) by tail vein injections. 2 h later, the animals were euthanized and a piece of the liver was analyzed for indicated gene expression by qRT-PCR. Saline injection was set to 1-fold expression for each gene. Data shown are mean±s.d. of n=3 mice per condition (FIG. 12A) or n=4 mice per condition (FIG. 12B and FIG. 12C). *P<0.05 (unpaired t-test) compared to saline condition. N.s.: not significant (P>0.05).

FIG. 14A-14C. Inflammatory and immune response following subretinal administration of various AAV vectors in neonatal mice in vivo. (FIG. 14A, FIG. 14B and FIG. 14C) Neonatal CD1 mice (P1) received indicated AAV8 viruses ($1.8 \times 10^8$ vg per mouse eye) by subretinal injections. At P21, the animals were euthanized and the eyecup was dissected out. The retina and the rest of the eyecup were analyzed for indicated gene expression by qRT-PCR. Saline injection was set to 1 fold expression for each gene. Each triangle represents an animal. Data shown are n=3 mice (saline) and n=5 mice (each virus) and mean values are indicated.

FIG. 15A-15C. Analysis of immune cell markers in the retina following subretinal administration of various AAV vectors in neonatal mice in vivo. (FIG. 15A, FIG. 15B and FIG. 15C) Similar to (FIG. 14A-14C), the retina was analyzed for indicated gene expression by qRT-PCR. Aif1 (Iba1) is known to be expressed in microglia, while Cd4 and Cd8a are markers of helper and cytolytic T cells respectively. Saline injection was set to 1 fold expression for each gene. Each triangle represents an animal. Data shown are n=3 mice (saline) and n=5 mice (each virus) and mean values are indicated.

FIGS. 17A-17B. FIG. 17A shows nucleotide sequence of c41 (SEQ ID NO: 1), a single-stranded oligonucleotide. FIG. 17B shows organization of AAV-eGFP and AAV-eGFP-c41 genomes. ITR, inverted terminal repeat; LPA, late polyadenylation signal. Transgene of interest depicted in this case is eGFP. The insertion is of c41 sequence. Spacer depicted in FIG. 17B is shown in SEQ ID NO: 8.

FIGS. 18A-18B. FIG. 18A shows nucleotide sequence of "telomere" (SEQ ID NO: 9), a single-stranded oligonucleotide containing the (TTAGGG)$_4$ (SEQ ID NO: 6) motif from mammalian telomeres. FIG. 18B shows organization of AAV-eGFP-telomere genome. The insertion is of "telomere" sequence. Spacers shown in FIG. 18B are SEQ ID NO: 8.

DETAILED DESCRIPTION OF THE INVENTION

Figure 1:
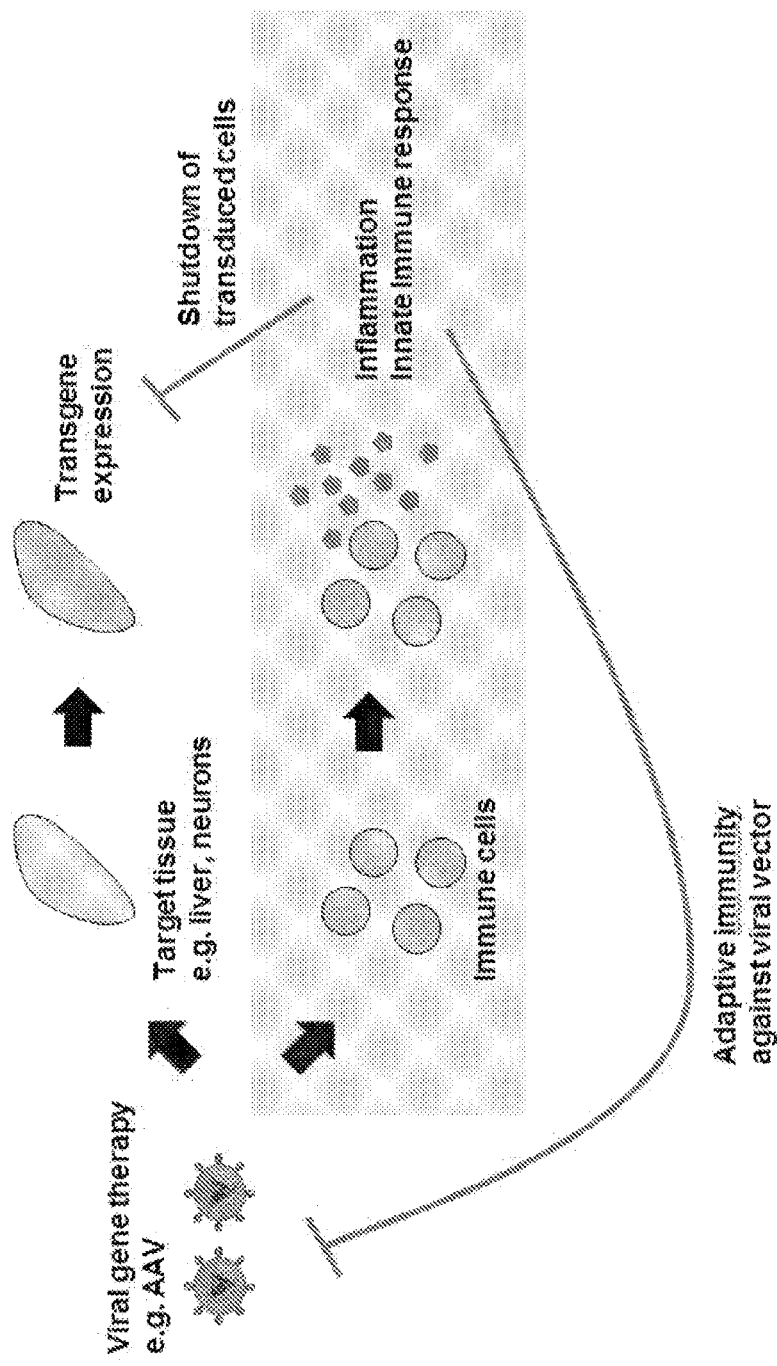
FIG. 1. Schematic drawing of viral gene therapy and inflammatory and immune responses.
Figure 2:
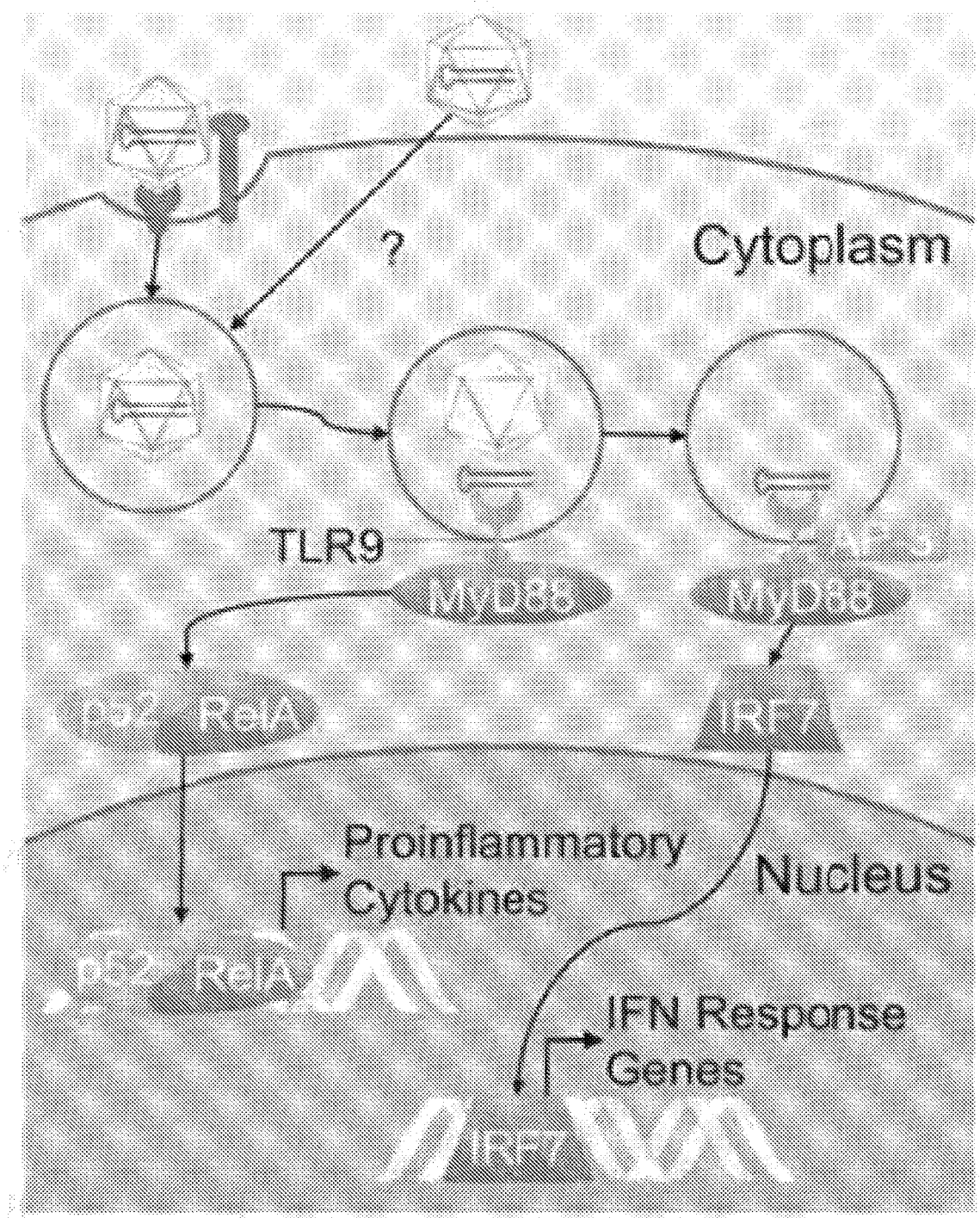
FIG. 2. Schematic drawing showing TLR9 sensing AAV DNA during viral entry and inflammatory and immune responses. From Rogers et al., 2011, *Frontiers in Microbiology*, "Innate Immune Responses to AAV Vectors," vol. 2, article 194.

The inventors have developed viral vectors and virions that harbor their own protection against host immune and inflammatory systems. These vectors and virions carry short nucleic acid sequences which inhibit the activation of toll-like receptor 9 (TLR9), a host protein which activates inflammatory and immune responses in mammalian cells.

A short nucleotide sequence for inhibition of TLR9 may be of any origin. It can be bacterial, human, synthetic, or from other sources. One particular sequence is the 20 nucleotide long "c41" [TGGCGCGCACCCACGGCCTG (SEQ ID NO: 1)] from *Pseudomonas aeruginosa*. Another particular sequence is from human telomeres and comprises (TTAGGG)$_4$ (SEQ ID NO:6). Other inhibitory sequences are shown in SEQ ID NO: 2-5, 7, 9, and 16-24. Inhibitory sequences may also be used which share at least 80% homology/identity with these sequences. Inhibitory sequences may also be used which share at least 85%, at least 90%, at least 95%, at least 96%, at least 97%, at least 98%, and/or at least 99% homology/identity with these sequences. Multiple copies of the inhibitory sequence can be used, either in tandem arrays or separated in the viral vector by spacer or linker sequences or other portions of the viral genome. In some embodiments one, two, three, four, five, six, seven, eight, nine, ten, fifteen, or twenty copies are used. In some embodiments one or more copies of the inhibitory sequence are on the plus strand and some on the minus strand of the virus genome.

The inhibitory oligonucleotide sequences are introduced into host cells as part of the viral genome or virion, rather than as a separate agent. This renders the effect of the oligonucleotide sequences local rather than systemic. Moreover, the immune evasion is transient as it occurs during AAV or other virus entry, unlike immune suppression with drugs which can last for weeks. Additionally, it ensures that the beneficial antagonist activity is where it needs to be— with the virus or viral genome. If the virus or viral genome is not replicated in the host cell, then the effect of the oligonucleotide will be transient. If the virus or viral genome is replicated, the effect will be coextensive with the replication.

An inhibitory nucleic acid sequence may be inserted into a viral genome using any means of recombinant DNA engineering. This may involve in vitro or in vivo recombination. In vitro recombination may be accomplished using a DNA ligase or other nucleic acid joining enzyme, for example. In vivo recombination may be accomplished by co-transforming a host cell with separate donor molecules that share homology by which they will recombine using host cell machinery. Alternatively, a single donor molecule may recombine in vivo with a host cell sequence. Combinations of these approaches may also be used. Typically the insertion will involve a standard linkage of one deoxyribonucleotide to another (a phosphodiester bond). However, there may be circumstances in which non-standard linkages will be used between the inhibitory nucleic acid sequence and the rest of the viral genome. Optionally, the inhibitory nucleic acid sequence is located in an untranslated region of the viral genome.

The genome may optionally contain a therapeutic gene and/or a marker gene. Typically this gene will be a non-viral gene, or a gene that is not naturally present in the viral genome. The gene may be expressible in a mammalian host cell or animal. Expression may be under the control of a viral promoter or a promoter that is introduced with the gene. Expression may be inducible, repressible, condition-responsive, or constitutive, as examples. A therapeutic gene is one which encodes an RNA or protein product beneficial to the host. The benefit may be, for example, to improve health, protect against infection, or remedy a deficiency. The marker may enable one to track the location, the level of replication, the level of propagation, the level of transcription, or the level of translation of the virus or its products or components. Suitable markers include those which are readily detectable, such as fluorescent proteins, chromogenic proteins, etc. Optionally, a second agent may be used or added for detection of the marker protein or for development of a detectable substance. Introduced genes may be human or non-human, heterologous (from another species) or homologous (from same species) or endogenous (from the same subject).

Any DNA viral genome can be used, whether single stranded or double stranded. Examples of suitable viruses which may be used, include without limitation, wild-type or variants of adeno-associated virus (AAV), adenovirus, herpes simplex virus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, human parvovirus B19, and enterovirus. The virus may be, without limitation, cytotoxic, cytolytic, or cause latent infections. Viral vectors in which viral genomes have been modified may also be used. As an example, a genome that is modified to encode fewer viral proteins may be used. As a further example, a viral genome that is modified to encode no viral proteins may be used. Viral genomes may include, by way of non-limiting example, inverted terminal repeats and/or other non-coding genetic elements that facilitate packaging of engineered viral genomes into the capsid.

Viral genomes may be delivered to a mammalian host cell as naked DNA, in a liposome, complexed to a polymer, in a condensed or compacted state, in a gold particle, in a virion, or any other means that is suitable for the application. Typically a complete viral genome will be administered, but in some situations, it may be desirable to use a partial genome. The partial genome may be complemented by helper functions provided by the host cell or another genomic or viral entity. Partial genomes may be used, for example, if the therapeutic payload is large and some essential viral functions must be omitted to package.

Recombinant viruses may be administered to a mammal or mammalian cells according to any route which is effective for the purpose. The administration may be systemic, e.g., via the blood. It may be delivered orally, subcutaneously, topically, bucally, anally, intramuscularly, intravenously, intratumorally, intracranially, intrathecally, subretinally, etc. Any suitable carrier or vehicle may also be used for administration. It may be desirable to pre-treat the cells or mammal to render them more permeable to or receptive to the recombinant virus. A mammal "in need of" a recombinant virus may be one for whom the virus will be beneficial. It may be a mammal with a disease or deficiency. It may be one for whom a diagnosis or analysis will be made. It may be one who can benefit from the administered recombinant virus, even though it does not have a disease or deficiency.

Taken together, our results show that incorporation of c41 or human telomeric sequences into the AAV genome (a) does not lower viral packaging and infectivity, (b) prevents TLR9-mediated inflammation, (c) reduces induction of pro-inflammatory cytokines, and (d) increases transgene expression. The increased transgene expression may be due to a reduced immune response, as TLR9 activation also induces interferon expression, which triggers an antiviral state. The engineered immune-evasion property we show below is specific (against TLR9), transient (e.g., may occur during viral entry), and does not result in systemic immune suppression (only targets AAV-infected immune cells).

The inhibitory nucleic acid sequences we used, as well as others known in the art, may be incorporated into other viruses that, like AAV, have potential utility for humans and other mammals but elicit inflammatory/immune responses that may be undesirable. For example, oncolytic viruses that preferentially infect and lyse cancer cells are used to kill or shrink tumors. These viruses are replicative (unlike AAV vectors used for gene therapy) so they can release new virions to shrink the remaining tumor. Examples include wild-type or variants of herpes simplex virus, adenovirus, and enterovirus. Some reports have shown that immunosuppression by chemotherapy can enhance oncolytic virus therapy, as the immune system normally attempts to inactivate the oncolytic virus, which would prevent it from infecting cancer cells. Therefore, it is possible that incorporating inhibitory oligonucleotides in the genomes of oncolytic viruses like herpes simplex virus may allow it to evade immune clearance and persist longer for oncolysis.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention. The disclosure of the invention includes all embodiments explicitly recited in the claims. Additionally, all features disclosed in the dependent claims apply equally to the independent claim from which they are based as to the other independent claims. Thus such combinations of dependent claims with other independent claims are expressly contemplated and disclosed.

Example 1—Construction of Modified Viral Genome

Figure 3:
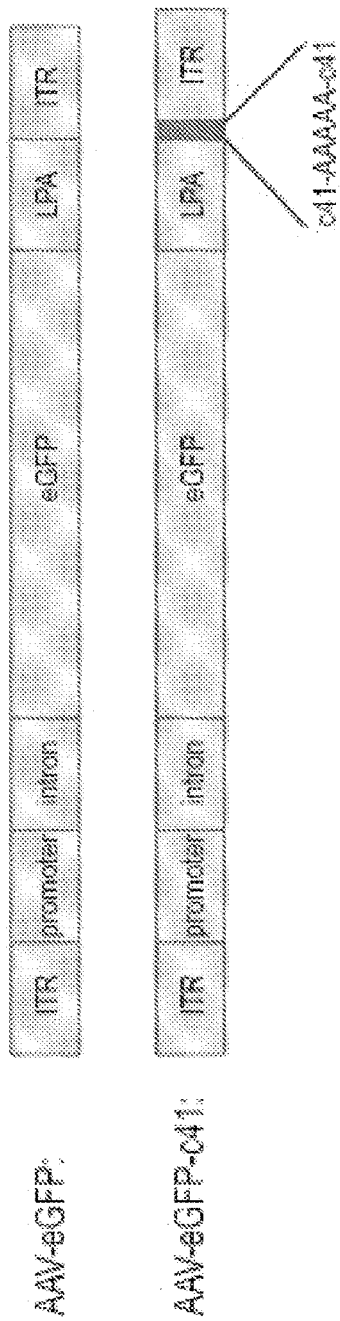
FIGS. 3A-3B.

To engineer an AAV vector that has the ability to specifically evade TLR9 activation in immune cells, we inserted two copies of c41 separated by a 5-nucleotide-long spacer (AAAAA; SEQ ID NO: 8) into the 3' untranslated region of AAV vector encoding enhanced green fluorescent protein (eGFP) (FIG. 3B). Subsequently, we produced wild-type AAV-eGFP virus and AAV-eGFP-c41 virus (harboring two c41 insertions). Infectious titers of both viruses were comparable ($\sim 10^9$ infectious units/ml, as determined by titering on HeLa cells), suggesting that addition of c41 into the viral genome did not hamper viral packaging and infectivity, an important consideration for viral vectors that have to be mass-produced for gene therapy.

Example 2—Modified Viral Genome Reduces NF-kB Activation

Figure 4:
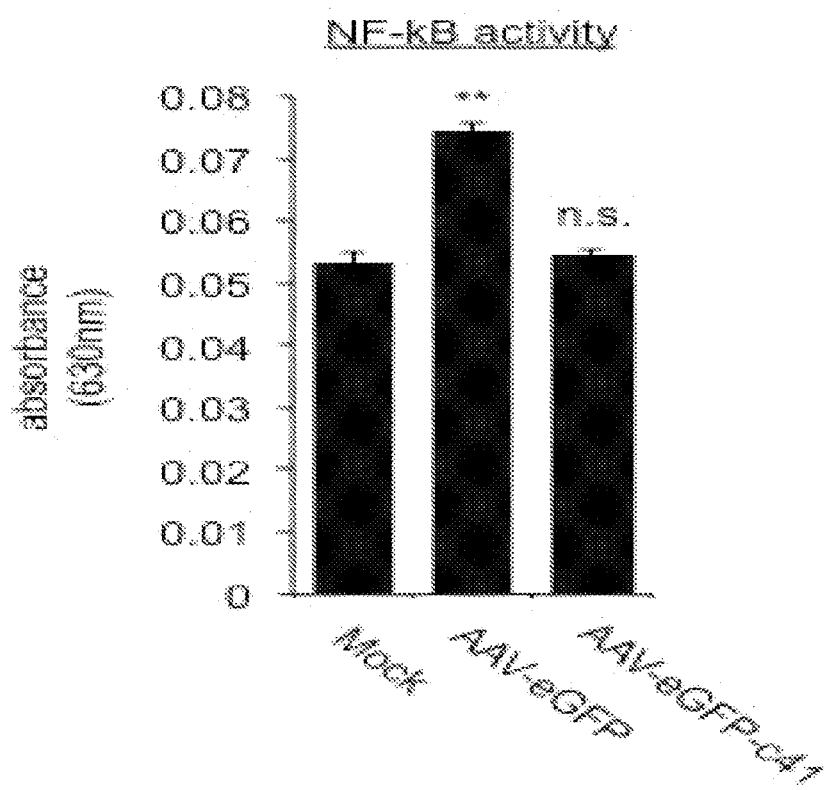
FIG. 4 shows NF-kB activity in HEK293 TLR9 cells mock-infected or infected with AAV virus (DJ capsid, self-complementary AAV genome, encoding eGFP). **, $p<0.005$; n.s., not significant. This experiment used a crude viral preparation.

To measure the inflammatory response, we used HEK293 cells stably expressing TLR9 (HEK293 TLR9 cells), which senses AAV DNA genomes, and also expressing alkaline phosphatase under the transcriptional control of NF-kB. When NF-kB is activated, which indicates inflammation, alkaline phosphatase is secreted into the media and acts on a provided substrate, leading to a change in color of the media that can be measured on a plate reader. We mock-infected HEK293 TLR9 cells or infected them with either AAV-eGFP or AAV-eGFP-c41. In agreement with the literature, AAV-eGFP infection induced a small but statistically significant increase in NF-kB activity (FIG. 4). In contrast, AAV-eGFP-c41 infection was not significantly different compared to mock-infected cells, indicating that the virus was able to evade eliciting an inflammatory response.

Figure 5:
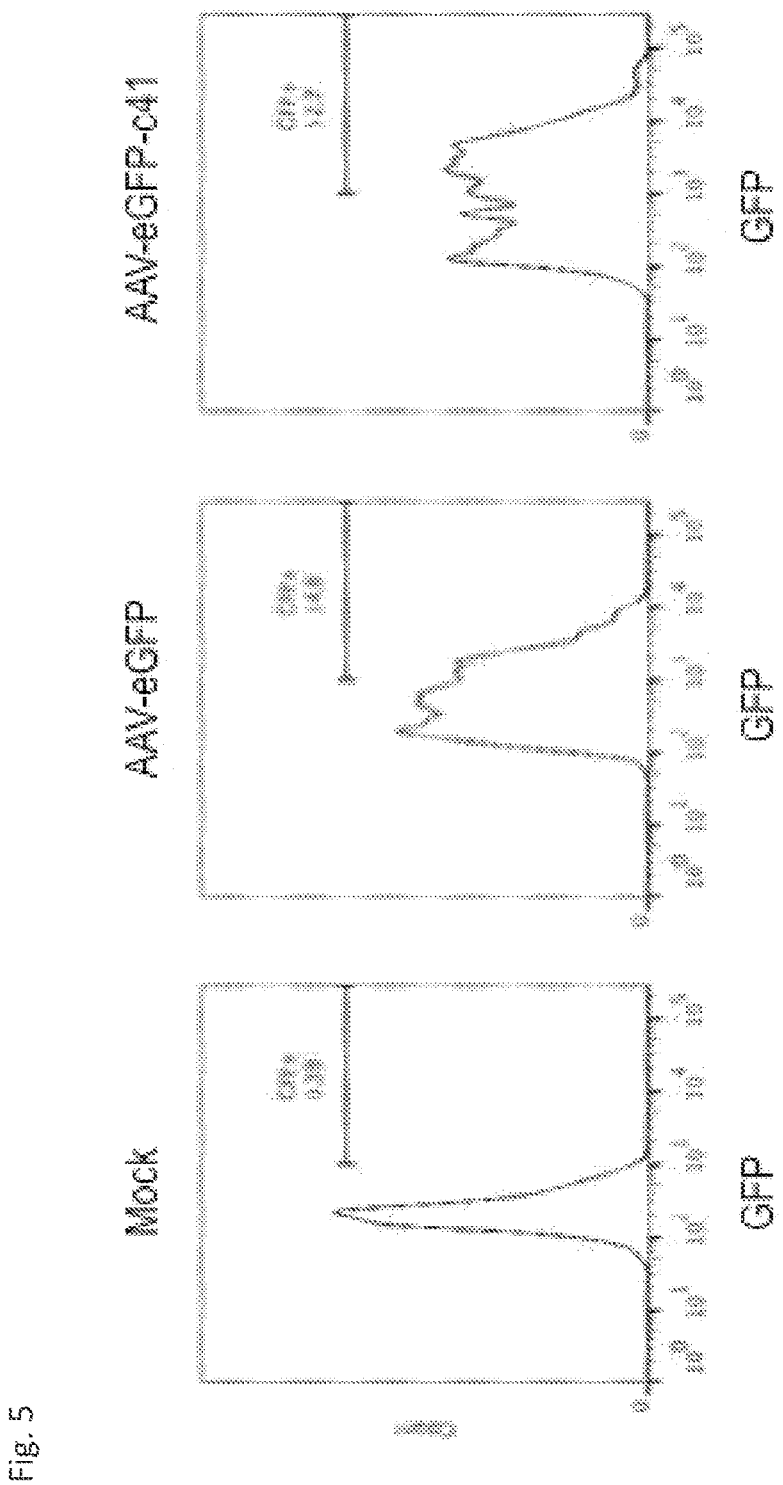
FIG. 5. Flow cytometry histograms showing GFP expression in HEK293 TLR9 cells mock-infected or infected with AAV virus with or without c41. This experiment used a crude viral preparation.

Example 3—Modified Viral Genome Transduced More Cells and Expresses More Transgene We analyzed the above three conditions (described in FIG. 4) for eGFP expression using flow cytometry. We found that AAV-eGFP-c41 transduced more cells than AAV-eGFP (52.7% GFP+ compared to 34.6% GFP+) (FIG. 5). In addition, GFP+ cells from AAV-eGFP-c41 infection expressed twice as much eGFP as GFP+ cells from AAV-eGFP infection (mean fluorescence intensity [MFI] of 5335 compared to 2749).

In summary, we engineered an AAV vector to evade TLR9-mediated inflammation by incorporating an inhibitory oligonucleotide in the viral genome.

Figures 6A, 6B:
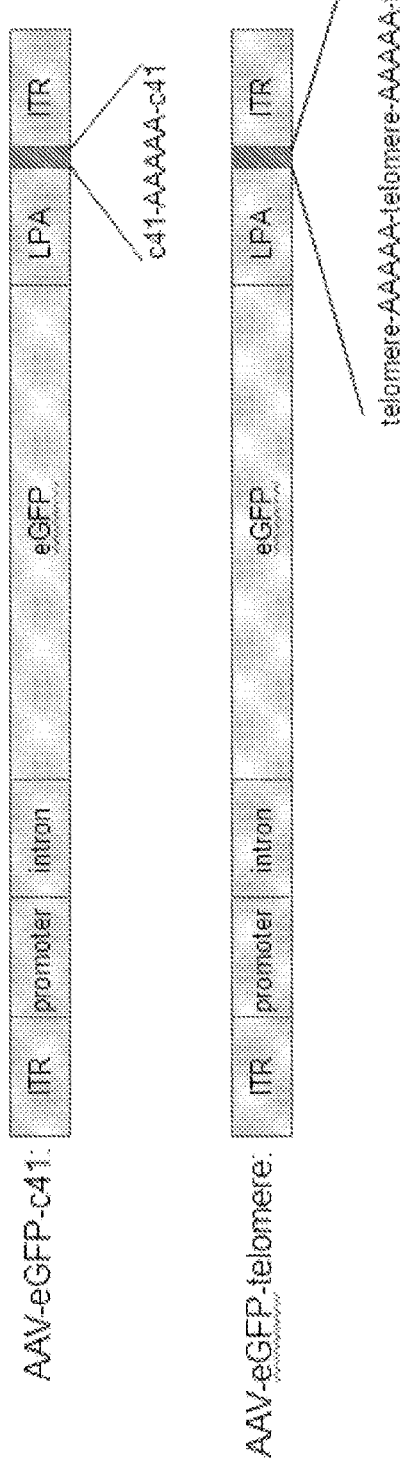
FIGS. 6A-6B.

Example 4—Incorporation of c41 or Telomeric Sequences in AAV Genome Transduced More Cells and Reduced TNF Induction We inserted three copies of "telomere," a sequence derived from mammalian telomeres that contains the suppressive $(TTAGGG)_4$ motif (SEQ ID NO: 6), which has been shown to block TLR9 signaling (FIG. 6A and FIG. 6B). AAV-eGFP-telomere virus yielded similar viral titers as AAV-eGFP and AAV-eGFP-c41 when titered on HeLa cells, demonstrating that incorporation of "telomere" does not hinder viral packaging and infectivity.

Figures 7A, 7B:
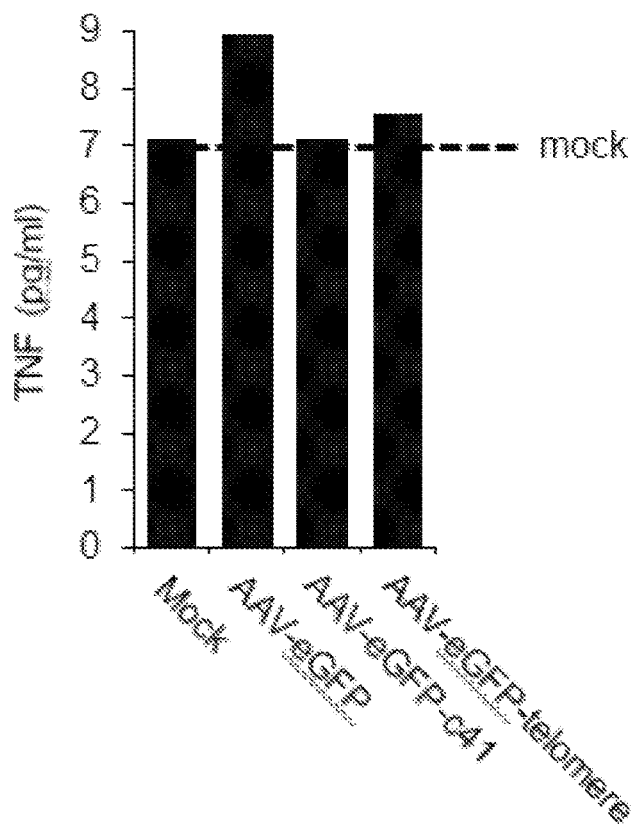
FIGS. 7A-7B.

When we infected a B cell line with similar amounts of AAV-eGFP or AAV-eGFP-c41 or AAV-eGFP-telomere virus, both AAV-eGFP-c41 and AAV-eGFP-telomere viruses transduced more cells than AAV-eGFP (FIG. 7A). This finding suggests too that incorporation of inhibitory sequences in the genome of AAV increases transgene expression.

Subsequently, we harvested primary human CD14+ monocytes from blood and subjected them to similar infection conditions as above. We performed ELISA on the supernatant to analyze TNF production, as TNF is a prototypical pro-inflammatory cytokine induced by NF-kB activation. AAV-eGFP infection increased TNF production compared to mock-infection, while AAV-eGFP-c41 and AAV-eGFP-telomere infections showed no or little increase in TNF production (FIGS. 7A-7B), showing that the two viruses were able to evade eliciting inflammatory responses.

Example 5—Engineering a Self-Complementary AAV Vector

Investigators often use short inhibitory oligonucleotides (typically 10-30 nucleotides in length) to antagonize TLR9 signaling in cell culture. However, it is unknown if these inhibitory oligonucleotides retain functionality in the context of a much larger viral genome (i.e., the sequence is covalently linked on both ends to much longer sequences). To test this possibility, we utilized a self-complementary (sc) AAV vector encoding enhanced green fluorescent protein (eGFP), and inserted 3 copies of "c41" or "telomere", derived from bacteria and mammalian telomeres respectively [52, 57, 58, 61], into a plasmid harboring the vector genome (FIGS. 8A and 8B). We started with sc AAV vectors as they have been shown to be more efficient at triggering TLR9 activation and inducing more inflammation in the mouse liver than single-stranded (ss) AAV vectors. As "c41" and "telomere" are predicted to have strong secondary structure, we used an AAAAA linker between copies of the inhibitory oligonucleotide. In addition, 3xc41 and 3x telomere sequences were placed after the polyA sequence and upstream of the right inverted terminal repeat (ITR) so they would be present in the DNA genome during viral entry, but would be absent from subsequent mRNA transcripts upon successful transduction ("scAAV-eGFP-3xc41" and "scAAV-eGFP-3x telomere"). Finally, to determine if the location of inhibitory oligonucleotide in the viral genome matters, we also created a vector where 3x telomere was located between the left ITR and the promoter ("scAAV-3x telomere-eGFP").

Example 6—Inflammatory Responses in Primary Human Macrophages and Monocytes In Vitro We packaged the various AAV vectors into AAV2 serotype and infected primary human monocyte-derived macrophages at a multiplicity of infection (MOI) of $10^5$ viral genomes (vg) per cell. As expected, we found that scAAV-eGFP infection of macrophages elicited robust induction of TNF in the supernatant, a prototypical inflammatory cytokine with well-described roles in stimulating fever, apoptosis and inflammation, and is produced upon TLR9 signaling and NF-kB activation (FIG. 9A). In contrast, both scAAV-eGFP-3x41 and scAAV-eGFP-3x telomere markedly decreased TNF induction by >95%, indicating that incorporation of "c41" or "telomere" in these viruses could evade eliciting inflammatory responses compared to the wild-type (WT) vector. Furthermore, scAAV-3x telomere-eGFP was also able to prevent TNF induction by >95%, demonstrating that the inserted inhibitory oligonucleotides can be placed in other parts of the viral genome and retain the ability to block inflammation. Mock infection with phosphate-buffered saline (PBS) and treatment with ODN 2006, a commercially available CpG-containing oligonucleotide that is known to strongly activate TLR9/NF-kB and inflammation, served as negative and positive controls respectively. We tested primary human CD14+ monocytes and found that again, scAAV-eGFP triggered robust TNF induction while scAAV-eGFP-3xc41 and scAAV-eGFP-3x telomere negated most of the TNF induction (FIG. 9B). scAAV-3x telomere-eGFP likewise reduced TNF induction, although inhibition was 85%, which may be due to differences between cell types or donor tissue. The evasion of TNF induction was also reproduced in primary CD14+ monocytes obtained from another donor (FIG. 9C).

As further characterization, we inserted 3 copies of "control," a random sequence that does not block TLR9, or 1 copy of "telomere", into a plasmid harboring the vector genome (FIG. 10A, FIG. 10B). We picked the sequence "control" as it has been used as a negative control oligonucleotide in TLR9 experiments. We found that scAAV-eGFP-1x telomere was able to reduce TNF induction compared to scAAV-eGFP in human macrophages, but not as efficiently as scAAV-eGFP-3x telomere (FIG. 10C). This indicates that 1 copy of telomere can reduce inflammation. We also observed that scAAV-eGFP-3xcontrol elicited TNF secretion as efficiently as scAAV-eGFP in human monocytes, suggesting that insertion of sequences that inhibit TLR9 are required to block inflammation (FIG. 10D).

Figures 11A, 11B:
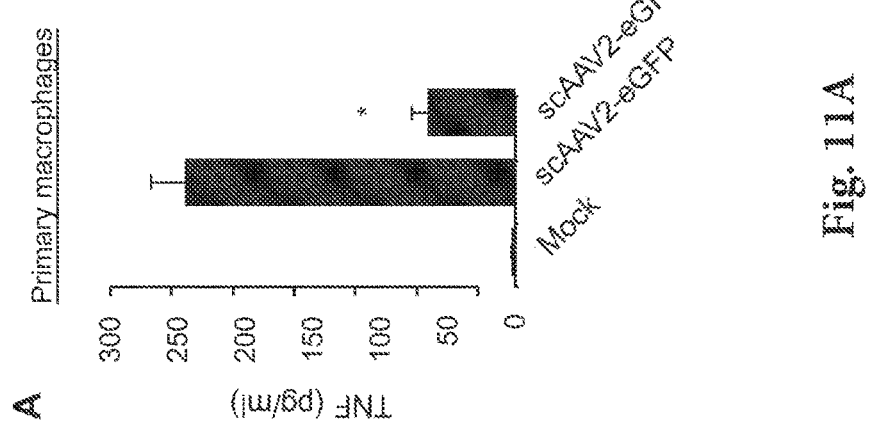
FIG. 11A-11B.

As AAV vectors are considered biologics and may exhibit lot-to-lot variability, we produced another batch of both scAAV-eGFP and scAAV-eGFP-3x telomere AAV2 viruses, and found that scAAV-eGFP-3x telomere was able to reduce ~75% of TNF induction compared to the WT vector (FIG. 11A). Based on the multiple viral preps and donor monocytes and macrophages (FIGS. 9A-9C, FIGS. 10A-10E and FIGS. 11A-11B), we conclude that our engineered vectors containing 3 copies of "c41" or "telomere" reduce TNF induction by approximately 75-98% compared to the WT vector. On average, scAAV-eGFP-3x telomere reduced ~85% of TNF induction compared to scAAV-eGFP. Importantly, we did not observe differences in viral titers (assayed by qPCR for viral genomes) obtained from producing any of the above AAV2 vectors, suggesting that the engineered vectors are not defective in packaging (data not shown). Furthermore, when we infected HeLa cells, a permissive cell line widely used to titer AAV infectivity, with a range of MOIs of scAAV-eGFP and scAAV-eGFP-3x telomere, we did not observe differences in transduction (% GFP+ cells) over 4 logs of viral titers, demonstrating that the engineered vector is equally competent at transducing cells (FIG. 11B).

Example 7—Inflammatory Responses in Liver Tissues of Mice In Vivo

Intravenous delivery of AAV is often used to transduce hepatocytes for gene therapy. Previous work has shown that upon intravenous administration of AAV, Kupffer cells (resident hepatic antigen-presenting cells) in the liver of mice are capable of sensing sc AAV genomes and triggering inflammatory and innate immune responses 1-9 h later [36]. These responses include induction of proinflammatory cytokines such as TNF and IL6 and type I interferons such as IFN-β. TLR9−/− mice do not exhibit these inflammatory and innate immune responses in the liver, demonstrating a central role for TLR9 in vivo as an innate immune sensor. In addition, immune cells such as neutrophils, macrophages and natural killer (NK) cells infiltrate the liver 2 h after AAV administration. To determine if our engineered vectors can reduce inflammation in the liver in vivo, we administered PBS or equal amounts of scAAV-eGFP or scAAV-eGFP-3x telomere via tail vein injection. We selected scAAV-eGFP-3x telomere for in vivo characterization as "telomere" is derived from human sequences and might be preferable for clinical use. In agreement with previous work, scAAV-eGFP stimulated increased Tnf and Il6 expression in the liver (approximately 3 to 10 fold, compared to saline), indicating inflammation (FIG. 12A). In contrast, scAAV-eGFP-3x telomere showed little to no increase in inflammatory markers. We tested more mice in subsequent experiments and found that scAAV-eGFP stimulated statistically significant Tnf induction in the liver compared to saline, while scAAV-eGFP-3x telomere and scAAV-eGFP-3xc41 did not (FIGS. 12B and 12C), demonstrating their ability to evade eliciting inflammation in the liver. Finally, we confirmed that scAAV-eGFP-3xcontrol is not able to prevent inflammation in the liver compared to scAAV-eGFP (FIG. 10E).

Figure 13:
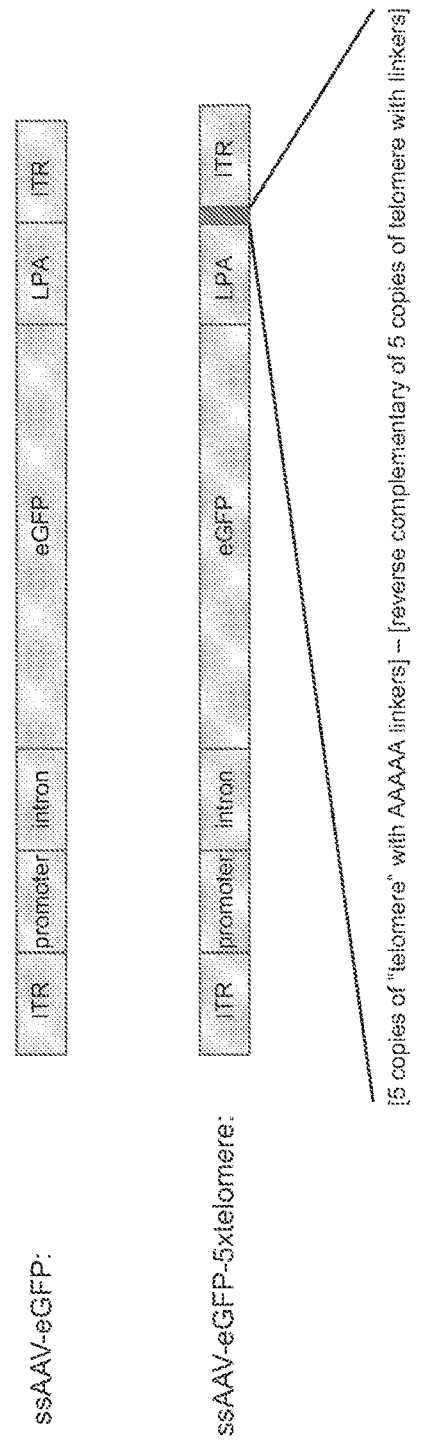
FIG. 13. Genome organization of a single-stranded AAV vector (ssAAV-eGFP) and ssAAV-eGFP-5x telomere.

Example 8—Engineering a Single-Stranded AAV Vector and Determining Inflammatory Responses in Eye Tissues of Mice In Vivo Next, we engineered a single-stranded AAV vector, ssAAV-eGFP, by inserting 5 copies of "telomere" with AAAAA linkers, followed by another 5 copies but in antisense orientation, into the plasmid, giving ssAAV-eGFP-5x telomere (FIG. 13). Since both positive and negative strands of the viral genome are equally likely to be packaged into a viral particle, this ensures that each packaged viral genome would have 5 copies of "telomere" in the correct orientation. Two AAV8 viruses were produced and purified. Again, we did not observe differences in titers between the two vectors, suggesting similar packaging efficiency (data not shown). ssAAV-eGFP was selected as it has been previously used for subretinal injections in mice and efficiently transduces photoreceptors in the eye [62].

Several studies have suggested that AAV gene therapy in the eye and brain appears to be generally safe [63]. While the eye is often assumed to be an immune-privileged site, it is known to harbor microglia, resident macrophages of the central nervous system which have been reported to express TLR9 and respond to CpG motifs [64-67]. A recent study delivering AAV vectors by subretinal injection in cynomolgus macaques reported dose-related anterior and posterior segment inflammation in the animals, and a macaque was euthanized prematurely due to severe ocular inflammation [68]. Furthermore, vitreous aspirate from the euthanized animal demonstrated the presence of neutrophils and macrophages. Another study utilizing canine models similarly observed anterior and posterior uveitis upon subretinal injection of AAV vectors, and 3 of 17 eyes developed a multifocal chorioretinitis, which was likewise associated with higher vector doses [69]. These findings strongly suggest that AAV vectors are subject to innate immune surveillance in the eye and can trigger deleterious inflammatory and immune responses.

Saline or similar amounts of ssAAV-eGFP or ss-AAV-eGFP-5x telomere were delivered via subretinal injection into neonates eyes and measured the expression of inflammatory and immune genes. The three mice that received saline injections were uniformly low for Tnf expression in the retina and were set to 1 fold expression (FIG. 14A). In contrast, of the five mice that received ssAAV-eGFP, two exhibited mild upregulation of Tnf (1.9 fold and 8.3 fold), while three animals demonstrated large induction of Tnf (62.2 fold, 534 fold, and 1003 fold), with a mean of 321 fold for the five animals. This finding indicates that while there is variability in inflammation, some animals mount a very strong inflammatory response in the retina upon ssAAV-eGFP subretinal injection. The variability may be due to differences in each injection procedure or the immune status of each animal. Strikingly, the five animals receiving ssAAV-eGFP-5x telomere had a mean Tnf induction of 5.6 fold with much less variability, suggesting that ssAAV-eGFP-5x telomere was able to avoid eliciting strong inflammation. Similar results were observed in the rest of the eyecup but at a lower magnitude, indicating inflammation was not restricted to the retina (FIG. 14B). We also measured Ifng expression in the retina, a type II interferon critical for antiviral immune responses [70], and observed a similar pattern (FIG. 14C). Prior studies have suggested that subretinal injection of AAV may trigger immune cell infiltration in the eye. Therefore, we also analyzed expression of genes that are known to be expressed specifically in different types of immune cells. We found 18.2 fold higher expression of Aif1 (encoding Iba1, a specific marker for microglia [71, 72]) in ssAAV-eGFP injections compared to saline, suggesting microglia proliferation and/or activation in the retina (FIG. 15A). In contrast, ssAAV-eGFP-5x telomere only showed 1.9 fold induction of Aif1 expression. In addition, we found 45.8 fold and 41.8 fold induction of Cd4 and Cd8a, markers of CD4+ helper T cells and CD8+ cytolytic T cells respectively, by ssAAV-eGFP, while ssAAV-eGFP-5x telomere only showed 1.5 fold and 3.4 fold induction (FIGS. 15B and 15C). Again, there was considerable variability among mice treated with ssAAV-eGFP with a subset of animals showing robust induction. These results demonstrate that subretinal injection of ssAAV-eGFP administration can stimulate T cells infiltration in the retina, while ssAAV-eGFP-5x telomere strongly diminishes it. Taken together, our data indicate that while ssAAV-eGFP induces robust inflammatory and immune responses in the retina and the surrounding tissue, and significant variability is observed, ssAAV-eGFP-5x telomere is capable of mitigating a large portion of these responses.

Figure 16:
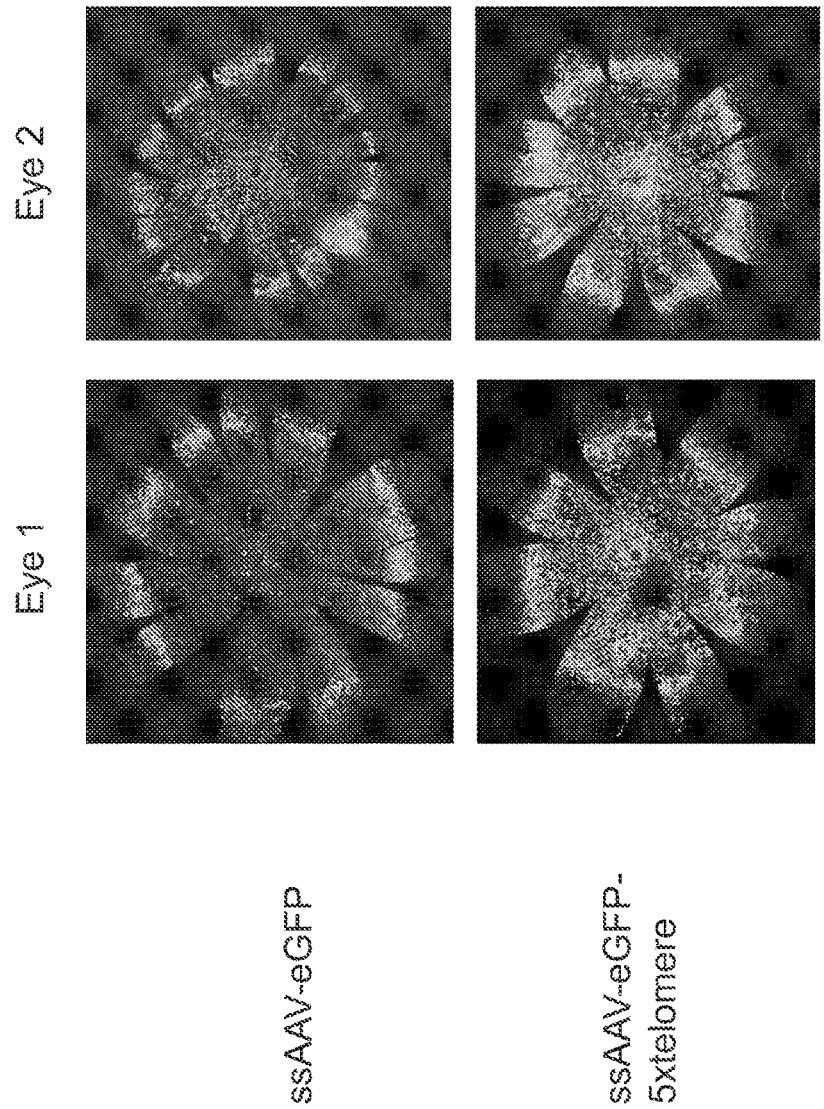
FIG. 16. GFP expression in the eye. Neonatal CD1 mice (P1) received indicated AAV8 viruses ($1.8 \times 10^8$ vg per mouse eye) by subretinal injections. At P30, the animals were euthanized and GFP expression was visualized in flat-mounted eye cups. Data shown are n=2 mice per condition.

Given the marked differences in inflammation both in vitro and in vivo, we sought to determine if there are any differences in long-term gene expression. We examined flat-mounted eye cups at P30, 29 d after subretinal injection of the mice, and found that more cells were GFP+ and GFP expression was stronger in ssAAV-eGFP-5x telomere treated eyes compared to ssAAV-eGFP, suggesting enhanced gene expression (FIG. 16). Thus, the engineered vector is able to reduce inflammatory and immune responses in the retina and also augment transgene expression.

Example 9—Material and Methods

Animals

C57BL/6 mice (male, 7-9 weeks old) were purchased from the Jackson Laboratory and CD1 mice were purchased from Charles River Laboratories.

AAV Vectors

Self-complementary (sc) or single-stranded (ss) AAV vectors were used in this study. Self-complementary vectors lack the terminal resolution sequence in one ITR. All vector genomes were flanked by AAV2 ITRs. scAAV-eGFP was purchased from Cell Biolabs (VPK-430) and has been previously described [73]. scAAV-eGFP expressed enhanced green fluorescent protein (eGFP) from the cytomegalovirus (CMV) promoter, and included an SV40 intron and SV40 polyA sequence. ssAAV-eGFP has been previously described [62] and was originally obtained from the Harvard DF/HCC DNA Resource Core (clone ID: EvN000061595). ssAAV-eGFP contained a CMV enhancer/promoter, human β-globin intron, eGFP, and β-globin polyA sequence. The sequences of "c41" (5'-TGGCGCGCACC-CACGGCCTG-3; SEQ ID NO: 1) derived from *Pseudomonas aeruginosa* and "telomere" (5'-TTTAGGGTTAGGGT-TAGGGTTAGGG-3'; SEQ ID NO: 9; initial T nucleotide is optional for function) derived from mammalian telomeres have been described [52, 57, 58, 61]. A widely used "telomere" oligonucleotide (manufactured by Invivogen, catalog code "tlrl-nag") harbored an additional T (in bold) compared to published studies and thus was included in the sequence. During the course of this study, Invivogen removed the additional T in their manufactured "telomere" oligonucleotide (catalog code "tlrl-ttag151"). In addition, "control" (5'-GCTAGATGTTAGCGT-3'; SEQ ID NO: 34) was used as a negative control sequence that does not inhibit TLR9 activation (Invivogen, catalog code "tlrl-2088c").

To engineer scAAV-eGFP, sequences were inserted into the unique SpeI site found immediately 5' of the right ITR. To facilitate sub-cloning, a unique ClaI site was created immediately 5' of the inserted sequences, thus allowing ClaI/SpeI sub-cloning of sequences. 3 copies of "c41," "telomere," or "control" were inserted, separated by AAAAA linkers, giving scAAV-eGFP-3xc41, scAAV-eGFP-3x telomere and scAAV-eGFP-3x control, respectively. Alternatively, one copy of "telomere" was inserted, with an AAAAA linker (SEQ ID NO: 8), giving scAAV-eGFP-1x telomere. We also inserted 3x telomere between the left ITR and CMV promoter using the unique AvrII site, giving scAAV-3x telomere-eGFP.

To engineer ssAAV-eGFP, KpnI-5x telomere(sense)-5x telomere(anti-sense)-NheI was inserted immediately 5' of the XbaI site adjacent to the right ITR. Again, AAAAA was used as a linker between copies of "telomere". Both sense and anti-sense sequences of "telomere" were added as single-stranded AAV vectors have an equal chance of packaging positive or negative strands of the viral genome, thus ensuring that all packaged AAV genomes will carry 5 copies of "telomere" in the right orientation.

Self-complementary vectors were packaged into AAV2 (Vigene Biosciences) by triple transfection of HEK293 cells and purified using iodixanol gradient ultracentrifugation and then concentrated to 500 µl using Amicon Ultra-15 columns in PBS. The purified viruses were titered by qPCR using primers derived from ITR and an AAV standard. The final yield of the viruses ranged from $0.5$-$3 \times 10^{13}$ vg.

Single-stranded vectors were packaged into AAV8 based on previously described protocols [74, 75]. Briefly, AAV vector, rep2-cap8 packaging plasmid and adenoviral helper plasmid were transfected into HEK293T cells with polyethylenimine and supernatant was collected 72 h after transfection. AAV8 viruses were precipitated with 8.5% w/v PEG8000 and 0.4M NaCl and centrifuged at 7000 g. The pellet was resuspended in lysis buffer (150 mM NaCl and 20 mM Tris, pH 8.0) and MgCl2 was added to a final concentration of 1 mM. The resuspended viruses were incubated with 25 U/ml Benzonase (Sigma) at 37° C. for 15 min and run on an iodixanol gradient. Recovered AAV vectors were washed 3 times with PBS using Amicon 100K columns (EMD Millipore) and concentrated to 100-500 µl of PBS. Protein gels were run to determine virus titers, using serial dilutions of previous AAV standards for comparison.

Primary Human Monocytes and Monocyte-Derived Macrophages for In Vitro Studies

Human peripheral blood mononuclear cells (PBMCs) from unidentified healthy donors were purchased (ZenBio). This study was done in accordance with the ethical guidelines of Harvard Medical School. CD14+ monocytes were positively selected from PBMCs using anti-CD14 magnetic microbeads according to the manufacturer's instructions (Miltenyi Biotec) or purchased from Stemcell Technologies. To obtain monocyte-derived macrophages, monocytes were cultured with 50 ng/ml of recombinant human macrophage colony stimulation factor (rhM-CSF, purchased from Peprotech) for 5 to 6 d to allow differentiation into macrophages. Monocytes and macrophages were either used fresh or cryopreserved for subsequent studies.

$1 \times 10^5$ monocytes or macrophages were seeded in 190 µl of RPMI growth media per well in 96 well round bottom plates or 96 well flat bottom plates respectively, and infected with 10 ul AAV2 viruses at indicated MOIs in PBS. Mock infection (addition of 10 ul PBS) and ODN 2006 (final concentration of 5 uM, Invivogen), a CpG-containing oligonucleotide known to activate TLR9 and trigger inflammation, served as negative and positive controls. 18 h after infection, supernatants were collected and clarified by low speed centrifugation, followed by ELISA for human TNF (Thermo Scientific).

HeLa Cells Infection

HeLa cells are highly permissive for AAV2 vectors and are commonly used to determine the transducing titer of AAV2 vector preparations [76]. Briefly, HeLa cells were seeded overnight in 12 wells and were approximately 80% confluent at time of infection ($3 \times 10^5$ cells). Cells were infected with serial ten-fold dilutions of viruses at indicated MOIs and incubated for 48 h before fixing with 1% paraformaldehyde in PBS and followed by flow cytometry analysis for GFP+ cells. PBS mock-infected cells were used to determine GFP+ signal.

Liver Studies In Vivo

Adult C57BL/6 mice were injected intravenously with 100 µl PBS or AAV2 viruses ($10^{11}$ vg per animal) by tail vein injection as previously described [36]. 2 h later, the animals were sacrificed and a portion of the right median lobe of the liver was saved in RNAlater solution (Thermo Scientific). Total RNA was extracted from 10-30 mg of mechanically disrupted liver sample by using an RNA extraction kit (OMEGA Bio-Tek). Similar amounts of RNA were reverse transcribed into cDNA with a high-capacity RNA-to-cDNA kit (Thermo Scientific) and similar amounts of cDNA were assayed with quantitative PCR (qPCR) using TaqMan Fast Advanced Master Mix (Thermo Scientific) and commercially available pre-designed primers/probes with FAM reporter dye for the indicated target genes (IDT). Expression level for each gene was calculated by normalizing against the housekeeping genes Actb or Gapdh using the $\Delta\Delta$CT method and expressed as fold levels compared to saline-injected mice. All qPCR reactions were run on a realplex$^4$ Mastercycle (Eppendorf).

Eye Studies In Vivo

Subretinal injection into postnatal day 1 (P1) CD1 neonate eyes were performed as previously described [74, 75]. Approximately 0.2 ul AAV8 virus ($1.8 \times 10^8$ vg per eye) was introduced into the subretinal space using a pulled angled glass pipette controlled by a FemtoJet (Eppendorf). At P21, animals were sacrificed and the eyecup was dissected out. The retina and the rest of the eyecup were subjected to RNA extraction, reverse transcription, and qPCR as described in the liver studies. To visualize GFP expression by histology, eyes were excised at P30, fixed in 4% paraformaldehyde for 2 h, and washed in PBS 3 times. Eye cups were dissected out by removing the cornea, lens, iris, vitreous body and peripheral muscles. Images of flat-mounted eye cups were taken using a ×10 objective on a Keyence BZ-x700 microscope. Images used for comparison between groups were taken at the same imaging settings in the same imaging session.

Statistics

Unpaired two-tailed Student's t-tests were used to compare differences between two unpaired experimental groups in all cases. A P value of <0.05 was considered statistically significant. No pre-specified effect size was assumed and in general three to five replicates for each condition was used.

REFERENCES

1. Naldini L. Gene therapy returns to centre stage. Nature. 2015; 526(7573):351-60. doi: 10.1038/nature15818. PubMed PMID: 26469046.
2. Yla-Herttuala S. Endgame: glybera finally recommended for approval as the first gene therapy drug in the European union. Mol Ther. 2012; 20(10):1831-2. doi: 10.1038/mt.2012.194. PubMed PMID: 23023051; PubMed Central PMCID: PMCPMC3464639.
3. Gaudet D, Methot J, Kastelein J. Gene therapy for lipoprotein lipase deficiency. Curr Opin Lipidol. 2012; 23(4):310-20. doi: 10.1097/MOL.0b013e3283555a7e. PubMed PMID: 22691709.
4. Samulski R I, Muzyczka N. AAV-Mediated Gene Therapy for Research and Therapeutic Purposes. Annu Rev Virol. 2014; 1(1):427-51. doi: 10.1146/annurev-virology-031413-085355. PubMed PMID: 26958729.
5. Mingozzi F, High K A. Therapeutic in vivo gene transfer for genetic disease using AAV: progress and challenges. Nat Rev Genet. 2011; 12(5):341-55. doi: 10.1038/nrg2988. PubMed PMID: 21499295.
6. Kotterman M A, Schaffer D V. Engineering adeno-associated viruses for clinical gene therapy. Nat Rev Genet. 2014; 15(7):445-51. doi: 10.1038/nrg3742. PubMed PMID: 24840552; PubMed Central PMCID: PMCPMC4393649.
7. McLaughlin S K, Collis P, Hermonat P L, Muzyczka N. Adeno-associated virus general transduction vectors: analysis of proviral structures. J Virol. 1988; 62(6):1963-73. PubMed PMID: 2835501; PubMed Central PMCID: PMCPMC253280.
8. Hauswirth W W, Berns K I. Origin and termination of adeno-associated virus DNA replication. Virology. 1977; 78(2):488-99. PubMed PMID: 867815.
9. Zhong L, Zhou X, Li Y, Qing K, Xiao X, Samulski R J, et al. Single-polarity recombinant adeno-associated virus 2 vector-mediated transgene expression in vitro and in vivo: mechanism of transduction. Mol Ther. 2008; 16(2):290-5. doi: 10.1038/sj.mt.6300376. PubMed PMID: 18087261.
10. Zhou X, Zeng X, Fan Z, Li C, McCown T, Samulski R J, et al. Adeno-associated virus of a single-polarity DNA genome is capable of transduction in vivo. Mol Ther. 2008; 16(3):494-9. doi: 10.1038/sj.mt.6300397. PubMed PMID: 18180769.
11. Samulski R J, Chang L S, Shenk T. A recombinant plasmid from which an infectious adeno-associated virus genome can be excised in vitro and its use to study viral replication. J Virol. 1987; 61(10):3096-101. PubMed PMID: 3041032; PubMed Central PMCID: PMCPMC255885.
12. McCarty D M. Self-complementary AAV vectors; advances and applications. Mol Ther. 2008; 16(10):1648-56. doi: 10.1038/mt.2008.171. PubMed PMID: 18682697.
13. McCarty D M, Monahan P E, Samulski R J. Self-complementary recombinant adeno-associated virus (scAAV) vectors promote efficient transduction independently of DNA synthesis. Gene Ther. 2001; 8(16):1248-54. doi: 10.1038/sj.gt.3301514. PubMed PMID: 11509958.
14. Calcedo R, Morizono H, Wang L, McCarter R, He J, Jones D, et al. Adeno-associated virus antibody profiles in newborns, children, and adolescents. Clin Vaccine Immunol. 2011; 18(9):1586-8. doi: 10.1128/CVI.05107-11. PubMed PMID: 21775517; PubMed Central PMCID: PMCPMC3165215.
15. Calcedo R, Vandenberghe L H, Gao G, Lin J, Wilson J M. Worldwide epidemiology of neutralizing antibodies to adeno-associated viruses. J Infect Dis. 2009; 199(3):381-90. doi: 10.1086/595830. PubMed PMID: 19133809.
16. Bainbridge J W, Smith A J, Barker S S, Robbie S, Henderson R, Balaggan K, et al. Effect of gene therapy on visual function in Leber's congenital amaurosis. N Engl J Med. 2008; 358(21):2231-9. doi: 10.1056/NEJMoa0802268. PubMed PMID: 18441371.
17. Maguire A M, High K A, Auricchio A, Wright J F, Pierce E A, Testa F, et al. Age-dependent effects of RPE65 gene therapy for Leber's congenital amaurosis: a phase 1 dose-escalation trial. Lancet. 2009; 374(9701):1597-605. doi: 10.1016/S0140-6736(09)61836-5. PubMed PMID: 19854499; PubMed Central PMCID: PMCPMC4492302.
18. Maguire A M, Simonelli F, Pierce E A, Pugh E N, Jr., Mingozzi F, Bennicelli J, et al. Safety and efficacy of gene transfer for Leber's congenital amaurosis. N Engl J Med. 2008; 358(21):2240-8. doi: 10.1056/NEJMoa0802315. PubMed PMID: 18441370; PubMed Central PMCID: PMCPMC2829748.
19. Jacobson S G, Cideciyan A V, Ratnakaram R, Heon E, Schwartz S B, Roman A J, et al. Gene therapy for leber congenital amaurosis caused by RPE65 mutations: safety and efficacy in 15 children and adults followed up to 3 years. Arch Ophthalmol. 2012; 130(1):9-24. doi: 10.1001/archophthalmol.2011.298. PubMed PMID: 21911650; PubMed Central PMCID: PMCPMC3600816.

20. Kaplitt M G, Feigin A, Tang C, Fitzsimons H L, Mattis P, Lawlor P A, et al. Safety and tolerability of gene therapy with an adeno-associated virus (AAV) borne GAD gene for Parkinson's disease: an open label, phase I trial. Lancet. 2007; 369(9579):2097-105. doi: 10.1016/S0140-6736(07)60982-9. PubMed PMID: 17586305.

21. Leone P, Shera D, McPhee S W, Francis J S, Kolodny E H, Bilaniuk L T, et al. Long-term follow-up after gene therapy for canavan disease. Sci Transl Med. 2012; 4(165):165ra3. doi: 10.1126/scitranslmed.3003454. PubMed PMID: 23253610; PubMed Central PMCID: PMCPMC3794457.

22. Manno C S, Pierce G F, Arruda V R, Glader B, Ragni M, Rasko J J, et al. Successful transduction of liver in hemophilia by AAV-Factor IX and limitations imposed by the host immune response. Nat Med. 2006; 12(3):342-7. doi: 10.1038/nm1358. PubMed PMID: 16474400.

23. Nathwani A C, Tuddenham E G, Rangarajan S, Rosales C, McIntosh J, Linch D C, et al. Adenovirus-associated virus vector-mediated gene transfer in hemophilia B. N Engl J Med. 2011; 365(25):2357-65. doi: 10.1056/NEJMoa1108046. PubMed PMID: 22149959; PubMed Central PMCID: PMCPMC3265081.

24. Carpentier A C, Frisch F, Labbe S M, Gagnon R, de Wal J, Greentree S, et al. Effect of alipogene tiparvovec (AAV1-LPL(S447X)) on postprandial chylomicron metabolism in lipoprotein lipase-deficient patients. J Clin Endocrinol Metab. 2012; 97(5):1635-44. doi: 10.1210/jc.2011-3002. PubMed PMID: 22438229.

25. Manno C S, Chew A J, Hutchison S, Larson P J, Herzog R W, Arruda V R, et al. AAV-mediated factor IX gene transfer to skeletal muscle in patients with severe hemophilia B. Blood. 2003; 101(8):2963-72. doi: 10.1182/blood-2002-10-3296. PubMed PMID: 12515715.

26. Jaski B E, Jessup M L, Mancini D M, Cappola T P, Pauly D F, Greenberg B, et al. Calcium upregulation by percutaneous administration of gene therapy in cardiac disease (CUPID Trial), a first-in-human phase 1/2 clinical trial. J Card Fail. 2009; 15(3):171-81. doi: 10.1016/j.cardfail.2009.01.013. PubMed PMID: 19327618; PubMed Central PMCID: PMCPMC2752875.

27. Ran F A, Cong L, Yan W X, Scott D A, Gootenberg J S, Kriz A J, et al. In vivo genome editing using *Staphylococcus aureus* Cas9. Nature. 2015; 520(7546):186-91. doi: 10.1038/nature14299. PubMed PMID: 25830891; PubMed Central PMCID: PMCPMC4393360.

28. Balazs A B, Chen J, Hong C M, Rao D S, Yang L, Baltimore D. Antibody-based protection against HIV infection by vectored immunoprophylaxis. Nature. 2011; 481(7379):81-4. doi: 10.1038/nature10660. PubMed PMID: 22139420; PubMed Central PMCID: PMCPMC3253190.

29. Gardner M R, Kattenhorn L M, Kondur H R, von Schaewen M, Dorfman T, Chiang J J, et al. AAV-expressed eCD4-Ig provides durable protection from multiple SHIV challenges. Nature. 2015; 519(7541):87-91. doi: 10.1038/nature14264. PubMed PMID: 25707797; PubMed Central PMCID: PMCPMC4352131.

30. Adam V S, Crosariol M, Kumar S, Ge M Q, Czack S E, Roy S, et al. Adeno-associated virus 9-mediated airway expression of antibody protects old and immunodeficient mice against influenza virus. Clin Vaccine Immunol. 2014; 21(11):1528-33. doi: 10.1128/CVI.00572-14. PubMed PMID: 25209558; PubMed Central PMCID: PMCPMC4248762.

31. Balazs A B, Bloom J D, Hong C M, Rao D S, Baltimore D. Broad protection against influenza infection by vectored immunoprophylaxis in mice. Nat Biotechnol. 2013; 31(7):647-52. doi: 10.1038/nbt.2618. PubMed PMID: 23728362; PubMed Central PMCID: PMCPMC4030719.

32. Swiech L, Heidenreich M, Banerjee A, Habib N, Li Y, Trombetta J, et al. In vivo interrogation of gene function in the mammalian brain using CRISPR-Cas9. Nat Biotechnol. 2015; 33(1):102-6. doi: 10.1038/nbt.3055. PubMed PMID: 25326897; PubMed Central PMCID: PMCPMC4492112.

33. Gene-therapy trials must proceed with caution. Nature. 2016; 534(7609):590. doi: 10.1038/534590a. PubMed PMID: 27357758.

34. Retracing events. Nat Biotechnol. 2007; 25(9):949. doi: 10.1038/nbt0907-949. PubMed PMID: 17846606.

35. Sibbald B. Death but one unintended consequence of gene-therapy trial. CMAJ. 2001; 164(11):1612. PubMed PMID: 11402803; PubMed Central PMCID: PMCPMC81135.

36. Martino A T, Suzuki M, Markusic D M, Zolotukhin I, Ryals R C, Moghimi B, et al. The genome of self-complementary adeno-associated viral vectors increases Toll-like receptor 9-dependent innate immune responses in the liver. Blood. 2011; 117(24):6459-68. doi: 10.1182/blood-2010-10-314518. PubMed PMID: 21474674; PubMed Central PMCID: PMCPMC3123017.

37. Zaiss A K, Liu Q, Bowen G P, Wong N C, Bartlett J S, Muruve D A. Differential activation of innate immune responses by adenovirus and adeno-associated virus vectors. J Virol. 2002; 76(9):4580-90. PubMed PMID: 11932423; PubMed Central PMCID: PMCPMC155101.

38. Ferreira V, Petry H, Salmon F. Immune Responses to AAV-Vectors, the Glybera Example from Bench to Bedside. Front Immunol. 2014; 5:82. doi: 10.3389/fimmu.2014.00082. PubMed PMID: 24624131; PubMed Central PMCID: PMCPMC3939780.

39. Manning W C, Paliard X, Zhou S, Pat Bland M, Lee A Y, Hong K, et al. Genetic immunization with adeno-associated virus vectors expressing herpes simplex virus type 2 glycoproteins B and D. J Virol. 1997; 71(10):7960-2. PubMed PMID: 9311887; PubMed Central PMCID: PMCPMC192154.

40. Liu D W, Tsao Y P, Kung J T, Ding Y A, Sytwu H K, Xiao X, et al. Recombinant adeno-associated virus expressing human papillomavirus type 16 E7 peptide DNA fused with heat shock protein DNA as a potential vaccine for cervical cancer. J Virol. 2000; 74(6):2888-94. PubMed PMID: 10684306; PubMed Central PMCID: PMCPMC111780.

41. Xin K Q, Urabe M, Yang J, Nomiyama K, Mizukami H, Hamajima K, et al. A novel recombinant adeno-associated virus vaccine induces a long-term humoral immune response to human immunodeficiency virus. Hum Gene Ther. 2001; 12(9):1047-61. doi: 10.1089/104303401750214276. PubMed PMID: 11399227.

42. Breous E, Somanathan S, Bell P, Wilson J M. Inflammation promotes the loss of adeno-associated virus-mediated transgene expression in mouse liver. Gastroenterology. 2011; 141(1):348-57, 57 e1-3. doi: 10.1053/j.gastro.2011.04.002. PubMed PMID: 21640112; PubMed Central PMCID: PMCPMC3269906.

43. Wang L, Wang H, Bell P, McCarter R J, He J, Calcedo R, et al. Systematic evaluation of AAV vectors for liver directed gene transfer in murine models. Mol Ther. 2010; 18(1):118-25. doi: 10.1038/mt.2009.246. PubMed PMID: 19861950; PubMed Central PMCID: PMCPMC2839210.

44. Zhu J, Huang X, Yang Y. The TLR9-MyD88 pathway is critical for adaptive immune responses to adeno-associated virus gene therapy vectors in mice. J Clin Invest. 2009; 119(8):2388-98. doi: 10.1172/JCI37607. PubMed PMID: 19587448; PubMed Central PMCID: PMCPMC2719948.
45. Kumagai Y, Takeuchi O, Akira S. TLR9 as a key receptor for the recognition of DNA. Adv Drug Deliv Rev. 2008; 60(7):795-804. doi: 10.1016/j.addr.2007.12.004. PubMed PMID: 18262306.
46. Rogers G L, Martino A T, Aslanidi G V, Jayandharan G R, Srivastava A, Herzog R W. Innate Immune Responses to AAV Vectors. Front Microbiol. 2011; 2:194. doi: 10.3389/fmicb.2011.00194. PubMed PMID: 21954398; PubMed Central PMCID: PMCPMC3175613.
47. Hosel M, Broxtermann M, Janicki H, Esser K, Arzberger S, Hartmann P, et al. Toll-like receptor 2-mediated innate immune response in human nonparenchymal liver cells toward adeno-associated viral vectors. Hepatology. 2012; 55(1):287-97. doi: 10.1002/hep.24625. PubMed PMID: 21898480.
48. Hensley S E, Amalfitano A. Toll-like receptors impact on safety and efficacy of gene transfer vectors. Mol Ther. 2007; 15(8):1417-22. doi: 10.1038/sj.mt.6300217. PubMed PMID: 17551505.
49. Lenert P S. Classification, mechanisms of action, and therapeutic applications of inhibitory oligonucleotides for Toll-like receptors (TLR) 7 and 9. Mediators Inflamm. 2010; 2010:986596. doi: 10.1155/2010/986596. PubMed PMID: 20490286; PubMed Central PMCID: PMCPMC2873634.
50. Trieu A, Roberts T L, Dunn J A, Sweet M J, Stacey K J. DNA motifs suppressing TLR9 responses. Crit Rev Immunol. 2006; 26(6):527-44. PubMed PMID: 17341193.
51. Krieg A M, Wu T, Weeratna R, Efler S M, Love-Homan L, Yang L, et al. Sequence motifs in adenoviral DNA block immune activation by stimulatory CpG motifs. Proc Natl Acad Sci USA. 1998; 95(21):12631-6. PubMed PMID: 9770537; PubMed Central PMCID: PMCPMC22882.
52. Gursel I, Gursel M, Yamada H, Ishii K J, Takeshita F, Klinman D M. Repetitive elements in mammalian telomeres suppress bacterial DNA-induced immune activation. J Immunol. 2003; 171(3):1393-400. PubMed PMID: 12874230.
53. Stunz L L, Lenert P, Peckham D, Yi A K, Haxhinasto S, Chang M, et al. Inhibitory oligonucleotides specifically block effects of stimulatory CpG oligonucleotides in B cells. Eur J Immunol. 2002; 32(5):1212-22. doi: 10.1002/1521-4141(200205)32:5<1212::AID-IMMU1212>3.0.CO;2-D. PubMed PMID: 11981808.
54. Lenert P, Rasmussen W, Ashman R F, Ballas Z K. Structural characterization of the inhibitory DNA motif for the type A (D)-CpG-induced cytokine secretion and NK-cell lytic activity in mouse spleen cells. DNA Cell Biol. 2003; 22(10):621-31. doi: 10.1089/104454903770238094. PubMed PMID: 14611683.
55. Lenert P, Yasuda K, Busconi L, Nelson P, Fleenor C, Ratnabalasuriar R S, et al. DNA-like class R inhibitory oligonucleotides (INH-ODNs) preferentially block autoantigen-induced B-cell and dendritic cell activation in vitro and autoantibody production in lupus-prone MRL-Fas(lpr/lpr) mice in vivo. Arthritis Res Ther. 2009; 11(3): R79. doi: 10.1186/ar2710. PubMed PMID: 19476613; PubMed Central PMCID: PMCPMC2714127.
56. Lenert P S. Targeting Toll-like receptor signaling in plasmacytoid dendritic cells and autoreactive B cells as a therapy for lupus. Arthritis Res Ther. 2006; 8(1):203. doi: 10.1186/ar1888. PubMed PMID: 16542467; PubMed Central PMCID: PMCPMC1526546.
57. Kaminski J J, Schattgen S A, Tzeng T C, Bode C, Klinman D M, Fitzgerald K A. Synthetic oligodeoxynucleotides containing suppressive TTAGGG motifs inhibit AIM2 inflammasome activation. J Immunol. 2013; 191(7):3876-83. doi: 10.4049/jimmunol.1300530. PubMed PMID: 23986531; PubMed Central PMCID: PMCPMC3878640.
58. Shirota H, Gursel I, Gursel M, Klinman D M. Suppressive oligodeoxynucleotides protect mice from lethal endotoxic shock. J Immunol. 2005; 174(8):4579-83. PubMed PMID: 15814679.
59. Peter M, Bode K, Lipford G B, Eberle F, Heeg K, Dalpke A H. Characterization of suppressive oligodeoxynucleotides that inhibit Toll-like receptor-9-mediated activation of innate immunity. Immunology. 2008; 123(1):118-28. doi: 10.1111/j.1365-2567.2007.02718.x. PubMed PMID: 17961163; PubMed Central PMCID: PMCPMC2433270.
60. Ohto U, Shibata T, Tanji H, Ishida H, Krayukhina E, Uchiyama S, et al. Structural basis of CpG and inhibitory DNA recognition by Toll-like receptor 9. Nature. 2015; 520(7549):702-5. doi: 10.1038/nature14138. PubMed PMID: 25686612.
61. Li Y, Cao H, Wang N, Xiang Y, Lu Y, Zhao K, et al. A novel antagonist of TLR9 blocking all classes of immunostimulatory CpG-ODNs. Vaccine. 2011; 29(11):2193-8. doi: 10.1016/j.vaccine.2010.10.042. PubMed PMID: 21036131.
62. Xiong W, MacColl Garfinkel A E, Li Y, Benowitz L I, Cepko C L. NRF2 promotes neuronal survival in neurodegeneration and acute nerve damage. J Clin Invest. 2015; 125(4):1433-45. doi: 10.1172/JCI79735. PubMed PMID: 25798616; PubMed Central PMCID: PMCPMC4396467.
63. Mingozzi F, High K A. Immune responses to AAV vectors: overcoming barriers to successful gene therapy. Blood. 2013; 122(1):23-36. doi: 10.1182/blood-2013-01-306647. PubMed PMID: 23596044; PubMed Central PMCID: PMCPMC3701904.
64. Karlstetter M, Ebert S, Langmann T. Microglia in the healthy and degenerating retina: insights from novel mouse models. Immunobiology. 2010; 215(9-10):685-91. doi: 10.1016/j.imbio.2010.05.010. PubMed PMID: 20573418.
65. Chinnery H R, Naranjo Golborne C, Leong C M, Chen W, Forrester J V, McMenamin P G. Retinal Microglial Activation Following Topical Application of Intracellular Toll-Like Receptor Ligands. Invest Ophthalmol Vis Sci. 2015; 56(12):7377-86. doi: 10.1167/iovs.15-17587. PubMed PMID: 26574796.
66. Doi Y, Mizuno T, Maki Y, Jin S, Mizoguchi H, Ikeyama M, et al. Microglia activated with the toll-like receptor 9 ligand CpG attenuate oligomeric amyloid {beta} neurotoxicity in in vitro and in vivo models of Alzheimer's disease. Am J Pathol. 2009; 175(5):2121-32. doi: 10.2353/ajpath.2009.090418. PubMed PMID: 19834064; PubMed Central PMCID: PMCPMC2774075.
67. Chinnery H R, McLenachan S, Binz N, Sun Y, Forrester J V, Degli-Esposti M A, et al. TLR9 ligand CpG-ODN applied to the injured mouse cornea elicits retinal inflammation. Am J Pathol. 2012; 180(1):209-20. doi: 10.1016/j.ajpath.2011.09.041. PubMed PMID: 22085974; PubMed Central PMCID: PMCPMC3338340.
68. Ye G J, Budzynski E, Sonnentag P, Nork T M, Miller P E, Sharma A K, et al. Safety and Biodistribution Evaluation in Cynomolgus Macaques of rAAV2tYF-PR1.7-hCNGB3, a Recombinant AAV Vector for Treatment of Achromatopsia. Hum Gene Ther Clin Dev. 2016. doi: 10.1089/hum.2015.164. PubMed PMID: 26956923.
69. Komaromy A M, Alexander J J, Rowlan J S, Garcia M M, Chiodo V A, Kaya A, et al. Gene therapy rescues cone function in congenital achromatopsia. Hum Mol Genet. 2010; 19(13):2581-93. doi: 10.1093/hmg/ddq136. PubMed PMID: 20378608; PubMed Central PMCID: PMCPMC2883338.
70. Schoenborn J R, Wilson C B. Regulation of interferon-gamma during innate and adaptive immune responses. Adv Immunol. 2007; 96:41-101. doi: 10.1016/S0065-2776(07)96002-2. PubMed PMID: 17981204.
71. Imai Y, Ibata I, Ito D, Ohsawa K, Kohsaka S. A novel gene iba1 in the major histocompatibility complex class III region encoding an EF hand protein expressed in a monocytic lineage. Biochem Biophys Res Commun. 1996; 224(3):855-62. doi: 10.1006/bbrc.1996.1112. PubMed PMID: 8713135.
72. Ito D, Imai Y, Ohsawa K, Nakajima K, Fukuuchi Y, Kohsaka S. Microglia-specific localisation of a novel calcium binding protein, Iba1. Brain Res Mol Brain Res. 1998; 57(1):1-9. PubMed PMID: 9630473.
73. Gray J T, Zolotukhin S. Design and construction of functional AAV vectors. Methods Mol Biol. 2011; 807: 25-46. doi: 10.1007/978-1-61779-370-72. PubMed PMID: 22034025.
74. Matsuda T, Cepko C L. Electroporation and RNA interference in the rodent retina in vivo and in vitro. Proc Natl Acad Sci USA. 2004; 101(1):16-22. doi: 10.1073/pnas.2235688100. PubMed PMID: 14603031; PubMed Central PMCID: PMCPMC314130.
75. Wang S, Sengel C, Emerson M M, Cepko C L. A gene regulatory network controls the binary fate decision of rod and bipolar cells in the vertebrate retina. Dev Cell. 2014; 30(5):513-27. doi: 10.1016/j.devcel.2014.07.018. PubMed PMID: 25155555; PubMed Central PMCID: PMCPMC4304698.
76. Martino A T, Herzog R W, Anegon I, Adjali O. Measuring immune responses to recombinant AAV gene transfer. Methods Mol Biol. 2011; 807:259-72. doi: 10.1007/978-1-61779-370-711. PubMed PMID: 22034034; PubMed Central PMCID: PMCPMC3593270.

We claim:

1. A recombinant viral genome covalently linked to an inhibitory nucleic acid sequence that binds to TLR9 but does not trigger TLR9 activation, wherein the viral genome is self-complementary, wherein the inhibitory nucleic acid sequence comprises the nucleotide sequence of SEQ ID NO: 1.

2. The recombinant viral genome of claim 1, wherein the recombinant viral genome is an adeno-associated virus (AAV) genome.

3. The recombinant viral genome of claim 1, wherein the recombinant viral genome is single stranded.

4. The recombinant viral genome of claim 1, wherein the viral genome is packaged in a virion.

5. The recombinant viral genome of claim 1, wherein the recombinant viral genome comprises a therapeutic gene.

6. The recombinant viral genome of claim 1, wherein the recombinant viral genome is a cytotoxic virus.

7. The recombinant viral genome of claim 1, wherein the inhibitory nucleic acid sequence comprises at least two copies of the nucleotide sequence of SEQ ID NO: 1.

8. The recombinant viral genome of claim 7, wherein each nucleotide sequence of SEQ ID NO: 1 is separated by a linker sequence.

9. The recombinant viral genome of claim 1, wherein the recombinant viral genome comprises a non-human gene.

10. The recombinant viral genome of claim 1, wherein the nucleotide sequence of SEQ ID NO: 1 is inserted downstream of or in a 3' untranslated region of the viral genome.

11. The recombinant viral genome of claim 1, wherein the recombinant viral genome is covalently linked by a phosphodiester bond to the nucleotide sequence of SEQ ID NO: 1.

12. The recombinant viral genome of claim 1 further comprising a detectable marker.

13. The recombinant viral genome of claim 12, wherein expression of the detectable marker is inducible.

14. The recombinant viral genome of claim 7 wherein the inhibitory nucleic acid sequence comprises at least three copies of the nucleotide sequence of SEQ ID NO: 1, each copy separated by a linker sequence.

15. A method of treating a mammal, comprising: administering to the mammal the recombinant viral genome of claim 1.

16. A method of producing the recombinant viral genome of claim 1, comprising:

inserting into a viral genome the nucleotide sequence of SEQ ID NO: 1.

17. A nucleic acid vector comprising the recombinant viral genome of claim 1.

18. The recombinant viral genome of claim 1, wherein the inhibitory nucleic acid sequence comprises the nucleotide sequence of SEQ ID NO: 1.

19. A recombinant viral genome covalently linked to an inhibitory nucleic acid sequence that binds to TLR9 but does not trigger TLR9 activation, wherein the inhibitory nucleic acid sequence is at least 95% identical to the nucleotide sequence of SEQ ID NO: 1.

20. The recombinant viral genome of claim 19, the inhibitory nucleic acid sequence comprises the nucleotide sequence of SEQ ID NO: 1.

21. The recombinant viral genome of claim 19, wherein the recombinant viral genome is an adeno-associated virus (AAV) genome.

22. The recombinant viral genome of claim 20, wherein the recombinant viral genome is an adeno-associated virus (AAV) genome.

* * * * *